(12) United States Patent
Sasiela et al.

(10) Patent No.: US 10,995,150 B2
(45) Date of Patent: *May 4, 2021

(54) METHODS FOR INHIBITING ATHEROSCLEROSIS BY ADMINISTERING AN ANTI-PCSK9 ANTIBODY

(71) Applicants: REGENERON PHARMACEUTICALS, INC., Tarrytown, NY (US); SANOFI BIOTECHNOLOGY, Paris (FR)

(72) Inventors: William J. Sasiela, Tarrytown, NY (US); Viktoria Gusarova, Tarrytown, NY (US); Anusch Peyman, Frankfurt am Main (DE); Hans Ludwig Schäfer, Frankfurt am Main (DE); Uwe Schwahn, Frankfurt am Main (DE)

(73) Assignees: REGENERON PHARMACEUTICALS, INC., Tarrytown, NY (US); SANOFI BIOTECHNOLOGY, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/505,074

(22) Filed: Jul. 8, 2019

(65) Prior Publication Data

US 2020/0071422 A1  Mar. 5, 2020

Related U.S. Application Data

(63) Continuation of application No. 15/874,807, filed on Jan. 18, 2018, now abandoned, which is a continuation of application No. 14/896,196, filed as application No. PCT/US2014/041204 on Jun. 6, 2014, now Pat. No. 10,494,442.

(60) Provisional application No. 61/832,459, filed on Jun. 7, 2013, provisional application No. 61/892,215, filed on Oct. 17, 2013, provisional application No. 61/944,855, filed on Feb. 26, 2014, provisional application No. 62/002,508, filed on May 23, 2014.

(30) Foreign Application Priority Data

Jun. 7, 2013 (EP) .................................... 13305762
Oct. 18, 2013 (EP) .................................... 13306436

(51) Int. Cl.
| | |
|---|---|
| *A61K 39/395* | (2006.01) |
| *A61K 9/10* | (2006.01) |
| *C07K 16/40* | (2006.01) |
| *A61P 9/10* | (2006.01) |
| *A61K 31/4015* | (2006.01) |
| *C07K 14/47* | (2006.01) |
| *A61K 39/00* | (2006.01) |

(52) U.S. Cl.
CPC .......... *C07K 16/40* (2013.01); *A61K 31/4015* (2013.01); *A61K 39/3955* (2013.01); *A61P 9/10* (2018.01); *A61K 2039/505* (2013.01); *C07K 14/4703* (2013.01); *C07K 2317/21* (2013.01); *C07K 2317/565* (2013.01); *C07K 2317/76* (2013.01); *Y02A 50/30* (2018.01)

(58) Field of Classification Search
CPC ........ C07K 16/40; A61K 39/3955; A61P 9/10
See application file for complete search history.

(56) References Cited

U.S. PATENT DOCUMENTS

| | | |
|---|---|---|
| 5,260,440 A | 11/1993 | Hirai et al. |
| 5,273,995 A | 12/1993 | Roth et al. |
| 5,939,598 A | 8/1999 | Kucherlapati et al. |
| 6,596,541 B2 | 7/2003 | Murphy et al. |
| 7,029,895 B2 | 4/2006 | Glucksmann et al. |
| 7,129,338 B1 | 10/2006 | Ota et al. |
| 7,300,754 B2 | 11/2007 | Fadel et al. |
| 7,482,147 B2 | 1/2009 | Glucksmann et al. |
| 7,572,618 B2 | 8/2009 | Mintier et al. |
| 7,754,208 B2 | 7/2010 | Ledbetter et al. |
| 8,030,457 B2 | 10/2011 | Jackson et al. |
| 8,062,640 B2 | 11/2011 | Sleeman et al. |
| 8,080,243 B2 | 12/2011 | Liang et al. |
| 8,168,762 B2 | 5/2012 | Jackson et al. |
| 8,188,233 B2 | 5/2012 | Condra et al. |
| 8,188,234 B2 | 5/2012 | Condra et al. |
| 8,357,371 B2 | 1/2013 | Sleeman et al. |

(Continued)

FOREIGN PATENT DOCUMENTS

| | | |
|---|---|---|
| CN | 101489565 A | 7/2009 |
| EP | 0 521 471 B1 | 10/2000 |

(Continued)

OTHER PUBLICATIONS

U.S. Appl. No. 14/896,196, filed Dec. 4, 2016, 2016/0115246, Apr. 28, 2016, U.S. Pat. No. 10,494,442, Dec. 3, 2019, William J. Sasiela.

(Continued)

*Primary Examiner* — Zachary C Howard

(74) *Attorney, Agent, or Firm* — Lathrop Gpm LLP; James H. Velema, Esq.; James V. DeGiulio, Esq.

(57) ABSTRACT

The present invention provides methods and compositions for inhibiting atherosclerotic plaque formation in a subject. In certain embodiments, the methods of the present invention comprise selecting a subject who has, or is at risk of developing, atherosclerosis, and administering to the subject a pharmaceutical composition comprising a proprotein convertase subtilisin/kexin type 9 (PCSK9) inhibitor. In certain embodiments, the PCSK9 inhibitor is an anti-PCSK9 antibody, or antigen binding protein.

19 Claims, 10 Drawing Sheets

Specification includes a Sequence Listing.

(56) References Cited

U.S. PATENT DOCUMENTS

| | | |
|---|---|---|
| 8,748,115 B2 | 6/2014 | Ni et al. |
| 8,795,669 B2 | 8/2014 | Walsh et al. |
| 8,829,165 B2 | 9/2014 | Jackson et al. |
| 8,883,157 B1 | 11/2014 | Clube |
| 9,034,332 B1 | 5/2015 | Clube |
| 9,193,801 B2 | 11/2015 | Walsh et al. |
| 9,540,449 B2 | 1/2017 | Yancopoulos et al. |
| 9,550,837 B2 | 1/2017 | Sleeman et al. |
| 9,561,155 B2 | 2/2017 | Hanotin et al. |
| 9,682,013 B2 | 6/2017 | Hanotin et al. |
| 9,724,411 B2 | 8/2017 | Sleeman et al. |
| 10,494,442 B2 * | 12/2019 | Sasiela ............... A61K 39/3955 |
| 2003/0118592 A1 | 6/2003 | Ledbetter et al. |
| 2003/0133939 A1 | 7/2003 | Ledbetter et al. |
| 2004/0101920 A1 | 5/2004 | Radziejewski et al. |
| 2006/0147945 A1 | 7/2006 | Edmonds et al. |
| 2007/0082345 A1 | 4/2007 | Ota et al. |
| 2007/0224663 A1 | 9/2007 | Rosen et al. |
| 2008/0008697 A1 | 1/2008 | Mintier et al. |
| 2009/0142352 A1 | 6/2009 | Jackson et al. |
| 2009/0232795 A1 | 9/2009 | Condra et al. |
| 2009/0246192 A1 | 10/2009 | Condra et al. |
| 2009/0269350 A1 | 10/2009 | Glucksmann et al. |
| 2009/0318536 A1 | 12/2009 | Freier et al. |
| 2009/0326202 A1 | 12/2009 | Jackson et al. |
| 2010/0040610 A1 | 2/2010 | Sitlani et al. |
| 2010/0040611 A1 | 2/2010 | Sparrow et al. |
| 2010/0041102 A1 | 2/2010 | Sitlani et al. |
| 2010/0068199 A1 | 3/2010 | Liang et al. |
| 2010/0136028 A1 | 6/2010 | Sparrow |
| 2010/0150937 A1 | 6/2010 | Sparrow et al. |
| 2010/0166768 A1 | 7/2010 | Sleeman et al. |
| 2010/0233177 A1 | 9/2010 | Yowe et al. |
| 2011/0009628 A1 | 1/2011 | Liu et al. |
| 2011/0015252 A1 | 1/2011 | Fitzgerald et al. |
| 2011/0027287 A1 | 2/2011 | Jackson et al. |
| 2011/0033465 A1 | 2/2011 | Hedrick et al. |
| 2011/0065902 A1 | 3/2011 | Sleeman et al. |
| 2011/0098450 A1 | 4/2011 | Igawa et al. |
| 2011/0111406 A1 | 5/2011 | Igawa et al. |
| 2011/0142849 A1 | 6/2011 | Rue et al. |
| 2011/0171241 A1 | 7/2011 | Dix et al. |
| 2011/0229489 A1 | 9/2011 | Pons et al. |
| 2011/0230542 A1 | 9/2011 | Tan et al. |
| 2011/0256148 A1 | 10/2011 | Sleeman et al. |
| 2011/0313024 A1 | 12/2011 | Beigelman et al. |
| 2012/0014951 A1 | 1/2012 | Liang et al. |
| 2012/0015435 A1 | 1/2012 | Liang et al. |
| 2012/0020975 A1 | 1/2012 | Jackson et al. |
| 2012/0027765 A1 | 2/2012 | Jackson et al. |
| 2012/0076799 A1 | 3/2012 | Sparrow et al. |
| 2012/0077964 A1 | 3/2012 | Sparrow et al. |
| 2012/0082679 A1 | 4/2012 | Sparrow et al. |
| 2012/0082680 A1 | 4/2012 | Sitlani et al. |
| 2012/0093818 A1 | 4/2012 | Jackson et al. |
| 2012/0097565 A1 | 4/2012 | Dix et al. |
| 2012/0122954 A1 | 5/2012 | Staarup et al. |
| 2012/0195910 A1 | 8/2012 | Wu et al. |
| 2012/0213794 A1 | 8/2012 | Luo et al. |
| 2012/0213797 A1 | 8/2012 | Jackson et al. |
| 2012/0219558 A1 | 8/2012 | Ni et al. |
| 2012/0231005 A1 | 9/2012 | Luo et al. |
| 2012/0251544 A1 | 10/2012 | Jackson et al. |
| 2013/0011866 A1 | 1/2013 | Igawa et al. |
| 2013/0064825 A1 | 3/2013 | Chan et al. |
| 2013/0064834 A1 | 3/2013 | Sleeman et al. |
| 2013/0071405 A1 | 3/2013 | Davies et al. |
| 2013/0085266 A1 | 4/2013 | Sleeman et al. |
| 2013/0115223 A1 | 5/2013 | Sparrow |
| 2013/0189277 A1 | 7/2013 | Walsh et al. |
| 2013/0243784 A1 | 9/2013 | Swergold |
| 2013/0245235 A1 | 9/2013 | Jackson et al. |
| 2014/0004122 A1 | 1/2014 | Chan et al. |
| 2014/0030270 A1 | 1/2014 | Clogston et al. |
| 2014/0065649 A1 | 3/2014 | Schafer et al. |
| 2014/0099312 A1 | 4/2014 | Sleeman et al. |
| 2014/0154262 A1 | 6/2014 | Hanotin et al. |
| 2014/0161821 A1 | 6/2014 | Udata |
| 2014/0178402 A1 | 6/2014 | Hanotin et al. |
| 2014/0341928 A1 | 11/2014 | Walsh et al. |
| 2014/0356370 A1 | 12/2014 | Swergold et al. |
| 2014/0356371 A1 | 12/2014 | Swergold et al. |
| 2015/0140002 A1 | 5/2015 | Baccara-Dinet et al. |
| 2015/0152191 A1 | 6/2015 | Baccara-Dinet et al. |
| 2015/0231236 A1 | 8/2015 | Pordy et al. |
| 2015/0283236 A1 | 10/2015 | Baccara-Dinet et al. |
| 2015/0284473 A1 | 10/2015 | Bessac et al. |
| 2015/0284474 A1 | 10/2015 | Sleeman et al. |
| 2016/0032015 A1 | 2/2016 | Walsh et al. |
| 2016/0115246 A1 | 4/2016 | Sasiela et al. |
| 2016/0137745 A1 | 5/2016 | Baccara-Dinet et al. |
| 2016/0137746 A1 | 5/2016 | Hanotin et al. |
| 2016/0152734 A1 | 6/2016 | Udata |
| 2017/0049886 A1 | 2/2017 | Pordy et al. |
| 2017/0096496 A1 | 4/2017 | Sleeman et al. |
| 2017/0266079 A1 | 9/2017 | Hanotin et al. |
| 2017/0340515 A1 | 11/2017 | Hanotin et al. |

FOREIGN PATENT DOCUMENTS

| | | |
|---|---|---|
| EP | 1 067 182 A2 | 1/2001 |
| EP | 0 409 281 B1 | 10/2001 |
| EP | 1 514 933 A1 | 3/2005 |
| EP | 1 317 537 B1 | 12/2006 |
| EP | 1 618 212 B1 | 11/2007 |
| EP | 2 703 008 A1 | 3/2014 |
| EP | 2 703 009 A1 | 3/2014 |
| EP | 2 706 070 A1 | 3/2014 |
| WO | WO 1993/000807 A1 | 1/1993 |
| WO | WO 1997/035620 A1 | 10/1997 |
| WO | WO 1998/022136 A2 | 5/1998 |
| WO | WO 1999/038495 A2 | 8/1999 |
| WO | WO 2001/057081 A2 | 8/2001 |
| WO | WO 2005/103081 A2 | 11/2005 |
| WO | WO 2007/149334 A2 | 12/2007 |
| WO | WO 2008/057457 A2 | 5/2008 |
| WO | WO 2008/057458 A2 | 5/2008 |
| WO | WO 2008/057459 A2 | 5/2008 |
| WO | WO 2008/063382 A2 | 5/2008 |
| WO | WO 2008/125623 A2 | 10/2008 |
| WO | WO 2008/133647 A2 | 11/2008 |
| WO | WO 2009/026558 A1 | 2/2009 |
| WO | WO 2009/055783 A2 | 4/2009 |
| WO | WO 2007/143315 A2 | 7/2009 |
| WO | WO 2009/100297 A1 | 8/2009 |
| WO | WO 2009/100318 A1 | 8/2009 |
| WO | WO 2010/029513 A2 | 3/2010 |
| WO | WO 2010/032220 A1 | 3/2010 |
| WO | WO 2010/077854 A1 | 7/2010 |
| WO | WO 2010/148337 A1 | 12/2010 |
| WO | WO 2011/028938 A1 | 3/2011 |
| WO | WO 2011/039578 A1 | 4/2011 |
| WO | WO 2011/072263 A1 | 6/2011 |
| WO | WO 2011/111007 A2 | 9/2011 |
| WO | WO 2011/117401 A1 | 9/2011 |
| WO | PCT/EP2012/051320 | 1/2012 |
| WO | PCT/EP2012/051321 | 1/2012 |
| WO | WO 2012/054438 A1 | 4/2012 |
| WO | WO 2012/064792 A2 | 5/2012 |
| WO | WO 2012/101251 A1 | 8/2012 |
| WO | WO 2012/101252 | 8/2012 |
| WO | WO 2012/101252 A2 | 8/2012 |
| WO | WO 2012/101253 | 8/2012 |
| WO | WO 2012/101253 A1 | 8/2012 |
| WO | WO 2012/109530 A1 | 8/2012 |
| WO | WO 2012/146776 A1 | 11/2012 |
| WO | WO 2012/154999 A1 | 11/2012 |
| WO | WO 2013/039958 A1 | 3/2013 |
| WO | WO 2013/039969 A1 | 3/2013 |
| WO | WO 2013/158984 A1 | 10/2013 |
| WO | PCT/US2014/041204 | 6/2014 |
| WO | PCT/US2017/060109 | 10/2014 |
| WO | PCT/US2014/065149 | 11/2014 |
| WO | WO 2014/194111 A1 | 12/2014 |

(56) References Cited

FOREIGN PATENT DOCUMENTS

| WO | WO 2014/197752 | 12/2014 |
|---|---|---|
| WO | WO 2014/197752 A1 | 12/2014 |
| WO | PCT/US2015/020564 | 3/2015 |
| WO | WO 2015/054619 | 4/2015 |
| WO | WO 2015/054619 A2 | 4/2015 |
| WO | WO 2015/073494 | 5/2015 |
| WO | WO 2015/073494 A1 | 5/2015 |
| WO | PCT/US2015/040754 | 7/2015 |
| WO | PCT/US2015/040765 | 7/2015 |
| WO | WO 2015/123423 A2 | 8/2015 |
| WO | WO 2015/140079 A1 | 9/2015 |
| WO | WO 2015/142668 | 9/2015 |
| WO | WO 2015/142668 A1 | 9/2015 |
| WO | WO 2016/011256 | 1/2016 |
| WO | WO 2016/011256 A1 | 1/2016 |
| WO | WO 2016/011260 | 1/2016 |
| WO | WO 2016/011260 A1 | 1/2016 |

OTHER PUBLICATIONS

U.S. Appl. No. 16/505,074, filed Jul. 8, 2019, William J. Sasiela.
U.S. Appl. No. 14/511,975, filed Oct. 10, 2014, 2015/0140002, May 21, 2015, Marie Baccara-Dinet.
U.S. Appl. No. 13/982,381, filed Jul. 29, 2013, 2014/0178402, Jun. 26, 2014, U.S. Pat. No. 9,682,013, Jun. 20, 2017, Corinne Hanotin.
U.S. Appl. No. 13/982,373, filed Jul. 29, 2013, 2014/0154262, Jun. 5, 2014, U.S. Pat. No. 9,561,155, Feb. 7, 2017, Corinne Hanotin.
U.S. Appl. No. 16/365,317, filed Mar. 26, 2019, 2019/0343719, Nov. 14, 2019, Corinne Hanotin.
U.S. Appl. No. 14/539,199, filed Nov. 12, 2014, 2015/0152191, Jun. 4, 2015, U.S. Pat. No. 10,428,157, Oct. 1, 2019, Marie Baccara-Dinet.
U.S. Appl. No. 16/415,837, filed May 17, 2019, 2020/0024364, Jan. 23, 2020, Marie Baccara-Dinet.
U.S. Appl. No. 14/801,384, filed Jul. 16, 2015, 2016/0137745, May 19, 2016, U.S. Pat. No. 10/544,232, Jan. 28, 2020, Marie Baccara-Dinet.
U.S. Appl. No. 16/707,492, filed Dec. 9, 2019, 2020/0216565, Jul. 9, 2020, Marie Baccara-Dinet.
U.S. Appl. No. 14/657,192, filed Mar. 13, 2015, 2015/0284473, Oct. 8, 2015, Laurence Bessac.
U.S. Appl. No. 16/662,313, filed Oct. 24, 2019, Corinne Hanotin.
U.S. Appl. No. 12/637,942, filed Dec. 15, 2009, 2010/0166768, Jul. 1, 2010, U.S. Pat. No. 8,062,640, Nov. 22, 2011, Mark W. Sleeman.
U.S. Appl. No. 13/095,234, filed Apr. 27, 2011, 2011/0256148, Oct. 20, 2011, U.S. Pat. No. 8,357,371, Jan. 22, 2013, Mark W. Sleeman.
U.S. Appl. No. 14/100,992, filed Dec. 9, 2013, 2014/0099312, Apr. 10, 2014, U.S. Pat. No. 9,724,411, Aug. 8, 2017, Mark W. Sleeman.
U.S. Appl. No. 12/949,846, filed Nov. 19, 2010, 2011/0065902, Mar. 17, 2011, U.S. Pat. No. 8,501,184, Aug. 6, 2013, Mark W. Sleeman.
U.S. Appl. No. 14/737,488, filed Jun. 12, 2015, 2015/0284474, Oct. 8, 2015, U.S. Pat. No. 9,550,837, Jan. 24, 2017, Mark W. Sleeman.
U.S. Appl. No. 15/377,364, filed Dec. 13, 2016, 2017/0096496, Apr. 6, 2017, U.S. Pat. No. 10,023,654, Jul. 17, 2018, Mark W. Sleeman.
U.S. Appl. No. 13/559,862, filed Jul. 27, 2012, 2013/0189277, Jul. 25, 2013, U.S. Pat. No. 8,795,669, Aug. 5, 2014, Scott Walsh.
U.S. Appl. No. 14/319,730, filed Jun. 30, 2014, 2014/0341928, Nov. 20, 2014, U.S. Pat. No. 9,193,801, Nov. 24, 2015, Scott M. Walsh.
U.S. Appl. No. 15/603,732, filed May 24, 2017, 2018/0044436, Feb. 15, 2018, U.S. Pat. No. 10,472,425, Nov. 12, 2019, Scott M. Walsh.
U.S. Appl. No. 16/384,298, filed Apr. 15, 2019, 2019/0284301, Sep. 19, 2019, Scott M. Walsh.
U.S. Appl. No. 13/611,405, filed Sep. 12, 2012, 2013/0243784, Sep. 19, 2013, U.S. Pat. No. 10,076,571, Sep. 18, 2018, Gary Swergold.
U.S. Appl. No. 16/053,448, filed Aug. 2, 2018, 2018/0333490, Nov. 22, 2018, Gary Swergold.
U.S. Appl. No. 14/290,544, filed May 29, 2014, 2014/0356371, Dec. 4, 2014, U.S. Pat. No. 10,111,953, Oct. 30, 2018, Gary Swergold.
U.S. Appl. No. 16/022,255, filed Jun. 28, 2018, 2018/0296672, Oct. 18, 2018, Robert C. Pordy.
U.S. Appl. No. 15/238,890, filed Aug. 17, 2016, 2017/0049886, Feb. 23, 2017, Robert C. Pordy.
Gaudet et al. (Sep. 29, 2016) "Effect of Alirocumab on Lipoprotein(a) Over ≥1.5 Years (from the Phase 3 ODYSSEY Program)," Am. J. Cardiol. 119:40-46.
Kolata (Jul. 27, 2015) "Praluent Looks Cheap to Those with Extreme Cholesterol" the New York Times. Accessible on the Internet at URL: www.nytimes.com/2015/07/28/health/praluent-looks-cheap-to-those-with-extreme-cholesterol.html. [Last Accessed on Sep. 5, 2017].
Moriarty (May 2015) "PCSK9 Inhibitors and their Effect on Patients who are Statin Intolerant or Receiving Lipoprotein-apheresis," the 10th International Society for Apheresis Congress. May 13-16, 2015. Cancun, Mexico.
Reyes-Soffer et al. (Jan. 23, 2017) "Effects of PCSK9 Inhibition with Alirocumab on Lipoprotein Metabolism in Healthy Humans," Circulation 135:352-362.
Todo et al. (2004) "Detailed analysis of serum lipids and lipoproteins from Japanese type III hyperlipoproteinemia with apolipoprotein E2/2 phenotype," Clin. Chim. Acta. 348:35-40.
International Search Report with Written Opinion corresponding to International Patent Application No. PCT/US2014/040050, dated Oct. 6, 2014.
Response to Third Party Oppositions corresponding to European Patent Application No. 12761864.3, dated Dec. 9, 2016.
Third Party Observations corresponding to European Patent Application No. 12761864.3, dated Jul. 7, 2017.
Bambauer et al. (2003) "Low-density Lipoprotein Apheresis: An Overview," Therapuetic Apherisis and Dialysis. 7(4):382-390.
Beliard et al. (Mar. 3, 2014) "Improvement in LDL-cholesterol levels of patients with familial hypercholesterolemia: can we do better? Analysis of results obtained during the past two decades in 1669 French subjects," Atherosclerosis. 234:136-141.
Berthold et al. (Jan. 2013) "Hyperlipoproteinemia(a): Clinical significance and treatment options," Atherosclerosis Supplements 14:1-5.
Borberg (Apr. 2013) "The lower the better: Target values after LDL-Apheresis and semi-selective LDL-elimination therapies," Transfusion and Apheresis Science. 48:203-206.
Demant et al. (2001) "The metabolism of lipoprotein(a) and other apolipoprotein B-containing lipoproteins: a kinetic study in humans," Atherosclerosis 157:325-339.
Huijgen et al. (2010) "Two years after molecular diagnosis of familial hypercholesterolemia: majority on cholesterol-lowering treatment but a minority reaches treatment goal," PLoS One. 5(2):e9220. pp. 1-7.
Koschinsky et al. (2009) In; Clinical Lipidology: A Companion to Braunwald's Heart Disease. Ed: Ballantyne. pp. 136-143.
Leebmann et al. (Dec. 17, 2013) Circulation "Lipoprotein Apheresis in Patients With Maximally Tolerated Lipid-Lowering Therapy, Lipoprotein(a)-Hyperlipoproteinemia, and Progressive Cardiovascular Disease," Circulation. 128(24):2567-2576.
McPherson (2013) "Remnant Cholesterol: Non-(HDL-C + LDL-C) as a Coronary Artery Disease Risk Factor," Journal of the American College of Cardiology. 61(4):437-439.
Moon (2007) "Lipoprotein(a) and LDL Particle Size are Related to the Severity of Coronary Artery Disease", Cardiology 108:282-289.
Neil et al. (2004) "Established and emerging coronary risk factors in patients with heterozygous familial hypercholesterolaemia," Heart. 90(12):1431-1437.
Pijlman et al. (2010) "Evaluation of cholesterol lowering treatment of patients with familial hypercholesterolemia: a large cross-sectional study in the Netherlands," Atherosclerosis. 209:189-194.
Rahilly-Tierney et al. (2009) "Low-Density Lipoprotein Reduction and Magnitude of Cardiovascular Risk Reduction," Prev. Cardiol. 12(2):80-87.
Regeneron and Sanofi (Nov. 5, 2012) "IR Conference Call on PCSK9: SAR236553/REGN727 PCSK9 Antibody for Hypercholesterolemia Phase 3 ODYSSEY Program Underway," Accessible on the Internet at URL: www.sanofi.com/Images/31341_2012-11-05_PCSK9_call.pdf. pp. 1-30. [Last Accessed on Sep. 5, 2017].

(56) References Cited

OTHER PUBLICATIONS

Robinson et al. (2013) "Management of Familial Hypercholesterolemia: A Review of the Recommendations from the National Lipid Association Expert Panel on Familial Hypercholesterolemia," J. Manag. Care Pharm. 19(2):139-149.
Saeedi et al. (Mar. 31, 2016) "Lipoprotein (a), an independent cardiovascular risk marker," Clinical Diabetes and Endocrinology. 2:7. pp. 1-6.
Sahebkar et al. (Aug. 8, 2013) "New LDL-Cholesterol Lowering Therapies: Pharmacology, Clinical Trials, and Relevance to Acute Coronary Syndromes," Clinical Therapeutics. 35(8):1082-1098.
Shoji et al. (1998) "Intermediate-Density Lipoprotein as an Independent Risk Factor for Aortic Atherosclerosis in Hemodialysis Patients," J. Am. Soc. Nephrol. 9:1277-1284.
Stone et al. (2014) "2013 ACC/AHA Guideline on the Treatment of Blood Cholesterol to Reduce Atherosclerotic Cardiovascular Risk in Adults," Circulation. 129:S1-S48.
Tavori et al. (Oct. 11, 2013) "Loss of Plasma Proprotein Convertase Subtilisin/Kevin 9 (PCSK9) After Lipoprotein Apheresis," Circulation Research. 113(12):1290-1295.
Thompsen et al. (2006) "A systematic review of Ldl apheresis in the treatment of cardiovascular disease," Atherosclerosis. 189:31-38.
Van Wissen et al. (2003) "Long term statin treatment reduces lipoprotein(a) concentrations in heterozygous familial hypercholesterolaemia," Heart. 89(8):893-896.
Walji (2013) "Lipoprotein Apheresis for the Treatment of Familial Hypercholesterolemia," Clinical Lipidology. 8(5):573-586.
Mettinen et al. (1971) "Cholesterol production in obesity," Circulation. 44(5):842-850.
Anthem (Sep. 21, 2015) "Proprotein Convertase Subtilisin Kexin 9 (PCSK9) Inhibitors," Policy No. DRUG.00078. American Medical Association. Accessible on the Internet at URL: https://www.anthem.com/ca/medicalpolicies/policies/mp_pw_c182635.htm. [Last Accessed Apr. 27, 2016].
Barbie et al. (1998) "The Human Immunoglobulin Kappa Variable (IGKV) Genes and Joining (IGKJ) Segments," Exp. Clin. Immunogenet. 15:171-183.
Breen et al. (2001) "Effect of moisture on the stability of a lyophilized humanized monoclonal antibody formulation," Pharmaceutical Research. 18(9):1345-1353.
Cannon et al. (Aug. 31, 2014) "Efficacy and safety of alirocumab in high cardiovascular risk patients with inadequately controlled hypercholesterolaemia on maximally tolerated daily statin: results from the ODYSSEY COMBO II study," presentation presented at the ESC Congress 2014.
Carpenter (1997) "Rational Design of Stable Lyophilized Protein Formulations: Some Practical Advice," Pharm. Res. 14(8):969-975.
Daugherty et al. (2006) "Formulation and delivery issues for monoclonal antibody therapeutics," Advanced Drug Delivery Reviews 58:686-706.
Davidson et al. (2011) "Clinical utility of inflammatory markers and advanced lipoprotein testing: Advice from an expert panel of lipid specialists," Journal of Clinical Lipidology. 5:338-367.
Defesche et al. (Jun. 2-5, 2013) "Natural history of autosomal dominant hypercholesterolemia caused by gain-of-function mutations in proprotein convertase subtilisin/kexin type 9 (PCSK9) (funded by Regeneron/Sanofi)," Abstract of a presentation presented at the 81st European Atherosclerosis Society (EAS) Congress, Jun. 2-5, 2013, Lyon, France.
Defesche et al. (Jun. 2-5, 2013) "Natural history of autosomal dominant hypercholesterolemia caused by gain-of-function mutations in proprotein convertase subtilisin/kexin type 9 (PCSK9) (funded by Regeneron/Sanofi)," Presentation presented at the 81st European Atherosclerosis Society (EAS) Congress, Jun. 2-5, 2013, Lyon, France.
Katayama et al. (2004) "Retrospective statistical analysis of lyophilized Protein Formulations of Progenipoietin Using PLS: Determination of the Critical Parameters for Long-Term Storage Stability," J. Pharm. Sci. 93(10):2609-2623.

Kostner et al. (Jun. 4, 2013) "When should we measure lipoprotein (a)?" European Heart Journal. 34:3268-3276.
Lefranc et al. (2009) "IMGT®, the international ImMunoGeneTics information system®," Nucl. Acids Res. 37:D1006-D1012.
Li et al. (2009) "Recent Patents on PCSK9: A New Target for Treating Hypercholesterolemia," Recent Patents on DNA and Gene Sequences. 3(3):201-212.
Majumdar et al. (2011) "Evaluation of the effect of syringe surfaces on protein formulations," Journal of Pharmaceutical Sciences. 100(7):2563-2573.
McKenney et al. (Jun. 2-5, 2013) "Dynamics between the monoclonal antibody SAR236553/REGN727, proprotein convertase subtilisin/kexin type 9 (PCSK9) and low-density lipoprotein cholesterol (LDL-C) levels (funding: Regeneron/Sanofi)," Abstract of an oral presentation at the 81st European Atherosclerosis Society (EAS) Congress, Jun. 2-5, 2013, Lyon, France.
McKenney et al. (Jun. 2-5, 2013) "Dynamics between the monoclonal antibody SAR236553/REGN727, proprotein convertase subtilisin/kexin type 9 (PCSK9) and low-density lipoprotein cholesterol (LDL-C) levels (funding: Regeneron/Sanofi)," Presented as a poster presentation at the 81st European Atherosclerosis Society (EAS) Congress, Jun. 2-5, 2013, Lyon, France.
Rader et al. (1995) "The Low Density Lipoprotein Receptor is not Required for Normal Catabolism of Lp(a) in Humans," the Journal of Clinical Investigation. 95:1403-1408.
Regeneron Pharmaceuticals (Nov. 5, 2012) " Sanofi and Regeneron Announce Patient Enrollment in Cardiovascular Outcome Trial with Antibody to PCSK9 for Hypercholesterolemia," Press Release. Acquire Media.
Robinson (2002) "Protein Deamidation," Proc. Natl. Acad. Sci. USA. 99(8):5283-5288.
Romagnuolo et al. (Mar. 16, 2015) "Lipoprotein(a) Catabolism is Regulated by Proprotein Convertase Subtilisin/Kexin Type 9 through the Low Density Lipoprotein Receptor," the Journal of Biological Chemistry. 290(18):11649-11662.
Scaviner et al. (1999) "Protein Displays of the Human Immunoglobulin Heavy, Kappa and Lambda Variable and Joining Regions," Exp. Clin. Immunogenet. 16:234-240.
Schäfer et al. (Mar. 14-16, 2011) "Cholesterol lowering effect of SAR236553/REGN727, a fully human PCSK9 blocking monoclonal antibody in male Syrian hamster," Presented as a poster at the Drugs Affecting Lipid Metabolism (DALM)—XVII International Symposium, Mar. 14-16, 2011, Doha, Qatar.
Varrett et al. (1999) "A third major locus for autosomal dominant hypercholesterolemia Maps to 1p34.1-p32," Am. J. Hum. Genet. 64:1378-1387.
Wang (1999) "Instability, stabilization, and formulation of liquid protein pharmaceuticals," International J. Pharmaceutics 185(2):129-188.
Wang (2009) "Fixed dosing versus body size-based dosing of monoclonal antibodies in adult clinical trials," J Clin Pharmacol. 49(9):1012-1024.
Webb et al. (2002) "A new mechanism for decreasing aggregation of Recombinant Human lnterferon-Y by a Surfactant: Slowed Dissolution of Lyophilized Formulations in a Solution Containing 0.03% Polysorbate 20," J. Pharm. Sci. 91(2):543-558.
Cariou et al. (May 23-26, 2015) "Patient and physician perspectives on administration of the PCSK9 monoclonal antibody alirocumab, an injectable medication to lower LDL-C levels," International Symposium on Atherosclerosis. Abstract No. 1039.
Dube et al. (Apr. 2012) "Lipoprotein(a): more interesting than ever after 50 years," Curr. Opin. Lipidol. 23:133-140.
Hiriyama et al. (Jan. 1, 2014) "Effects of evolocumab (AMG 145), a monoclonal antibody to PCSK9, in hypercholesterolemic, statin-treated Japanese patients at high cardiovascular risk-primary results from the phase 2 Yukawa study," Circulation Journal. 78(5):1073-1082.
Konrad et al. (2011) "Effects of currently prescribed LDL-C-lowering drugs on PCSK9 and implications for the next generation of LDL-C-lowering agents," Lipids in Health and Disease. 10(1):38. 10 pages.

(56) References Cited

OTHER PUBLICATIONS

Koschinsky et al. (Dec. 2014) "Lipoprotein(a): an important cardiovascular risk factor and a clinical conundrum," Endocrinol. Metab. Clin. North Am. 43:949-962.
Kuiper et al. (May 2015) "Statin use and low density lipoprotein cholesterol goal attainment among a high cardiovascular risk population in the Netherlands," Pharmo ISA Poster.
Lamon-Fava et al. (Apr. 7, 2011) "Lipoprotein(a) levels, apo(a) isoform size, and coronary heart disease risk in the Framingham Offspring Study," J. Lipid Res. 52:1181-1187.
Roth et al. (May 23-26, 2015) "Phase 3 Randomized Trial Evaluating Alirocumab Every Four Weeks Dosing as Add-on to Statin or as Monotherapy: ODYSSEY Choice I," International Symposium on Atherosclerosis. Abstract No. 254.
Stroes et al. (Jun. 17, 2014) "Anti-PCSK9 Antibody Effectively Lowers Cholesterol in Patients With Statin Intolerance," J. Am. Coll. Cardiol. 63(23):2541-2548.
Tsimikas et al. (Jul. 22, 2015) "Antisense therapy targeting apolipoprotein(a): A randomised double-blind, placebo-controlled phase 1 study," Lancet. 386:1472-1483.
International Preliminary Report on Patentability corresponding to International Patent Application No. PCT/EP2012/051320, dated Jul. 30, 2013, 17 pages.
International Search Report with Written Opinion corresponding to International Patent Application No. PCT/EP2012/057890, dated Aug. 28, 2012, 14 pages.
International Search Report with Written Opinion corresponding to International Patent Application No. PCT/US2015/040754, dated Oct. 14, 2015, 15 pages.
International Search Report with Written Opinion corresponding to International Patent Application No. PCT/US2015/040765, dated Nov. 26, 2015, 15 pages.
Third Party Observations corresponding to European Patent Application No. 12761864.3, dated Feb. 24, 2016, 9 pages.
Horton et al. (2007) "Molecular biology of PCSK9: its role in LDL metabolism," Trends Biochem Sci. 32(2): 71-77.
Hovingh et al. (Feb. 13, 2013) "Diagnosis and treatment of familial hypercholesterolaemia," Eur Heart J. 34(13):962-971.
Huang et al. (May 2015) "Clinical characteristics and unmet need among real-world atherosclerotic cardiovascular disease (ASCVD) patients stratified by statin use," J Clin Lipidol. 9(3):437-438. Abstract 134.
Huston et al. (1988) "Protein engineering of antibody binding sites: recovery of specific activity in an anti-digoxin single-chain Fv analogue produced in *Escherichia coli*," Proceedings of the National Academy of Sciences USA. 85(16):5879-5883.
Igawa et al. (2010) "Antibody recycling by engineered pH-dependent antigen binding improves the duration of antigen neutralization," Nature Biotechnology. 28(11):1203-1208.
Ito et al. (1992) "The His-probe method: effects of histidine residues introduced into the complementarity-determining regions of antibodies on antigen-antibody interactions at different pH values," Federation of European Biochemical Societies. 309(1):85-88.
Jones et al. (2015) "Pooled safety and adverse events in nine randomized, placebo-controlled, phase 2 and 3 clinical trials of alirocumab," J Am Coll Cardiol. 65(10_S):A1363.
Jorgensen et al. (Dec. 17, 2012) "Genetically elevated non-fasting triglycerides and calculated remnant cholesterol as casual risk factors for myocardial infarction," European Heart Journal 34:1826-1833.
Junghans et al. (1990) "Anti-Tac-H, a Humanized Antibody to the Interleukin 2 Receptor with New Features for Immunotherapy in Malignant and Immune Disorders," Cancer Research. 50:1495-1502.
Kastelein et al. (Aug. 31, 2014) "Efficacy and Safety of Alirocumab in Patients with Heterozygous Familial Hypercholesterolemia not Adequately Controlled with Current Lipid-Lowering Therapy: Results of ODYSSEY FH I and FH II Studies," Poster Presented at the ECS Congress 2014. Barcelona, Spain.
Kastelein et al. (Jun. 2014) "Efficacy and Safety of Alirocumab in Patients with Heterozygous Familial Hypercholesterolemia not Adequately Controlled with Current Lipid-Lowering Therapy: Design and Rationale of the ODYSSEY FH Studies," Cardiovasc Drugs Ther. 28(3):281-289.
Kastelein et al. (Sep. 1, 2015) "ODYSSEY FH I and FH II: 78-week results with alirocumab treatment in 735 patients with heterozygous familial hypercholesterolemia," Eur Heart J. 36(43):2996-3003.
Kawashiri et al. (2012) "Statin Therapy Improves Fractional Catabolic Rate of LDL without Affecting Impaired VLDL and VLDL Remnant Catabolism in Homozygous FH Patient Due to PCSK9 Gene Mutation: Evidence from Kinetic Study with Stable Isotope," Circulation 126(21):A13869.
Kereiakes et al. (Dec. 2, 2014) "Efficacy and safety of alirocumab in high cardiovascular risk patients with suboptimally controlled hypercholesterolemia on maximally tolerated doses of statins: the ODYSSEY COMBO I study," Circulation. 130:2119-2120.
Kereiakes et al. (Mar. 13, 2015) "Efficacy and safety of the PCSK9 inhibitor alirocumab among high cardiovascular risk patients on maximally tolerated statin therapy: the ODYSSEY COMBO I study," Am Heart J. 169(6):906-915.
Koren et al. (2012) "Efficacy, safety and tolerability of 150 mg Q2W dose of the anti-PCSK9 mAb, REGN727/SAR236553: data from 3 phase 2 studies," Eur Heart J. 33(Abstract Supplement):37. Abstract 429.
Koren et al. (2014) "Effects of alirocumab, a fully human monoclonal antibody to proprotein convertase subtilisin/kexin type 9, on lipoprotein particle concentrations determined by nuclear magnetic resonance: substudy of a randomized double-blind phase II clinical trial," J Am Coll Cardiol. 63(12 Suppl 1):A1373.
Koren et al. (Jan. 22, 2015) "Safety and efficacy of alirocumab 150 mg every 2 weeks, a fully human proprotein convertase subtilisin/ kexin type 9 monoclonal antibody: a Phase II pooled analysis," Postgrad Med. 22:1-8.
Koren et al. (May 2013) "Efficacy, safety and tolerability of alirocumab 150 mg Q2W, a fully human PCSK9 monoclonal antibody: a pooled analysis of 352 patients from phase 2," J Clin Lipidol. 7(3):279-280. Abstract 172.
Krauss et al. (2014) "Alirocumab, a fully human monoclonal antibody to proprotein convertase subtilisin/kexin type 9, and its effects on lipoprotein subfractions determined by ion mobility," Circulation. 130:A15525.
Kuhnast et al. (2013) "PCSK-9 monoclonal antibody alirocumab dose-dependently decreases atherosclerosis development and enhances the effects of atorvastatin in APOE*3Leiden CETP mice," Circulation. 128:A15823.
Kuhnast et al. (Oct. 2014) "Alirocumab inhibits atherosclerosis, improves the plaque morphology, and enhances the effects of a statin," J Lipid Res. 55(10):2103-2112.
Lagace et al. (2006) "Secreted PCSK9 decreases the Number of LDL receptors in hepatocytes and in liver of parabiotic mice," J Clin Invest Am Soc Clin Invest. 116(11):2995-3005.
Lambert et al. (Jul. 17, 2012) "The PCSK9 decade," J Lipid Res. 53(12):2515-2524.
Lambert et al. (Nov. 24, 2014) "Normalization of Low-Density Lipoprotein Receptor Expression in Receptor Defective Homozygous Familial Hypercholesterolemia by Inhibition of PCSK9 With Alirocumab," J Am Coll Cardiol. 64(21):2299-2300.
Langer et al. (1974) Medical Applications of Controlled Release. CRC Press, Boca Raton, Florida. pp. 115-138.
Langer et al. (1990) "New methods of drug delivery," Science. 249(4976):1527-1533.
Leuenberger et al. (1996) "A Multilingual Glossary of Biotechnological Terms," Recueil des Travaux Chimiques des Pays Bas. 115(7):382.
Lippi et al. (2000) "Lipoprotein(a): from ancestral benefit to modern pathogen?" QJ Med 93:75-84.
Lopez (2008) "Inhibition of PCSK9 as a Novel Strategy for the Treatment of Hypercholesterolemia," Drug News & Perspectives Abstract. 21(6):323.
Lose et al. (Apr. 2013) "Evaluation of Proprotein Convertase Subtilisin/Kexin Type 9: Focus on Potential Clinical and Therapeu-

(56) References Cited

OTHER PUBLICATIONS tic Implications for Low-Density Lipoprotein Cholesterol Lowering," Pharmacotherapy: The Journal of Human Pharmacology and Drug Therapy 33(4):447-460.

Lunven et al. (2014) "A randomized study of the relative bioavailability, pharmacodynamics, and safety of alirocumab, a fully human monoclonal antibody to proprotein convertase subtilison/ kexin type 9, after single subcutaneous administration at three different injection sites in healthy subjects," J Am Coll Cardiol 63(12 Suppl 1):A1377.

Lunven et al. (Dec. 2014) "A randomized study of the relative pharmacokinetics, pharmacodynamics and safety of alirocumab, a fully human monoclonal antibody to PCSK9, after single subcutaneous administration at three different injection sites in healthy subjects," Cardiovasc Ther. 32(6):297-301.

Maeda et al. (2002)"pH-dependent receptor/ligand dissociation as a determining factor for intracellular sorting of ligands for epidermal growth factor receptors in rat hepatocytes," J. Controlled Release 82:71-82.

Marcovina et al. (1998) "Lipoprotein(a) as a Risk Factor for Coronary Artery Disease," the American Journal of Cardiology 82(12A):57U-66U.

Maxwell et al. (2004) "Adenoviral-mediated expression of Pcsk9 in mice results in a low-density lipoprotein receptor knockout phenotype," Proc. Natl. Acad. Sci. USA. 101(18):7100-7105.

McKenney et al. (Mar. 2012) "A randomized, double-blind, placebo-controlled trial of the safety and efficacy of a monoclonal antibody to proprotein convertase subtilisin/kexin type 9 serine protease, REGN727/SAR236553, in patients with primary hypercholesterolemia (NCT: 01288443)," Presented as a late-breaking oral presentation at the American College of Cardiology (ACC) Annual Scientific Session, Mar. 24-27, 2012, Chicago, Illinois, USA.

McKenney et al. (Mar. 28, 2012) "Safety and efficacy of a monoclonal antibody to proprotein convertase subtilisin/kexin type 9 serine protease, SAR236553/REGN727, in patients with primary hypercholesterolemia receiving ongoing stable atorvastatin therapy," J Am Coll Cardiol. 59(25):2344-2353.

Missouri DU Report (2003) "Statin Therapy" Drug Use Review Newsletter. 8(6) pp. 1-9.

Moriarty et al. (2014) "ODYSSEY Alternative: Efficacy and safety of the proprotein convertase subtilisin/kexin type 9 monoclonal antibody, alirocumab, versus ezetimibe, in patients with statin intolerance as defined by a placebo run-in and statin rechallenge arm," Circulation. 130:2108-2109.

Moriarty et al. (Aug. 1, 2013) "Homogeneity of treatment effect of REGN727/SAR236553, a fully human monoclonal antibody against PCSK9, in lowering LDL-C: data from three phase 2 studies," Eur Heart J. 34(Suppl 1):18. Abstract 142.

Moriarty et al. (Aug. 29, 2015) "Efficacy and safety of alirocumab versus ezetimibe in statin-intolerant patients, with a statin-rechallenge arm: The ODYSSEY Alternative randomized trial," J Clin Lipidol. 9(6):758-769.

Moriarty et al. (Sep. 19, 2014) "Efficacy and safety of alirocumab, a monoclonal antibody to PCSK9, in statin-intolerant patients: Design and rationale of ODYSSEY Alternative, a randomized Phase 3 trial," J Clin Lipidol. 8(6):554-561.

Nakasako et al. (1999) "The pH-dependent structural variation of complementarity-determining region H3 in the crystal structures of the Fv fragment from an anti-dansyl monoclonal antibody," J. Mol. Biol. 291:117-134.

Naureckiene et al. (2003) "Functional characterization of Narc 1, a novel proteinase related to proteinase K," Archives of Biochemistry and Biophysics 420:55-67.

Noguchi et al. (2010) "The E32K variant of PCSK9 exacerbates the phenotype of familial hypercholesterolemia by increasing PCSK9 function and concentration in the circulation," Atherosclerosis 210(1):166-172.

Nordestgaard et al. (2010) "Lipoprotein(s) as cardiovascular risk factor: current status," European Heart Journal 31:2844-2853.

Padlan et al. (1995) "Identification of specificity-determining residues in antibodies," the FASEB Journal. 9(1):133-139.

Parhofer (2011) "Lipoprotein(a): Medical Treatment Options for an Elusive Molecule," Current Pharmaceutical Design 17:871-876.

Park et al. (2004) "Lipids and Lipoproteins: Post-transcriptional Regulation of Low Density Lipoprotein Receptor Protein by Proprotein Convertase Subtilisin/Kexin Type 9a in Mouse Liver," J. Biol. Chem. 279: 50630-50638.

Abifadel et al. (2003) "Mutations in PCSK9 cause autosomal dominant hypercholesterolemia," Nature Genetics 34(2):154-156.

Abifadel et al. (2009) "Mutations and polymorphisms in the proprotein convertase subtilisin kexin 9 (PCSK9) gene in cholesterol metabolism and disease," Human Mutation 30(4):520-529.

Abifadel et al. (May 17, 2012) "Identification and characterization of new gain-of-function mutations in the PCSK9 gene responsible for autosomal dominant hypercholesterolemia" Atherosclerosis 223(2):394-400.

Alborn et al. (2007) "Serum proprotein convertase subtilisin Kexin type 9 is correlated directly with serum LDL cholesterol," Clinical Chemistry 53(10):1814-1819.

Almagro et al. (2008) "Humanization of antibodies," Frontiers in Bioscience. 13:1619-1633.

Al-Mashhadi et al. (Jan. 2, 2013) "Atherosclerosis: Familial hypercholesterolemia and atherosclerosis in clones minipigs created by DNA transposition of a human PCSK9 gain-of-function mutant," Science Translation Medicine. 5(166):44-53.

Altschul et al. (1990) "Basic local alignment search tool," Journal of Molecular Biology. 215(3):403-410.

Altschul et al. (1997) "Gapped BLAST and PSI-BLAST: a new generation of protein database search programs," Nucleic Acids Research. 25(17):3389-3402.

Amgen Inc. (May 27, 2010) "Ascending Multiple Dose Study to Evaluate the Safety, Tolerability, Pharmacokinetics and Pharmacodynamics of AMG 145 in Subjects With Hyperlipidemia on Stable Doses of a Statin," Accessible on the Internet at URL: URL:http://clinicaltrials.gov/ct2/show/nct01133522?term=amg+145 &rank=2. [Last Accessed Aug. 6, 2014].

Angal et al. (1993) "A single amino acid substitution abolishes the heterogeneity of chimeric mouse/human (IgG4) antibody," Molecular Immunology. 30(1):105-108.

Anonymous (Jun. 27, 2013) "Long-term Safety and Tolerability of Alirocumab SAR236553 (REGN727) in High Cardiovascular Risk Patients With Hypercholesterolemia Not Adequately Controlled With Their Lipid Modifying Therapy: A Randomized, Double-Blind, Placebo-Controlled Study," Archive from ClinicalTrials.gov for NCT01507831, 3 pages.

Anonymous (Mar. 11, 2014) "A Randomized, Double-Blind, Placebo-Controlled, Parallel Group Study to Evaluate the Effect of Alirocumab (SAR236553/REGN727) on the Occurrence of Cardiovascular Events in Patients Who Have Recently Experienced an Acute Coronary Syndrome," Archive from ClinicalTrials.gov for NCT01663402, 3 pages.

Attie et al. (2005) "Dual regulation of the LDL receptor—Some clarity and new questions," Cell Metabolism 5:290-292.

Bays et al. (2014) "PCSK9 Inhibitor Alirocumab as Add-on to Atorvastatin versus Other Lipid Treatment Strategies in Patients at High CVD Risk: ODYSSEY Options I," Circulation. 130:A16194.

Bays et al. (Dec. 2, 2014) "Efficacy and safety of combining alirocumab with atorvastatin or rosuvastatin versus statin intensification or adding ezetimibe in high cardiovascular risk patients: ODYSSEY Options I and II," Circulation. 130:2118-2119.

Bays et al. (May 2015) "Alirocumab treatment effect on non-HDL-C: pooled analyses of ten Phase 3 trials in the ODYSSEY program," J Clin Lipidol. 9(3):471-472. Abstract 183.

Benjannet et al. (2006) "The Proprotein Convertase (PC) PCSK9 Is Inactivated by Furin and/or PC5/6A," J. Biological Chemistry 281(41):30561-30572.

Bird et al. (1988) "Single-chain antigen-binding proteins," Science. 242(4877):423-426.

Blom et al. (May 8, 2014) "A 52-Week Placebo-Controlled Trial of Evolocumab in Hyperlipidemia," the New England Journal of Medicine. 370(19):1809-1819.

(56) References Cited

OTHER PUBLICATIONS

Cannon et al. (Feb. 16, 2015) "Efficacy and safety of alirocumab in high cardiovascular risk patients with inadequately controlled hypercholesterolaemia on maximally tolerated doses of statins: the ODYSSEY COMBO II randomized controlled trial," Eur Heart J. 36(19):1186-1194.
Catapano et al. (Feb. 8, 2013) "The safety of therapeutic monoclonal antibodies: implications for cardiovascular disease and targeting the PCSK9 pathway," Atherosclerosis. 228(1):18-28.
Chan et al. (2009) "A proprotein convertase subtilisin/kexin type 9 neutralizing antibody reduces serum cholesterol in mice and non-human primates," Proc. Natl. Acad. Sci. USA. 106(24):9820-9825.
Chaparro-Riggers et al. (Jan. 31, 2012) "Increasing serum half-life and extending cholesterol lowering in vivo by engineering antibody with pH-sensitive binding to PCSK9," J. Biological Chemistry 287(14):11090-11097.
Colhoun et al. (Sep. 20, 2014) "Efficacy and safety of alirocumab, a fully human PCSK9 monoclonal antibody, in high cardiovascular risk patients with poorly controlled hypercholesterolemia on maximally tolerated doses of statins: rationale and design of the ODYSSEY COMBO I and II trials," BMC Cardiovasc Disord. 14(1):121.
Costet (May 1, 2012) "PCSK9 inhibitors as LDL cholesterol-lowering agents: Rationale, concerns and preliminary outcomes," Drugs of the Future. 37(5):331-341.
Duff et al. (2009) "Antibody-mediated disruption of the interaction between PCSK9 and the low-density lipoprotein receptor," Biochem. J. 419(3):577-584.
Dufour et al. (2012) "Effect of REGN727/SAR236553 PCSK9 fully human monoclonal antibody in patients with elevated triglycerides/low high-density lipoprotein cholesterol: data from three phase 2 studies," Circulation. 126:A16127.
Dufour et al. (Sep. 30, 2014) "One year open-label treatment with alirocumab 150 mg every two weeks in heterozygous familial hypercholesterolemic patients," Can J Cardiol. 30(10 suppl):S338. Abstract 546.
Fallon et al. (2000) "Increased endosomal sorting of ligand to recycling enhances potency of an intereukin-2 analog," J. Biological Chemistry 275(10):6790-6797.
Farnier (2011) "The role of proprotein convertase subtilisin/kexin type 9 in hyperlipidemia: Focus on therapeutic implications," American Journal of Cardiovascular Drugs 11(3):145-152.
Farnier et al. (2014) "Relationship between alirocumab, PCSK9 and LDL-C levels: results from the ODYSSEY MONO Phase 3 trial of alirocumab 75 mg every 2 weeks," Atherosclerosis. 235(2):e34-e35. Abstract EAS-0758.
Fasano et al. (2008) "45 Activity of Gain-of-Function PCSK9 Mutants on LDLR Correlates with Total-Cholesterol Values in ADH patients," Nutrition Metabolism and Cardiovascular Diseases. 18(1):S46.
Foody et al. (2013) "Attainment of low-density lipoprotein cholesterol goals in patients at high cardiovascular risk: results from a managed care population study," Circulation. 128:A17254.
Foote et al. (1992) "Antibody Framework Residues Affecting the Conformation of the Hypervariable Loops," J. Mol. Biol. 224:487-499.
Gaudet et al. (2012) "Effect of SAR236553/REGN727 fully human monoclonal anti-proprotein convertase subtilisin/kexin type 9 antibody on plasma lipoprotein(a) concentrations: pooled analysis from three phase 2 studies (NCT:01266876; 01288469; 01288443)," Circulation. 126:A14725.
Gaudet et al. (Jun. 18, 2014) "Effect of Alirocumab, a Monoclonal Proprotein Convertase Subtilisin/Kexin 9 Antibody, on Lipoprotein(a) Concentrations (a Pooled Analysis of 150 mg Every 2 Weeks Dosing from Phase 2 Trials)," Am J Cardiol. 114(5):711-715.
Gaudet et al. (May 2013) "Alirocumab, a fully human monoclonal antibody to PCSK9, reduces high plasma Lp(a) concentration: pooled analysis of 352 patients from phase 2," J Clin Lipidol. 7(3):283-284. Abstract 178.
Ginsberg et al. (2014) "ODYSSEY High FH: efficacy and safety of alirocumab in patients with severe heterozygous familial hypercholesterolemia," Circulation. 130:2119.
Gonnet et al. (1992) "Exhaustive Matching of the Entire Protein Sequence Database," Science. 256:1443-1445.
Gorcyca et al. (May 2015) "Prevalence of atherosclerotic cardiovascular disease and diabetes in the United States," J Clin Lipidol. 9(3):424. Abstract 118.
Grozdanov et al. (2006) "Expression and localization of PCSK9 in rat hepatic cells," Biochem. Cell. Biol. 84:80-92.
Gusarova et al. (Dec. 18, 2012) "Reduction of LDL cholesterol by a monoclonal antibody to PCSK9 in rodents and nonhuman primates," Clin Lipidol. 7(6):737-743.
Gusarova et al. (Mar. 25-30, 2012) "Fully human antibody that blocks PCSK9 demonstrates reduction in LDL-C preclinically and in early clinical trials," Abstract of oral presentation at the Keystone Symposia on Molecular and Cellular Biology, Mar. 25-30, 2012, Montana, USA.
Haddley et al. (Apr. 1, 2013) "ALIROCUMAB Anti-Proprotein Convertase 9 (PCSK9) Mab Treatment of Hypercholesterolemia," Drugs of the Future. 38(4):215-216.
Heap et al. (2005) "Analysis of a 17-amino acid residue, virus-neutralizing microantibody," Journal of General Virology. 86(6):1791-1800.
Hochleitner et al. (2000) "Characterization of a discontinuous epitope of the human immunodeficiency virus ~HIV! core protein p24 by epitope excision and differential chemical modification followed by mass spectrometric peptide mapping analysis," Protein Science. 9:487-496.
Holliger et al. (1993) "'Diabodies': small bivalent and bispecific antibody fragments," Proceedings of the National Academy of Sciences USA. 90(14):6444-6448.
Hopkins et al. (2011) "Familial Hypercholesterolemias: Prevalence, genetics, diagnosis and screening recommendations from the National Lipid Association Expert Panel on Familial Hypercholesterolemia," Journal of Clinical Lipidology. 5(3):S9-S17.
Hopkins et al. (2013) "A randomized placebo-phase clinical trial with the monoclonal antibody alirocumab demonstrates reductions in low-density lipoprotein cholesterol in patients with proprotein convertase subtilisin/kexin type 9 gain-of-function mutations," Circulation. 128:A17156.
Hopkins et al. (Dec. 2015) "Characterization of Autosomal Dominant Hypercholesterolemia Caused by PCSK9 Gain of Function Mutations and its Specific Treatment with Alirocumab, a PCSK9 Monoclonal Antibody," Circ Cardiovasc Genet. 8(6):823-831.
Pearson (1994) "Using the FASTA program to search protein and DNA sequence databases," Computer Analysis of Sequence Data. 1994:307-331.
Pfizer Inc. (Nov. 3, 2012) "Safety and Tolerability of Multiple Doses of PF-04950615 (RN316) in Subjects With Hypercholesterolemia," Accessible on the Internet at URL:http://clinicaltrials.gov/ct2/show?term=rn316&rank=2.
Pordy et al. (May 2013) "Alirocumab, a fully human monoclonal antibody to proprotein convertase subtilisin/kexin type 9: therapeutic dosing in phase 3 studies," J Clin Lipidol. 7(3):279.
Powell et al. (1998) "Compendium of Excipients for Parenteral Formulations PDA," Journal of Pharmaceutical Science and Technology. 52(5):238-311.
Qiu et al. (2007) "Small antibody mimetics comprising two complementarity-determining regions and a framework region for tumor targeting," Nature Biotechnology. 25(8):921-929.
Ramanathan et al. (2013) "Role of alirocumab (proprotein convertase subtilisin/kexin type 9 antibody) on CD81 levels and hepatitis C virus entry into hepatocytes," Circulation. 128:A12052.
Rashid et al. (2005) "Decreased plasma cholesterol and hypersensitivity to statins in mice lacking Pcsk9," Proc. Natl. Acad. Sci. USA. 102(15):5374-5379.
Ray (Jan. 2015) "Alirocumab: an investigational treatment for hypercholesterolemia," Clin Lipidol. 10(1):9-12.
Ray et al. (2013) "Attainment of low-density lipoprotein cholesterol goals in patients at very high cardiovascular risk in the United Kingdom: results from a general practice population study," Value Health. 16(7):A513.
Reddy et al. (2000) "Elimination of Fc receptor-dependent effector functions of a modified IgG4 monoclonal antibody to human CD4," the Journal of Immunology. 164(4):1925-1933.

(56) References Cited

OTHER PUBLICATIONS

Reineke (2004) "Antibody epitope mapping using arrays of synthetic peptides," in; Antibody Engineering. Humana Press. pp. 443-463.
Rey et al. (2014) "Randomized, partial blind study of the pharmacodynamics, pharmacokinetics and safety of multiple subcutaneous doses of alirocumab, a fully human monoclonal antibody to proprotein convertase subtilisin/kexin type 9, administered every 4 weeks alone or in combination with ezetimibe or fenofibrate in healthy subjects," J Am Coll Cardiol. 63(12 Suppl 1):A1375.
Reyes-Soffer et al. (2015) "Abstract 129: Effects of a proprotein convertase subtilisin/kexin type 9 inhibitor, alirocumab, on lipid and lipoprotein metabolism in normal subjects," Arterioscler, Thromb Vasc Biol. 35:A129.
Rhainds et al. (Dec. 2012) "PCSK9 inhibition and LDL cholesterol lowering: the biology of an attractive therapeutic target and critical review of the latest clinical trials," Clinical Lipidology 7(6):621-640.
Robinson et al. (2014) "Long-term safety, tolerability and efficacy of alirocumab versus placebo in high cardiovascular risk patients: first results from the ODYSSEY Long Term study in 2,341 patients," Circulation. 130:2120.
Robinson et al. (2015) "Adverse events in patients with low-density lipoprotein cholesterol levels <25 or <15 mg/dL on at least two consecutive visits in fourteen randomized, controlled, clinical trials of alirocumab," J Am Coll Cardiol. 65(10_S):A1350.
Robinson et al. (Apr. 16, 2015) "ODYSSEY Long Term Investigators. Efficacy and Safety of Alirocumab in Reducing Lipids and Cardiovascular Events.," N Eng J Med. 372:1489-1499.
Robinson et al. (Aug. 31, 2014) "Long-term safety, tolerability and efficacy of alirocumab versus placebo in high cardiovascular risk patients: first results from the ODYSSEY Long Term study in 2,341 patients," Highlights Presented at ESC Congress Aug. 31, 2014, Barcelona Spain.
Robinson et al. (Sep. 30, 2014) "Efficacy and safety of alirocumab as add-on therapy in high-cardiovascular-risk patients with hypercholesterolemia not adequately controlled with atorvastatin (20 or 40 mg) or rosuvastatin (10 or 20mg): design and rationale of the ODYSSEY Options studies," Clin Cardiol. 37(10):597-604.
Roth et al. (Apr. 2014) "A 24-week study of alirocumab monotherapy versus ezetimibe: The first phase 3 data of a proprotein convertase subtilisin/kexin type 9 inhibitor," J Am Coll Cardiol. 63(12_S):A1370.
Roth et al. (Jan. 2015) "ODYSSEY MONO: effect of alirocumab 75 mg subcutaneously every 2 weeks as monotherapy versus ezetimibe over 24 weeks," Future Cardiol. 11(1):27-37.
Roth et al. (Jul. 2, 2014) "Monotherapy with the PCSK9 inhibitor alirocumab versus ezetimibe in patients with hypercholesterolemia: Results of a 24 week, double-blind, randomized Phase 3 trial," Int J Cardiol. 176(1):55-61.
Roth et al. (Mar. 2014) "Alirocumab for hyperlipidemia: physiology of PCSK9 inhibition, pharmacodynamics and Phase I and II clinical trial results of a PCSK9 monoclonal antibody," Future Cardiology. 10(2):183-199.
Roth et al. (Mar. 27, 2012) "The effects of co-administering a monoclonal antibody to proprotein convertase subtilisin/kexin type 9 serine protease, REGN727/SAR236553, with 10 and 80 mg atorvastatin compared to 80 mg atorvastatin alone in patients with primary hypercholesterolemia (NCT: 01288469)," J Am Coll Cardiol. 59:E1620.
Roth et al. (May 2015) "Patient and physician perspectives on administration of the PCSK9 monoclonal antibody alirocumab, an injectable medication to lower LDL-C levels," J. Clin. Lipidol. 37(9):1945-1954.
Roth et al. (Nov. 15, 2012) "Atorvastatin with or without an antibody to PCSK9 in primary hypercholesterolemia," N Engl J Med. 367(20):1891-1900.
Sarkar et al. (2002) "Rational cytokine design for increased lifetime and enhanced potency using pH-activated histidine switching," Nature Biotechnology 20:908-913.
Schwartz et al. (Aug. 7, 2014) "Effect of alirocumab, a monoclonal antibody to pcsk9, on long-term cardiovascular outcomes following acute coronary syndromes: Rationale and design of the odyssey outcomes trial" Am Heart J. 168(5):682-689.
Sefton (1986) "Implantable Pumps," Critical Reviews in Biomedical Engineering. 14(3):201-240.
Seidah et al. (2003) "The secretory proprotein convertase neural apoptosis-regulated convertase 1 (NARC-1): liver regeneration and neuronal differentiation," Proc. Natl. Acad. Sci. USA. 100(3):928-933.
Shao (Apr. 26, 2014) "New Therapies for Lowering LDL-C: Targeting PCSK9," Abstract of oral presentation at the Sino-American Pharmaceutical Professionals Association—2014 Scientific Symposium, Apr. 26, 2014, New Jersey, USA.
Shields et al. (2002) "Lack of fucose on human IgG1 N-linked oligosaccharide improves binding to human FcγRIII and antibody-dependent cellular toxicity," Journal of Biological Chemistry. 277(30):26733-26740.
Soutar (2011) "Unexpected Roles for PCSK9 in Lipid Metabolism," Current Opinion in Lipodology. 22:192-196.
Stahl (Jul. 15, 2010) "Early Clinical Development #1 REGN727: anti-PCSK9," Regeneron Pharmaceuticals. Accessible on the Internet at URL: http://files.shareholder.com/downloads/REGN/0x0x387214/534aaeb6-5e66-4e8f-86a9-0f9cac20d72f/REGN%20Investor%20Day%20Early%20Clinical%20Development1.pdf.
Steen et al. (2014) "Attainment of Lipid Levels in Patients at High Cardiovascular Risk: Results from a U.S. Managed Care Population Study," Circulation. 130:A19949.
Steen et al. (Mar. 2015) "Cardiovascular Event Rates in a High-Risk Managed Care Population in the United States," J Am Coll Cardiol. 65(10_S):A1647.
Stein et al. (Jul. 2012) "Effect of a monoclonal antibody to PCSK9 on LDL cholesterol," Obstetrical and Gynecological Survey. 67(7):413-414.
Stein et al. (Mar. 2013) "Potential of proprotein Convertase Subtilisin/Kexin Type 9 Based Therapeutics," Current Atherosclerosis Reports. 15(310) pp. 1-14.
Stein et al. (Mar. 22, 2012) "Effect of a monoclonal antibody to PCSK9 on LDL cholesterol," N Engl J Med 366(12):1108-1118.
Stein et al. (Mar. 25-28, 2012) "Safety and efficacy of a monoclonal antibody to PCSK9, REGN727/SAR236553, in statin-treated heterozygous familial hypercholesterolemia patients," Presented as an oral presentation at the 80th European Atherosclerosis Society (EAS) Congress, May 25-28, 2012, Milan, Italy. Abstract 1398.
Stein et al. (Mar. 30, 2014) "One year open-label treatment with alirocumab 150 mg every two weeks in heterozygous familial hypercholesterolemic patients," J Am Coll Cardiol. 63(12 Suppl 1):A1371.
Stein et al. (May 26, 2012) "Effect of a monoclonal antibody to PCSK9, REGN727/SAR236553, to reduce low-density lipoprotein cholesterol in patients with heterozygous familial hypercholesterolaemia on stable statin dose with or without ezetimibe therapy: a phase 2 randomised controlled trial," Lancet. 380(9836):29-36.
Stroes et al. (Mar. 17, 2015) "Efficacy and safety of different dosing regimens of alirocumab (starting doses of 75 mg every two weeks and 150 mg every four weeks) versus placebo in patients with hypercholesterolemia not treated using statins: the ODYSSEY Choice II study," J Am Coll Cardiol. 65(10_S):A1370.
Sullivan et al. (Dec. 19, 2012) "Effect of a Monoclonal Antibody to PCSK9 on Low-Density Lipoprotein Cholesterol Levels in Statin-Intolerant Patients," JAMA. 308(23):2497-2506.
Swergold et al. (2010) "Safety, lipid, and lipoprotein effects of REGN727/SAR236553, a fully human proprotein convertase subtilisin kexin 9 (PCSK9) neutralizing monoclonal antibody administered intravenously to healthy volunteers," Circulation. 122:A23251.
Swergold et al. (2011) "Inhibition of proprotein convertase subtilisin/kexin type 9 with a monoclonal antibody REGN727/SAR236553, effectively reduces low-density-lipoprotein cholesterol, as mono or add-on therapy in heterozygous familial and non-familial hypercholesterolemia," Circulation 124:A16265.
Swergold et al. (2011) "REGN727/SAR236553, a fully human proprotein convertase subtilisin kexin 9 (PCSK9) monoclonal anti-

(56) References Cited

OTHER PUBLICATIONS body: effects on safety and lipid and lipoprotein profiles when administered subcutaneously," J Am Coll Cardiol. 57(14):E2023.
Swergold et al. (2011) "REGN727/SAR236553, a fully-human monoclonal antibody to proprotein convertase subtilisin kexin 9 (PCSK9), decreases ApoB and non-HDL-C when administered intravenously to healthy volunteers," J Clin Lipidol. 5(3):219. Abstract 135.
Swergold et al. (Oct. 22-26, 2013) "Identification and characterization of patients with autosomal dominant hypercholesterolemia caused by gain-of-function mutations in proprotein convertase subtilisin/kexin type 9 and comparison with patients with Familial Hypercholesterolemia (FH) and Familial Defective apolipoprotein B (FDB)," Abstract of a poster presentation at the American Society of Human Genetics (ASHG), Oct. 22-26, 2013, Boston, USA.
International Search Report with Written Opinion corresponding to International Patent Application No. PCT/US2014/060109, dated Apr. 16, 2015.
International Search Report with Written Opinion corresponding to International Patent Application No. PCT/US2014/065149, dated Feb. 3, 2015.
International Search Report with Written Opinion corresponding to International Patent Application No. PCT/US2015/015633, dated Aug. 19, 2015.
International Search Report with Written Opinion corresponding to International Patent Application No. PCT/US2015/020564, dated Jun. 12, 2015.
Office Action corresponding to Chinese Patent Application No. 201280015477.6, dated Dec. 2, 2014—with English summary.
Office Action corresponding to Chinese Patent Application No. 201280015571.1, dated Sep. 3, 2014—with English summary.
Office Action corresponding to European Patent Application No. 12701015.5, dated Apr. 24, 2015.
Office Action corresponding to European Patent Application No. 12701015.5, dated May 30, 2014.
Office Action corresponding to European Patent Application No. 12701742.4, dated Jun. 1, 2015.
Office Action corresponding to European Patent Application No. 12701742.4, dated May 28, 2014.
Partial International Search Report corresponding to International Patent Application No. PCT/US2014/040163, dated Nov. 6, 2014.
Teramoto et al. (2014) "Efficacy and safety of alirocumab in Japanese patients with hypercholesterolemia on stable statin therapy: first data with the 75 mg every two weeks dose," Circulation. 130:A13651.
Timms et al. (2004) "A mutation in PCSK9 causing autosomal-dominant hypercholesterolemia in a Utah pedigree," Human Genetics 114(4):349-353.
Tiwari et al. (2011) "Statins therapy: a review on conventional and novel formulation approaches," Journal of Pharmacy and Pharmacology. 63(8):983-998.
Toth et al. (2013) "Alirocumab, a proprotein convertase subtilisin/kexin type 9 monoclonal antibody, reduces cholesterol concentrations of all serum low-density lipoprotein cholesterol fractions," Circulation. 128:A17313.
Toth et al. (2013) "Alirocumab, a proprotein convertase subtilisin/kexin type 9 monoclonal antibody, reduces cholesterol concentrations of serum remnant lipoprotein fractions, very low-density lipoproteins and triglycerides," Circulation. 128:A17492.
Toth et al. (2014) "Proprotein convertase subtilisin/kexin 9 monoclonal antibody therapy significantly reduces apoprotein CII and CIII levels in serum," Atherosclerosis. 235(2):e107-e108. Abstract EAS-0750.
Tutt et al. (1991) "Trispecific F (alp') 3 derivatives that use cooperative signaling via the TCR/CD3 complex and CD2 to activate and redirect resting cytotoxic T cells," the Journal of Immunology. 147(1):60-69.

Vajdos et al. (2002) "Comprehensive functional maps of the antigen-binding site of an anti-ErbB2 antibody obtained with shotgun scanning mutagenesis," Journal of Molecular Biology. 320(2):415-428.
Van Der Hoorn et al. (2014) "Alirocumab, a monoclonal antibody to PCSK-9, dose-dependently decreases atherosclerosis, improves plaque stability and shows additive effects with atorvastatin in APOE*3Leiden.CETP mice," Atherosclerosis. 235(2):e19. Abstract WS16.
Varbo et al. (2013) "Remnant Cholesterol as a Casual Risk Factor for Ischemic Heart Disease" Journal of the American College of Cardiology 61(4):427-436.
Ward et al. (1989) "Binding activities of a repertoire of single immunoglobulin variable domains secreted from *Escherichia coli*," Nature. 341(6242):544-546.
Watanabe et al. (2009) "Optimizing pH response of affinity between protein G and IgG Fc," J. Biological Chemistry 284(18):12373-12383.
Westerterp et al. (2006) "Cholesteryl Ester Transfer Protein Decreases High-Density Lipoprotein and Severely Aggravates Atherosclerosis in APOE*3-Leiden Mice," Arterioscler Thromb. Vasc. Biol. Nov. 2006; 26(11):2552-2559.
Winter et al. (1993) "Humanized Antibodies," Immunology Today 14(6):243-246.
Wong et al. (May 1-4, 2014) "Residual Dyslipidemia According to LDL-C, non-HDL-C and Apolipoprotein B by Cardiovascular Risk Category in Statin Treated US Adults," J Clin Lipidol. 8:323-324. Presented as a poster presentation at the National Lipid Association Scientific Sessions, May 1-4, 2014, Orlando, Florida, USA.
Wu et al. (1987) "Receptor-mediated in vitro gene transformation by a soluble DNA carrier system," Journal of Biological Chemistry. 262(10):4429-4432.
Annex to Form PCT/ISA/206—Communication Relating to the Results of the Partial International Search corresponding to International Patent Application No. PCT/US2009/068013, dated Mar. 10, 2010.
International Preliminary Report on Patentability corresponding to International Patent Application No. PCT/EP2012/051321, dated Jul. 30, 2013.
International Search Report with Written Opinion corresponding to International Patent Application No. PCT/EP2012/051320, dated Sep. 21, 2012.
International Search Report with Written Opinion corresponding to International Patent Application No. PCT/EP2012/051321, dated Apr. 19, 2012.
International Search Report with Written Opinion corresponding to International Patent Application No. PCT/EP2015/055369, dated May 21, 2015.
International Search Report with Written Opinion corresponding to International Patent Application No. PCT/US2014/041204, dated Oct. 17, 2014.
Taylor et al. (1992) "A transgenic mouse that expresses a diversity of human sequence heavy and light chain immunoglobulins," Nucleic Acids Research, 20(23):6287-6295.
Verschuren et al. (2005) "Effect of Low Dose Atorvastatin Versus Diet-Induced Cholesterol Lowering on Atherosclerotic Lesion Progression and Inflammation in Apolipoprotein E*3-Leiden Transgenic Mice," Arterioscler Thromb Vasc. Biol., 25:161-167.
Kuhnast et al. (2012) "Aliskiren Inhibits Atherosclerosis Development and Imrpoves Plaque Stability in APOE*3Leiden.CETP Transgenic Mice with or without Treatment with Atorvastatin," J. Hypertens, 30(1):21-41.
Stary et al. (1995) "A Definition of Advanced Types of Atherosclerotic Lesions and a Histological Classification of Atherosclerosis," Arterioscler Thromb Vase Biol., vol. 15, 47 pages.
Kuhnast et al. (2013) "Niacin Reduces Atherosclerosis Development in APOE*3Leiden.CETP Mice Mainly by Reducing NonHDL-Cholesterol," PLOS One, 8(6):e66467, 13 pages.
Post et al. (1999) "Acyl-Coenzyne A:Cholesterol Acyltransferase Inhibitor, Avasimibe, Stimulates Bile Acid Synthesis and Cholesterol 7α-Hydroxylase in Cultured Rat Hepatocytes and in Vitro in the Rat," Hepatology, 30(2):491-500.

(56) References Cited

OTHER PUBLICATIONS

Post et al. (2003) "Increased Fecal Bile Acid Excretion in Transgenic Mice With Elevated Expression of Human Phospholipid Transfer Protein," Arterioscler Thromb Vasc Biol., 23:892-897.

Sanofi and Regeneron Report Positive Top-line Results with Alirocumab from First Phase 3 Study of a PCSK9 Inhibitor for LDL Cholesterol Reduction, Oct. 16, 2013, Retrieved from the Internet, [Last accessed Dec. 4, 2018: http://www.epresspack.net/mmr/sanofi-pcsk9-1st-phase3-results/].

Sanofi and Regeneron Announce Collaboration with American College of Cardiology for PCSK9 Inhibitor Clinical Program, Dec. 19, 2013, Retrieved from the Internet, [Last accessed Dec. 4, 2018: https://newsroom.regeneron.com/news-releases/news-release-details/sanofi-and-regeneron-announce-collaboration-american-college].

Steinberg et al. (2009) "Inhibition of PCSK9: A powerful weapon for achieving ideal LDL cholesterol levels," Proceedings of the National Academy of Sciences USA. 106(24):9546-9547.

Australian Public Assessment Report for Alirocumab (rch) (2016) Australian Government Department of Health, Therapeutic Goods Administration. Sponsor: Sanofi-Aventis Australia Pty Ltd, 93 pages.

Ni et al. (2010) "A proprotein convertase subtilisin-like/kexin type 9 (PCSK9) C-terminal domain antibody antigen-binding fragment inhibits PCSK9 internalization and restores low density lipoprotein uptake," J Biol Chem. 285(17):12882-91.

\* cited by examiner

METHODS FOR INHIBITING ATHEROSCLEROSIS BY ADMINISTERING AN ANTI-PCSK9 ANTIBODY

RELATED APPLICATIONS

This application is a continuation of U.S. patent application Ser. No. 15/874,807, filed Jan. 18, 2018, which is a continuation of U.S. patent application Ser. No. 14/896,196, filed Dec. 4, 2015, which is a 35 U.S.C. § 371 filing of International Patent Application No. PCT/US2014/041204, filed Jun. 6, 2014, which claims the benefit of priority to U.S. Provisional Application No. 61/832,459, filed Jun. 7, 2013; European Patent Application No. 13305762.0, filed Jun. 7, 2013; U.S. Provisional Application No. 61/892,215, filed Oct. 17, 2013; European Patent Application No. 13306436.0, filed Oct. 18, 2013; U.S. Provisional Application No. 61/944,855, filed Feb. 26, 2014; and U.S. Provisional Application No. 62/002,508, filed May 23, 2014. The content of each of the aforementioned applications is hereby incorporated by reference in their entirety.

FIELD OF THE INVENTION

The present invention relates to the field of therapeutic treatments for atherosclerosis. More specifically, the invention relates to the administration of proprotein convertase subtilisin/kexin type 9 (PCSK9) inhibitors to inhibit atherosclerotic plaque formation in a subject.

BACKGROUND

Atherosclerosis represents the major cause of death and cardiovascular morbidity in the western world. Risk factors for atherosclerosis include high low density lipoprotein (LDL) cholesterol levels, low high density lipoprotein (HDL) cholesterol levels, hypertension, diabetes mellitus, family history, male gender, cigarette smoke, and high serum cholesterol.

Proprotein convertase subtilisin/kexin type 9 (PCSK9) is a proprotein convertase belonging to the proteinase K subfamily of the secretory subtilase family. It is a serine protease involved in LDL metabolism that is mainly expressed in the liver, kidney, and intestines. Evidence suggests that PCSK9 increases plasma LDL cholesterol by promoting degradation of the LDL receptor, which mediates LDL endocytosis in the liver, the major route of LDL clearance from circulation.

The use of PCSK9 inhibitors (anti-PCSK9 antibodies) to reduce serum total cholesterol, LDL cholesterol and serum triglycerides have been described in U.S. Pat. Nos. 8,062,640, 8,357,371, and US Patent Application Publication No. 2013/0064834. Nonetheless, PCSK9 inhibitors have not been reported to reduce or inhibit progression of atherosclerotic plaque formation in a subject. There remains a need in the art for therapeutic methods of inhibiting atherosclerotic plaque formation.

BRIEF SUMMARY OF THE INVENTION

The present invention addresses the need in the art for therapeutic methods by providing methods and compositions for inhibiting atherosclerotic plaque formation in a subject. In certain aspects, the methods and compositions of the present invention generally comprise selecting a subject who has, or is at risk of developing, atherosclerosis, and administering to the subject a pharmaceutical composition comprising a proprotein convertase subtilisin/kexin type 9 (PCSK9) inhibitor (e.g., an anti-PCSK9 antibody or antigen binding protein). In other aspects, the invention provides a pharmaceutical composition comprising a PCSK9 inhibitor for use in the inhibition of atherosclerotic plaque formation in a subject. In yet other aspects, the invention provides a method of inhibiting atherosclerotic plaque formation in a subject by administering to the subject a pharmaceutical composition comprising a PCSK9 inhibitor.

In certain embodiments, the subject is nonhyperlipidemic. In other embodiments, the subject is apparently healthy.

In another aspect, the invention provides a method of treating or inhibiting progression of atherosclerosis in a subject, the method comprising: (a) selecting a subject who has suffered a stroke or myocardial infarction; and (b) administering to the subject a pharmaceutical composition comprising a PCSK9 inhibitor, thereby treating or inhibiting progression of atherosclerosis. In one embodiment, the subject is nonhyperlipidemic.

In another aspect, the invention provides a pharmaceutical composition comprising a PCSK9 inhibitor for use in treating or inhibiting progression of atherosclerosis in a subject who has suffered a stroke or myocardial infarction.

In another aspect, the invention provides a method of treating or inhibiting progression of atherosclerosis in a nonhyperlipidemic subject, the method comprising (a) selecting a subject who has, or is known to be at risk of developing, atherosclerosis, wherein the subject is nonhyperlipidemic; and (b) administering to the subject a pharmaceutical composition comprising a PCSK9 inhibitor, thereby treating or inhibiting progression of atherosclerosis. In one embodiment, the subject is apparently healthy. In another embodiment, the subject is nonhypercholesterolemic. In another embodiment, the subject is nonhypertriglyceridemic.

In another aspect, the invention provides a pharmaceutical composition comprising a PCSK9 inhibitor for use in treating or inhibiting progression of atherosclerosis in a nonhyperlipidemic subject, wherein the subject has, or is known to be at risk of developing, atherosclerosis.

In certain embodiments, the subject has a disease or disorder selected from the group consisting of type I diabetes mellitus, type II diabetes mellitus, Kawasaki disease, chronic inflammatory disease, and hypertension. In another embodiment, the subject has elevated levels of an inflammatory marker. In a further embodiment, the inflammatory marker is C-reactive protein. In another further embodiment, the inflammatory marker is an inflammatory cytokine.

In certain exemplary embodiments, the PCSK9 inhibitor is an antibody, or antigen binding protein, that specifically binds to PCSK9. In other embodiments, the antibody comprises heavy and light chain CDR amino acid sequences having SEQ ID NOs 12, 13, 14, 16, 17, and 18. In certain embodiments, the antibody or antigen-binding protein comprises an HCVR having the amino acid sequence of SEQ ID NO:11 and an LCVR having the amino acid sequence of SEQ ID NO:15. In certain embodiments, the antibody or antigen-binding protein comprises heavy and light chain CDR amino acid sequences having SEQ ID NOs 2, 3, 4, 7, 8, and 10. In certain embodiments, the antibody or antigen-binding protein comprises an HCVR having the amino acid sequence of SEQ ID NO:1 and an LCVR having the amino acid sequence of SEQ ID NO:6. In one embodiment, the antibody or antigen-binding protein binds to the same epitope on PCSK9 as an antibody comprising the heavy and light variable domain amino acid sequences forth in SEQ ID NOs: 1 and 6; or 11 and 15, respectively. In some embodiments, the antibody or antigen-binding protein competes for binding to PCSK9 with an antibody comprising the heavy and light chain variable domain amino acid sequences forth in SEQ ID NOs: 1 and 6; or 11 and 15, respectively.

In another embodiment, the PCSK9 inhibitor reduces atherosclerotic plaque formation in the subject by at least 10%, 20%, 30%, 40%, 50%, 60%, 70%, 80%, or 90%.

In some embodiments, the subject has heterozygous Familial Hypercholesterolemia (heFH). In other embodiments, the subject has a form of hypercholesterolemia that is not Familial Hypercholesterolemia (nonFH).

In certain embodiments, the subject is on another lipid-modifying agent before and/or during administration of the antibody or antigen-binding protein. Therapeutic lipid-modifying agents include statins, cholesterol uptake inhibitors, ezetimibe, fibrates, niacin, omega-3 fatty acids, and bile acid resins. Statins include cerivastatin, atorvastatin, simvastatin, pitavastatin, rosuvastatin, fluvastatin, lovastatin and pravastatin.

In some embodiments, the antibody or antigen binding protein is administered subcutaneously.

The invention also provides a unit dosage form comprising the pharmaceutical compositions of PCSK9 inhibitors. In certain embodiments, the PCSK9 inhibitor is an antibody or antigen-binding fragment and the unit dosage form comprises 75 mg, 150 mg, 200 mg, or 300 mg of the antibody or antigen-binding fragment. The unit dosage form may be a pre-filled syringe, a pre-filled autoinjector, a vial, a cartridge, a reusable syringe, or a reusable autoinjector; the unit dosage form may be hermetically sealed, and may further indicate the dosage.

The invention also provides an article of manufacture or kit comprising the pharmaceutical composition of a PCSK9 inhibitor and a container, and in some embodiments also includes instructions for use.

The invention also provides a use of composition comprising a PCSK9 inhibitor in the manufacture of a medicament for: (a) inhibition of atherosclerotic plaque formation in a subject; (b) treating or inhibiting progression of atherosclerosis in a subject who has suffered a stroke or myocardial infarction; or (c) treating or inhibiting progression of atherosclerosis in a nonhyperlipidemic subject, wherein the subject has, or is known to be at risk of developing, atherosclerosis.

BRIEF DESCRIPTION OF THE DRAWINGS

FIG. 1A shows the effect on average plasma total cholesterol; FIG. 1B shows the effect on triglyceride levels. FIGS. 1C and 1D show the lipoprotein profiles for cholesterol as assessed by FPLC lipoprotein separation after 12 weeks of treatment to study the effects of mAb316P alone (FIG. 1C) and in combination with atorvastatin (FIG. 1O). ***$P<0.0045$ as compared to control; †††$P<0.0045$ as compared to atorvastatin; ‡‡‡$P<0.0045$ compared 3 mg/kg mAb316P to 10 mg/kg mAb316P (n=15 per group).

DETAILED DESCRIPTION

Figure 1A:
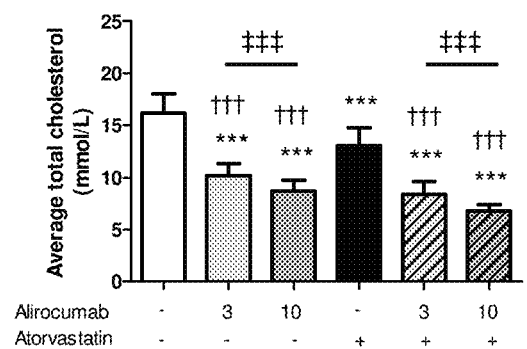
FIGS. 1A-D shows a series of graphs depicting the effect of mAb316P, atorvastatin, and their combination on several parameters after an 18 week treatment period.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, exemplary methods and materials are now described. All publications mentioned herein, and the sequence listing filed concurrently herewith, are incorporated herein by reference in their entirety.

Methods for Inhibiting Atherosclerosis

The methods of the present invention comprise selecting subjects that have, or are at risk of developing, atherosclerosis, and administering to these subjects a pharmaceutical composition comprising a PCSK9 inhibitor.

Risk factors for atherosclerosis are well known in the art and include, without limitation, high low density lipoprotein (LDL) cholesterol levels, low high density lipoprotein (HDL) cholesterol levels, hypertension, diabetes mellitus, family history, male gender, cigarette smoking, and high serum cholesterol. Methods of assessing these risk factors for a given subject are also well known in the art.

In certain embodiments, the selected subject is nonhyperlipidemic. A "non hyperlipidemic" is a subject that is a nonhypercholesterolemic and/or a nonhypertriglyceridemic subject. A "nonhypercholesterolemic" subject is one that does not fit the current criteria established for a hypercholesterolemic subject. A "nonhypertriglyceridemic" subject is one that does not fit the current criteria established for a hypertriglyceridemic subject (See, e.g., Harrison's Principles of Experimental Medicine, 13th Edition, McGraw-Hill, Inc., N.Y). A hypercholesterolemic subject has an LDL level of >160 mg/dL, or >130 mg/dL and at least two risk factors selected from the group consisting of male gender, family history of premature coronary heart disease, cigarette smoking (more than 10 per day), hypertension, low HDL (<35 mg/dL), diabetes mellitus, hyperinsulinemia, abdominal obesity, high lipoprotein (a), and personal history of cerebrovascular disease or occlusive peripheral vascular disease. A hypertriglyceridemic subject has a triglyceride (TG) level of >250 mg/dL. Thus, a nonhyperlipidemic subject is defined as one whose cholesterol and triglyceride levels are below the limits set as described above for both the hypercholesterolemic and hypertriglyceridemic subjects. In certain embodiments the selected subject is neither nonhyperlipidemic nor receiving treatment for hyperlipidemia.

In certain embodiments, the selected subject is apparently healthy. "Apparently healthy," as used herein, means individuals who have not previously had an acute, adverse cardiovascular event such as a myocardial infarction (i.e., individuals who are not at an elevated risk of a second adverse cardiovascular event due to a primary adverse cardiovascular event). Apparently healthy individuals also do not otherwise exhibit symptoms of disease.

In certain embodiments, the selected subject has previously suffered an acute adverse cardiovascular event such as a myocardial infarction, stroke, angina pectoris and/or peripheral arteriovascular disease. In one embodiment, the selected subject has previously suffered an acute adverse cardiovascular event such as a myocardial infarction, stroke, angina pectoris and/or peripheral arteriovascular disease, but is nonhyperlipidemic. In one embodiment, the selected subject has previously suffered an acute adverse cardiovascular event such as a myocardial infarction, stroke, angina pectoris and/or peripheral arteriovascular disease, but is neither nonhyperlipidemic nor receiving treatment for hyperlipidemia.

In certain embodiments, the selected subject has a disease or disorder selected from the group consisting of type I diabetes mellitus, type II diabetes mellitus, Kawasaki disease, chronic inflammatory disease, and hypertension. In one embodiment, the selected subject has a disease or disorder selected from the group consisting of type I diabetes mellitus, type II diabetes mellitus, Kawasaki disease, chronic inflammatory disease, and hypertension, but is nonhyperlipidemic. In one embodiment, the selected subject has a disease or disorder selected from the group consisting of type I diabetes mellitus, type II diabetes mellitus, Kawasaki disease, chronic inflammatory disease, and hypertension, but is neither nonhyperlipidemic nor receiving treatment for hyperlipidemia.

In certain embodiments, the selected subject has elevated levels of an inflammatory marker. In one embodiment, the selected subject has elevated levels of an inflammatory marker, but is nonhyperlipidemic. Any marker of systemic inflammation can be utilized for the purposes of the present invention. Suitable inflammatory markers include, without limitation, C-reactive protein (see e.g., U.S. Pat. No. 7,964,614, which is incorporated by reference herein in its entirety), cytokines (e.g., IL-6, IL-8, and/or IL-17), and cellular adhesion molecules (e.g., ICAM-1, ICAM-3, BL-CAM, LFA-2, VCAM-1, NCAM, and PECAM).

The level of an inflammatory marker can be obtained by any art-recognized assay. Typically, the level is determined by measuring the level of the marker in a body fluid, for example, blood, lymph, saliva, urine and the like. The level can be determined by ELISA, or immunoassays or other conventional techniques for determining the presence of the marker. To determine if levels of the inflammatory marker are elevated, the level of the marker measured in a subject can be compared to a suitable control (e.g., a predetermined value and/or a value obtained from a matched healthy subject).

In one embodiment, present invention provides a pharmaceutical composition comprising a PCSK9 inhibitor for use in the inhibition of atherosclerotic plaque formation in a subject, as well as in treating or inhibiting progression of atherosclerosis in a subject.

The present invention also provides uses of a pharmaceutical composition comprising a PCSK9 inhibitor for the manufacture of a medicament for any of the methods described herein, including inhibition of atherosclerotic plaque formation, and treating or inhibiting progression of atherosclerosis in a subject.

PCSK9 Inhibitors

In certain aspects, the methods of the present invention comprise administering to a subject a therapeutic composition comprising a PCSK9 inhibitor.

As used herein, a "PCSK9 inhibitor" is any agent which binds to or interacts with human PCSK9 and inhibits the normal biological function of PCSK9 in vitro or in vivo. Non-limiting examples of categories of PCSK9 inhibitors include small molecule PCSK9 antagonists, antagonistic nucleic acid molecules (e.g., RNAi molecules) peptide-based PCSK9 antagonists (e.g., "peptibody" molecules), and antibodies or antigen-binding fragments of antibodies that specifically bind human PCSK9.

As used herein, the term "proprotein convertase subtilisin/kexin type 9" or "PCSK9" refers to PCSK9 having the nucleic acid sequence shown in SEQ ID NO:197 and the amino acid sequence of SEQ ID NO:198, or a biologically active fragment thereof.

In certain embodiments, administration of the PCSK9 inhibitor reduces atherosclerotic plaque formation in the subject (e.g., a human subject) by at least 10% (e.g., 10% 20%, 30%, 40%, 50%, 60%, 70%, 80%, 90%, or 100%) relative to atherosclerotic plaque formation in an untreated subject.

In certain embodiments, the PCSK9 inhibitor is an antibody or antigen-binding protein that specifically binds to PCSK9. As used herein, the term "antibody" refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain (C $C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-PCSK9 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules and antigen-binding proteins. The terms "antigen-binding portion" of an antibody, "antigen-binding fragment" of an antibody, "antigen-binding protein," and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments or antigen-binding proteins include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expressions "antigen-binding fragment" and 'antigen-binding proteins" as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 6, 7, 8, 9, 10, 11, 12, 13, 14, 15, 20, 25, 30, 35, 40, 50, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (see e.g., Angal et al. (1993) Molecular Immunology 30:105) to levels typically observed using a human IgG1 hinge. The instant invention encompasses antibodies having one or more mutations in the hinge, CH2 or CH3 region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding protein forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" PCSK9, as used in the context of the present invention, includes antibodies that bind PCSK9 or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human PCSK9 can, however, have cross-reactivity to other antigens, such as PCSK9 molecules from other (non-human) species.

Exemplary, non-limiting, PCSK9 inhibitors are set forth herein and include for example, inhibitors described in US Patent Application Publication Nos. US20130115223, US20130071405, US20130064834, US20130064825, US20120122954, US20120015435, US20110313024, US 20110015252, US20110230542, US20110009628, and U.S. Ser. No. 61/682,349, which are each incorporated herein by reference in their entireties. In some embodiments, the PCSK9 inhibitor is an antibody, including an antibody having VH/VL sequences of Ab "LGT209" as described in International Publication No. WO2011/072263; an antibody having VH/VL sequences of Ab "L1L3" as described in International Publication No. WO2010/029513; an antibody having VH/VL sequences of Ab "5L1721H23_6L3" as described in International Publication No. WO2011/111007; an antibody having VH/VL sequences of Ab "5L1721H23_6L3H3" as described in International Publication No. WO2011/111007; an antibody having VH/VL sequences of Ab "31H4" as described in International Publication No. WO2009/026558; an antibody having VH/VL sequences of Ab "1B20" as described in US Patent Application Publication No. US 2009/0232795; an antibody having VH/VL sequences of Ab "21B12" described in US Patent Application Publication No. US 2009/0142352; an antibody having VH/VL sequences of Ab "508.20.28" as described in US Patent Application Publication No. US 2012/0195910; or an antibody having VH/VL sequences of Ab "508.20.33" as described in US Patent Application Publication No. US 2012/0195910.

Anti-PCSK9 antibodies useful in the methods and compositions of the present invention may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the VH and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-PCSK9 antibodies comprising variants of any of the HCVR, LCVR, and/or CDR amino acid sequences disclosed herein having one or more conservative substitutions. For example, the present invention includes the use of anti-PCSK9 antibodies having HCVR; LCVR; CDR; HCVR and LCVR; HCVR and CDR; LCVR and CDR; or HCVR, LCVR and CDR amino acid sequences with, e.g., 10 or fewer, 9 or fewer, 8 or fewer, 7 or fewer, 6 or fewer, 5 or fewer, 4 or fewer, 3 or fewer, 2 or fewer, or 1 conservative amino acid substitutions relative to any of the HCVR, LCVR, and/or CDR amino acid sequences disclosed herein. In certain embodiments, the substitutions are in CDR amino acid sequences, e.g. CDR1, CDR2 and/or CDR3. In other embodiments, other embodiments, the substitutions are in CDR3 amino acid sequences.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

According to certain embodiments, the anti-PCSK9 antibody used in the methods of the present invention is an antibody with pH-dependent binding characteristics. As used herein, the expression "pH-dependent binding" means that the antibody or antigen-binding protein exhibits "reduced binding to PCSK9 at acidic pH as compared to neutral pH" (for purposes of the present disclosure, both expressions may be used interchangeably). For the example, antibodies "with pH-dependent binding characteristics" includes antibodies and antigen-binding fragments thereof that bind PCSK9 with higher affinity at neutral pH than at acidic pH. In certain embodiments, the antibodies and antigen-binding fragments of the present invention bind PCSK9 with at least 3, 5, 10, 15, 20, 25, 30, 35, 40, 45, 50, 55, 60, 65, 70, 75, 80, 85, 90, 95, 100, or more times higher affinity at neutral pH than at acidic pH.

According to this aspect of the invention, the anti-PCSK9 antibodies with pH-dependent binding characteristics may possess one or more amino acid variations relative to the parental anti-PCSK9 antibody. For example, an anti-PCSK9 antibody with pH-dependent binding characteristics may contain one or more histidine substitutions or insertions, e.g., in one or more CDRs of a parental anti-PCSK9 antibody. Thus, according to certain embodiments of the present invention, methods are provided comprising administering an anti-PCSK9 antibody which comprises CDR amino acid sequences (e.g., heavy and light chain CDRs) which are identical to the CDR amino acid sequences of a parental anti-PCSK9 antibody, except for the substitution of one or more amino acids of one or more CDRs of the parental antibody with a histidine residue. The anti-PCSK9 antibodies with pH-dependent binding may possess, e.g., 1, 2, 3, 4, 5, 6, 7, 8, 9, or more histidine substitutions, either within a single CDR of a parental antibody or distributed throughout multiple (e.g., 2, 3, 4, 5, or 6) CDRs of a parental anti-PCSK9 antibody. For example, the present invention includes the use of anti-PCSK9 antibodies with pH-dependent binding comprising one or more histidine substitutions in HCDR1, one or more histidine substitutions in HCDR2, one or more histidine substitutions in HCDR3, one or more histidine substitutions in LCDR1, one or more histidine substitutions in LCDR2, and/or one or more histidine substitutions in LCDR3, of a parental anti-PCSK9 antibody.

As used herein, the expression "acidic pH" means a pH of 6.0 or less (e.g., less than about 6.0, less than about 5.5, less than about 5.0, etc.). The expression "acidic pH" includes pH values of about 6.0, 5.95, 5.90, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Preparation of Human Antibodies

Methods for generating human antibodies in transgenic mice are known in the art. Any such known methods can be used in the context of the present invention to make human antibodies that specifically bind to human PCSK9.

Using VELOCIMMUNE™ technology (see, for example, U.S. Pat. No. 6,596,541, Regeneron Pharmaceuticals) or any other known method for generating monoclonal antibodies, high affinity chimeric antibodies to PCSK9 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc., using standard procedures known to those skilled in the art. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies that can be used in the methods of the present invention possess high affinities, as described above, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Specific examples of human antibodies or antigen-binding fragments of antibodies that specifically bind PCSK9 which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence selected from the group consisting of SEQ ID NOs:1 and 11, or a substantially similar sequence thereof having at least 90%, at least 95%, at least 98% or at least 99% sequence identity. Alternatively, specific examples of human antibodies or antigen-binding fragments of antibodies that specifically bind PCSK9 which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence selected from the group consisting of SEQ ID NOs 37, 45, 53, 61, 69, 77, 85, 93, 101, 109, 117, 125, 133, 141, 149, 157, 165, 173, 181, and 189, or a substantially similar sequence thereof having at least 90%, at least 95%, at least 98% or at least 99% sequence identity. The antibody or antigen-binding fragment may comprise the three light chain CDRs (LCVR1, LCVR2, LCVR3) contained within a light chain variable region (LCVR) having an amino acid sequence selected from the group consisting of SEQ ID NOs 6 and 15, or a substantially similar sequence thereof having at least 90%, at least 95%, at least 98% or at least 99% sequence identity. Alternatively, the antibody or antigen-binding fragment may comprise the three light chain CDRs (LCVR1, LCVR2, LCVR3) contained within a light chain variable region (LCVR) having an amino acid sequence selected from the group consisting of SEQ ID NOs 41, 49, 57, 65, 73, 81, 89, 97, 105, 113, 121, 129, 137, 145, 153, 161, 169, 177, 185, and 193, or a substantially similar sequence thereof having at least 90%, at least 95%, at least 98% or at least 99% sequence identity.

Sequence identity between two amino acids sequences is determined over the entire length of the reference amino acid sequence, i.e. the amino acid sequence identified with a SEQ ID NO, using the best sequence alignment and/or over the region of the best sequence alignment between the two amino acid sequences, wherein the best sequence alignment can be obtained with art known tools, e.g. Align, using standard settings, preferably EMBOSS: needle, Matrix: Blosum62, Gap Open 10.0, Gap Extend 0.5.

In certain embodiments of the present invention, the antibody or antigen-binding protein comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs:1/6 and 11/15. Alternatively, in certain embodiments of the present invention, the antibody or antigen-binding protein comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs:37/41, 45/49, 53/57, 61/65, 69/73, 77/81, 85/89, 93/97, 101/105, 109/113, 117/121, 125/129, 133/137, 141/145, 149/153, 157/161, 165/169, 173/177, 181/185, and 189/193.

In certain embodiments of the present invention, the anti-PCSK9 antibody, or antigen-binding protein, that can be used in the methods of the present invention has HCDR1/HCDR2/HCDR3/LCDR1/LCDR2/LCDR3 amino acid sequences selected from SEQ ID NOs: 2/3/4/7/8/10 (mAb316P) and 12/13/14/16/17/18 (mAb300N) (See US Patent App. Publ No. 2010/0166768) and 12/13/14/16/17/18, wherein SEQ ID NO:16 comprises a substitution of histidine for leucine at amino acid residue 30 (L30H).

In certain embodiments of the present invention, the antibody or antigen-binding protein comprises HCVR/LCVR amino acid sequence pairs selected from the group consisting of SEQ ID NOs:1/6 and 11/15. In certain exemplary embodiments, the antibody or antigen-binding protein comprises an HCVR amino acid sequence of SEQ ID NO:1 and an LCVR amino acid sequence of SEQ ID NO:6. In certain exemplary embodiments, the antibody or antigen-binding protein comprises an HCVR amino acid sequence of SEQ ID NO:11 and an LCVR amino acid sequence of SEQ ID NO:15. In certain exemplary embodiments, the antibody or antigen-binding protein comprises an HCVR amino acid sequence of SEQ ID NO:11 and an LCVR amino acid sequence of SEQ ID NO:15 comprising a substitution of histidine for leucine at amino acid residue 30 (L30H).

In certain embodiments, the antibody or antigen-binding protein exhibits one or more or the following properties when administered by weekly subcutaneous injection to an APOE*3Leiden.CETP mouse:

a. reduces total cholesterol levels relative to untreated controls by about 37% when administered at 3 mg/kg;
b. reduces total cholesterol levels relative to untreated controls by about 46% when administered at 10 mg/kg;
c. reduces total cholesterol levels relative to untreated controls by about 48% when administered at 3 mg/kg in combination with 3.6 mg/kg/day atorvastin;
d. reduces total cholesterol levels relative to untreated controls by about 58% when administered at 10 mg/kg in combination with 3.6 mg/kg/day atorvastin;
e. reduces total cholesterol levels by about 36% when administered at 3 mg/kg in combination with 3.6 mg/kg/day atorvastin, relative to treatment with 3.6 mg/kg/day atorvastin alone;
f. reduces total cholesterol levels by about 48% when administered at 10 mg/kg in combination with 3.6 mg/kg/day atorvastin, relative to treatment with 3.6 mg/kg/day atorvastin alone;
g. reduces triglyceride levels relative to untreated controls by about 33% when administered at 3 mg/kg;
h. reduces triglyceride levels relative to untreated controls by about 36% when administered at 10 mg/kg;
i. reduces triglyceride levels by about 40% when administered at 3 mg/kg in combination with 3.6 mg/kg/day atorvastin, relative to treatment with 3.6 mg/kg/day atorvastin;
j. reduces triglyceride levels by about 51% when administered at 10 mg/kg in combination with 3.6 mg/kg/day atorvastin, relative to treatment with 3.6 mg/kg/day atorvastin alone;
k. increases hepatic LDLR expression relative to untreated controls by about 88% when administered at 3 mg/kg;
l. increases hepatic LDLR expression relative to untreated controls by about 178% when administered at 10 mg/kg;
m. increases hepatic LDLR expression by about 71% when administered at 3 mg/kg in combination with 3.6 mg/kg/day atorvastin, relative to treatment with 3.6 mg/kg/day atorvastin alone;
n. increases hepatic LDLR expression by about 140% when administered at 10 mg/kg in combination with 3.6 mg/kg/day atorvastin, relative to treatment with 3.6 mg/kg/day atorvastin alone;
o. decreases atherosclerotic lesion size relative to untreated controls by about 70% when administered at 3 mg/kg;
p. decreases atherosclerotic lesion size relative to untreated controls by about 87% when administered at 10 mg/kg;
q. decreases atherosclerotic lesion size relative to untreated controls by about 88% when administered at 3 mg/kg in combination with 3.6 mg/kg/day atorvastin;
r. decreases atherosclerotic lesion size relative to untreated controls by about 98% when administered at 10 mg/kg in combination with 3.6 mg/kg/day atorvastin;
s. decreases atherosclerotic lesion size relative by about 82% when administered at 3 mg/kg in combination with 3.6 mg/kg/day atorvastin, relative to treatment with 3.6 mg/kg/day atorvastin alone;
t. decreases atherosclerotic lesion size relative by about 97% when administered at 10 mg/kg in combination with 3.6 mg/kg/day atorvastin, relative to treatment with 3.6 mg/kg/day atorvastin alone;
u. reduces triglyceride levels by about 72% when administered at 3 mg/kg, relative to treatment with 3.6 mg/kg/day atorvastatin alone;
v. reduces triglyceride levels by about 79% when administered at 10 mg/kg, relative to treatment with 3.6 mg/kg/day atorvastatin alone;
w. reduces total cholesterol levels by about 22% when administered at 3 mg/kg, relative to treatment with 3.6 mg/kg/day atorvastatin alone;
x. reduces total cholesterol levels by about 34% when administered at 10 mg/kg, relative to treatment with 3.6 mg/kg/day atorvastatin alone;
y. increases the percentage of undiseased aortic segments by about 236% when administered at 3 mg/kg, relative to untreated control;
z. increases the percentage of undiseased aortic segments by about 549% when administered at 10 mg/kg, relative to untreated control;
aa. increases the percentage of undiseased aortic segments by about 607% when administered at 3 mg/kg in combination with 3.6 mg/kg/day atorvastatin, relative to control; and
bb. increases the percentage of undiseased aortic segments by about 1118% when administered at 3 mg/kg in combination with 3.6 mg/kg/day atorvastatin, relative to control.

Pharmaceutical Compositions and Methods of Administration

The present invention includes methods which comprise administering a PCSK9 inhibitor to a subject, wherein the PCSK9 inhibitor is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, inhalation, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, pen delivery devices and autoinjector delivery devices readily have applications in delivering a pharmaceutical composition of the present invention. Such delivery devices can be reusable or disposable, and can be adapted to administer a variable dose or a fixed dose. A reusable delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The delivery device can then be reused. In a disposable delivery device, there is no replaceable cartridge. Rather, the disposable delivery device comes pre-filled with the pharmaceutical composition held in a reservoir within the device. Once the reservoir is emptied of the pharmaceutical composition, the entire device is discarded. A delivery device adapted for variable dosing may include a mechanism for setting a dose within a range of dose volumes (in some cases, the range may be limited to a value less than a total volume contained in the cartridge). A delivery device adapted for fixed dosing may include a mechanism which delivers the total volume of the cartridge when the delivery device it actuated. In such cases, the cartridge may be a pre-filled syringe.

Numerous delivery devices have applications in the delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25$^1$m pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few. In some embodiments, the reusable pen or autoinjector delivers a fixed dose. In other embodiments, the reusable pen or autoinjector can deliver a variable dose. In different embodiments, the reusable pen or autoinjector can deliver a single dose or multiple doses.

In certain embodiments, the pharmaceutical composition is delivered in a controlled release system. In certain embodiments, a pump may be used (see Langer, supra; Sefton, 1987, CRC Crit. Ref. Biomed. Eng. 14:201), including a micropump. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil], etc. As the oily medium, there are employed, e.g., sesame oil, soybean oil, etc., which may be used in combination with a solubilizing agent such as benzyl benzoate, benzyl alcohol, etc. The injection thus prepared is filled in an appropriate ampoule.

Advantageously, the pharmaceutical compositions for oral or parenteral use described above are prepared into dosage forms in a unit dose suited to fit a dose of the active ingredients. As used herein, "unit dosage form" refers to physically discrete units suitable as single dosages for human and/or animal subjects, each unit containing a predetermined quantity of active material (i.e., a PCSK9 inhibitor) calculated to produce the desired therapeutic effect in association with a pharmaceutical diluent, carrier or vehicle. In some embodiments, the PCSK9 inhibitor is an antibody or antigen-binding protein and the unit dosage form comprises 75 mg, 150 mg, 200 mg, or 300 mg of the antibody or antigen-binding protein. Examples of suitable unit dosage forms for liquid pharmaceutical compositions include applicators such as vials, syringes, including pre-filled syringes and reusable syringes, autoinjectors, including pre-filled autoinjectors and reusable autoinjectors, cartridges, and ampules; other suitable unit dosage forms include tablets, pills, capsules, suppositories, wafers, segregated multiples of any of the foregoing, and other forms as herein described or generally known in the art. The unit dosage form may be hermetically sealed. For unit dosage forms containing the pharmaceutical composition within an applicator, the quantity of the PCSK9 inhibitor may be indicated on the applicator.

The present invention includes an article of manufacture or kit comprising (a) one or more unit dosage forms comprising a pharmaceutical composition of present invention, and (b) a container or package. The article of manufacture or kit can further comprise (c) a label or packaging insert with instructions for use. In some embodiments, the article of manufacture can further comprise (d) one or more unit dosage forms of a lipid-modifying therapy (e.g. a blister of tablets comprising as an active ingredient an HMG-CoA reductase inhibitor).

Dosage and Administration Regimens

The amount of PCSK9 inhibitor (e.g., anti-PCSK9 antibody) administered to a subject according to the methods and compositions of the present invention is, generally, a therapeutically effective amount. As used herein, the phrase "therapeutically effective amount" means a dose of PCSK9 inhibitor that results in a detectable reduction in atherosclerotic lesions. For example, "therapeutically effective amount" of a PCSK9 inhibitor includes, e.g., an amount of PCSK9 inhibitor that causes a reduction of at least 2%, 5%, 10%, 15%, 20%, 25%, 30%, 40%, 50%, 60%, 70%, 80%, 90% or more in sclerotic lesion area or lesion severity when administered to a human patient, e.g., as illustrated in the Examples herein. Alternatively, animal models can be used to establish whether a particular amount of a candidate PCSK9 inhibitor is a therapeutically effective amount.

In the case of an anti-PCSK9 antibody, a therapeutically effective amount can be from about 0.05 mg to about 600 mg, e.g., about 0.05 mg, about 0.1 mg, about 1.0 mg, about 1.5 mg, about 2.0 mg, about 3 mg, about 5 mg, about 10 mg, about 15 mg, about 20 mg, about 30 mg, about 40 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-PCSK9 antibody.

In certain embodiments, the anti-PCSK9 antibody is administered to a subject at a dose of 75 mg. In certain embodiments, the anti-PCSK9 antibody is administered to a subject at a dose of 150 mg. In certain embodiments, the anti-PCSK9 antibody is administered to a subject at a dose of 300 mg.

The amount of anti-PCSK9 antibody contained within the individual doses may be expressed in terms of milligrams of antibody per kilogram of patient body weight (i.e., mg/kg). For example, the anti-PCSK9 antibody may be administered to a patient at a dose of about 0.0001 to about 10 mg/kg of patient body weight.

According to certain embodiments of the present invention, multiple doses of a PCSK9 inhibitor may be administered to a subject over a defined time course. The methods according to this aspect of the invention comprise sequentially administering to a subject multiple doses of a PCSK9 inhibitor. As used herein, "sequentially administering" means that each dose of PCSK9 inhibitor is administered to the subject at a different point in time, e.g., on different days separated by a predetermined interval (e.g., hours, days, weeks or months). The present invention includes methods which comprise sequentially administering to the patient a single initial dose of a PCSK9 inhibitor, followed by one or more secondary doses of the PCSK9 inhibitor, and optionally followed by one or more tertiary doses of the PCSK9 inhibitor.

The terms "initial dose," "secondary doses," and "tertiary doses," refer to the temporal sequence of administration of the PCSK9 inhibitor. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. In certain embodiments, however, the amount of PCSK9 inhibitor contained in the initial, secondary and/or tertiary doses will vary from one another (e.g., adjusted up or down as appropriate) during the course of treatment. The initial, secondary, and tertiary doses may all contain the same amount of PCSK9 inhibitor.

In certain embodiments, each secondary and/or tertiary dose is administered 1 to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) days after the immediately preceding dose. The phrase "the immediately preceding dose," as used herein, means, in a sequence of multiple administrations, the dose of PCSK9 inhibitor which is administered to a patient prior to the administration of the very next dose in the sequence with no intervening doses.

In certain embodiments, the methods comprise administering to a patient any number of secondary and/or tertiary doses of a PCSK9 inhibitor. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 29 days after the immediately preceding dose. Similarly, in embodiments involving multiple tertiary doses, each tertiary dose may be administered at the same frequency as the other tertiary doses. For example, each tertiary dose may be administered to the patient 1 to 60 days after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In certain embodiments, the anti-PCSK9 antibody is administered to a subject at an initial dose of at about 75 mg every two weeks.

In additional embodiments, the antibody is administered to a subject at an initial dose of about 150 mg every two weeks.

In one embodiment, an initial dose is administered during an initial dosing period, after which the subject's LDL-C value is monitored determine if the initial dose should be changed to a secondary dose, by measuring the LDL-C value to determine if it is at or below a target LDL-C value. For example, a subject may begin treatment with an initial dose of 75 mg of the antibody, with a target LDL-C value of 100 milligrams per deciliter (mg/dL). If the subject's LDL-C reaches a target LDL-C value at the end of the initial dosing period, then the subject continues treatment on the initial dose, but changes to a secondary dose if that target value is not reached. In one embodiment, the initial dose is about 75 mg, administered every two weeks, the target LDL-C value is 100 mg/dL, and the secondary dose, if necessary, is 150 mg every two weeks. For example, the subject may be first monitored after about 8 weeks of treatment, and if their LDL-C value is above 100 mg/dL, the subject may be uptitrated to a secondary dose of 150 mg, administered every two weeks. Monitoring may continue throughout the treatment period. In another embodiment, the initial dose is 75 mg of antibody every two weeks, the target LDL-C value is 70 mg/dL, and the secondary dose is 150 mg every two weeks if the target LDL-C value is not reached.

Prior Therapies and Combination Therapies

The methods of the present invention, according to certain embodiments, comprise administering a pharmaceutical composition comprising an anti-PCSK9 antibody to a subject who is on a therapeutic regimen for the treatment of hypercholesterolemia and/or atherosclerosis at the time of, or just prior to, administration of the pharmaceutical composition of the invention. For example, a patient who has previously been diagnosed with hypercholesterolemia and/or atherosclerosis may have been prescribed and is taking a stable therapeutic regimen of another lipid modifying therapy prior to and/or concurrent with administration of a pharmaceutical composition comprising an anti-PCSK9 antibody. In other embodiments, the subject has not been previously treated with a lipid modifying therapy.

The methods of the present invention, according to certain embodiments, comprise administering as a monotherapy a pharmaceutical composition comprising an anti-PCSK9 antibody to a subject, in the absence of any concurrent lipid modifying therapy.

The methods of the present invention, according to certain embodiments, also comprise administering a pharmaceutical composition comprising an anti-PCSK9 inhibitor to a subject in combination with another lipid modifying therapy As used herein, lipid modifying therapies include, for example, (1) agents which induce a cellular depletion of cholesterol synthesis by inhibiting 3-hydroxy-3-methylglutaryl (HMG)-coenzyme A (CoA) reductase, such as a statin (e.g., cerivastatin, atorvastatin, simvastatin, pitavastatin, rosuvastatin, fluvastatin, lovastatin, pravastatin, etc.); (2) agents which inhibit cholesterol uptake and or bile acid re-absorption (such as ezetimibe); (3) agents which increase lipoprotein catabolism (such as niacin); and/or (4) activators of the LXR transcription factor that plays a role in cholesterol elimination such as 22-hydroxycholesterol. Lipid modifying therapies also include fixed combinations of therapeutic agents such as ezetimibe plus simvastatin; a statin with a bile resin (e.g., cholestyramine, colestipol, colesevelam); niacin plus a statin (e.g., niacin with lovastatin); or with other lipid lowering agents such as omega-3-fatty acid ethyl esters (for example, omacor).

EXAMPLES

The following examples are put forth so as to provide those of ordinary skill in the art with a complete disclosure and description of how to make and use the methods and compositions of the invention, and are not intended to limit the scope of what the inventors regard as their invention.

Example 1: Generation of Human Antibodies to Human PCSK9

Human anti-PCSK9 antibodies were generated as described in U.S. Pat. No. 8,062,640. The exemplary PCSK9 inhibitor used in the following Example is the human anti-PCSK9 antibody designated "mAb316P," also known here as "alirocumab." mAb316P has the following amino acid sequence characteristics: heavy chain variable region (HCVR) comprising SEQ ID NO:1; light chain variable domain (LCVR) comprising SEQ ID NO:6; heavy chain complementarity determining region 1 (HCDR1) comprising SEQ ID NO:2; HCDR2 comprising SEQ ID NO:3; HCDR3 comprising SEQ ID NO:4; light chain complementarity determining region 1 (LCDR1) comprising SEQ ID NO:7; LCDR2 comprising SEQ ID NO:8; and LCDR3 comprising SEQ ID NO:10.

Example 2: Attainment of Low-Density Lipoprotein Cholesterol Goals in Patients at High Cardiovascular Risk: Results from a Managed Care Population Study Background:

US guidelines support LDL-C goals based on patient's cardiovascular (CV) risk profile, however, little is known regarding real-world patterns of LDL-C goal attainment within specific high CV risk conditions.

Methods:

Patients from the OptumInsight IMPACT Database (a large US multi-payer claims database) with an LDL-C measurement during July 2011 to June 2012 and high CV risk conditions were identified. Most recent LDL-C measurement was defined as the index date and high CV risk conditions were identified hierarchically during the pre-index period as follows: recent acute coronary syndrome (ACS, within 6 months pre-index date), coronary events (myocardial infarction, hospitalization for unstable angina, coronary revascularization), stroke, and peripheral vascular disease (PVD).

Results:

In total, 110,739 patients met the inclusion criterion. Median (IQR) age was 59 (53 to 65) years, 53.7% were male, and median (IQR) LDL-C was 116 (92 to 143) mg/dL. As of index date, 2.7% had a recent ACS, while 42.1%, 9.2%, and 46.0% had evidence of coronary events, stroke, and PVD, respectively. The following table (Table 1) represents a summary distribution of patients by LDL-C levels as of index date for different high CV risk conditions.

TABLE 1

Breakdown of patients by LDL-C level (mg/dL) and risk condition.

| High CV Risk Condition (% Patients; N) | % Patients by LDL-C Level (mg/dL) | | | | | |
|---|---|---|---|---|---|---|
| | <70 | ≥70 to <100 | ≥100 to <130 | ≥130 to <160 | ≥160 | Any |
| Recent ACS (2.7%; 2,966) | 17.2% | 27.4% | 26.7% | 16.5% | 12.1% | 100.0% |
| Coronary Events (42.1%; 46,616) | 9.5% | 25.1% | 30.3% | 21.4% | 13.8% | 100.0% |
| Stroke (9.2%; 10,240) | 8.0% | 23.8% | 30.4% | 23.5% | 14.3% | 100.0% |
| PVD (46.0%; 50,917) | 6.9% | 23.0% | 31.8% | 23.8% | 14.5% | 100.0% |
| Overall (100%; 110,739) | 8.3% | 24.0% | 30.9% | 22.6% | 14.1% | 100.0% |

Conclusions:

In a large, contemporary cohort of high CV risk patients, few achieved LDL-C goals of <70 mg/dL (optional goal for very high CV risk) or <100 mg/dL. Although LDL-C goal achievement improved marginally in patients with conditions signifying higher CV risk, with highest achievement in patients with recent ACS, the majority of these patients were still above LDL-C goals. These data show that there is a need for ongoing efforts to address gaps in LDL-C goal attainment and improving CV outcomes in high-risk patients.

Example 3: Low-Density Lipoprotein Cholesterol Goal Attainment and Lipid-Lowering Therapy in a High Cardiovascular Risk Managed Care Population Background:

While US guidelines support statins as first line therapy to reduce LDL-C, little is known regarding real-world patterns of LDL-C goal attainment with statins and other lipid-lowering therapies (LLTs).

Methods:

Patients from the OptumInsight IMPACT Database (a large US multi-payer claims database) with an LDL-C measurement during July 2011 to June 2012 and high risk CV conditions (coronary events (myocardial infarction, hospitalization for unstable angina, coronary revascularization), stroke, and peripheral vascular disease) were identified. LLT prescription was assessed as of most recent LDL-C measurement (index date) and categorized as high-potency statin (atorvastatin 40/80 mg, rosuvastatin 20/40 mg, simvastatin 80 mg), standard-potency statin (other statins), non-statin LLT (ezetimibe, niacin, fibrates, bile acid sequestrants), and no LLT.

Results:

In total, 110,739 patients met the inclusion criterion. Median (IQR) age was 59 (53 to 65) years, 53.7% were male, and median (IQR) LDL-C was 116 (92 to 143) mg/dL. As of index date, 10.8% were on high-potency statin, 26.9% were on standard-potency statin, 5.3% were on non-statin LLT, and 57.0% were not on any LLT. The following table (Table 2) represents a summary distribution of patients by LDL-C levels as of index date for different LLT types.

TABLE 2

Breakdown of patients by LDL-C level (mg/dL) and LLT type.

| LLT Type (% Patients; N) | % Patients by LDL-C Level (mg/dL) | | | | | |
|---|---|---|---|---|---|---|
| | <70 | ≥70 to <100 | ≥100 to <130 | ≥130 to <160 | ≥160 | Any |
| High-Potency Statin (10.8%; 12,014) | 15.2% | 33.7% | 26.0% | 13.7% | 11.4% | 100.0% |
| Standard-Potency Statin (26.9%; 29,734) | 11.2% | 30.1% | 28.5% | 18.2% | 12.0% | 100.0% |
| Non-Statin LLT (5.3%; 5,921) | 12.1% | 27.6% | 29.8% | 19.0% | 11.5% | 100.0% |
| No LLT (57.0%; 63,070) | 5.3% | 19.0% | 33.1% | 26.7% | 15.9% | 100.0% |
| Overall (100%; 110,739) | 8.3% | 24.0% | 30.9% | 22.6% | 14.1% | 100.0% |

Conclusions:

In this large, contemporary population of patients at high CV risk, few achieved LDL-C goals of <70 mg/dL (optional goal for very high CV risk) or <100 mg/dL. Further, many other patients were not at LDL-C goal despite receiving a high-potency statin. These data show that there is a need for ongoing efforts to improve adherence to LLT as well as new therapies to improve goal attainment and CV outcomes.

Example 4: Monoclonal Antibody to PCSK-9, MAb316P Dose-Dependently Decreases Atherosclerosis, Induces a More Stable Plaque Phenotype and Enhances the Effects of Atorvastatin in APOE*3Leiden.CETP Transgenic Mice Background The aim of this study was to investigate the effects of two dosages of mAb316P, alone and in combination with atorvastatin on plasma lipids, atherosclerosis development, and lesion composition in APOE*3Leiden.CETP mice. This is a well-established model for hyperlipidemia and atherosclerosis with all features of familial dysbetalipoproteinemia (FD) in humans, which is characterized by accumulation of remnant lipoproteins and an increased very LDL (VLDL) cholesterol to LDL-C ratio. APOE*3Leiden mice have an impaired clearance of (V)LDL and increased TG levels, and are thereby mimicking the slow clearance observed in humans, in contrast to normal wild-type mice, which have a very rapid clearance of apoB-containing lipoproteins. The lipoprotein profile in APOE*3Leiden.CETP mice reflects that of FD patients with a similar response to lipid-modifying therapies, including statins, fibrates, niacin, and cholesteryl ester transfer protein (CETP) inhibitors. This is illustrated by a comparable reduction in cholesterol in all apoB-containing lipoprotein subfractions with statin treatment. It was hypothesized that mAb316P alone could reduce progression of atherosclerosis and add to the atheroprotective effects of atorvastatin. Inhibition of atherosclerosis by atorvastatin in APOE*3Leiden.CETP mice has been observed previously.

Methods i) Animals

Ninety female APOE*3Leiden.CETP transgenic mice (9 to 13 weeks of age), expressing human CETP under control of its natural flanking regions, were used. During the study, mice were housed under standard conditions with a 12-hour light-dark cycle and had free access to food and water. Animal experiments were approved by the Institutional Animal Care and Use Committee of The Netherlands Organization for Applied Research.

ii) Experimental Design

Mice received a semi-synthetic cholesterol-rich diet, containing 15% (w/w) cacao butter and 0.15% cholesterol (Western-type diet [WTD]; Hope Farms, Woerden, The Netherlands) for a run-in period of 3 weeks to increase plasma total cholesterol (TC) levels up to ~15 mmol/L. Body weight (BW) and food intake were monitored regularly during the study. After matching based on BW, TC, plasma TG, and age, mice (n=15 per group) received a WTD alone or were treated with two dosages of mAb316P (3 or 10 mg/kg) alone or in combination with atorvastatin (3.6 mg/kg/d) for 18 weeks, and an arm with atorvastatin alone was added. MAb316P was administered via weekly subcutaneous injections and atorvastatin was added to the diet. The dose of atorvastatin was calculated in order to attempt a TC reduction of about 20% to 30%. At the end of the treatment period, all animals were sacrificed by $CO_2$ inhalation. Livers and hearts were isolated to assess hepatic LDLR protein levels, lipid content, atherosclerosis development, and plaque composition.

iii) Plasma Lipids, Lipoprotein Analysis, and Measurement of MAb316P Levels

Plasma was isolated from blood collected in ethylenediaminetetraacetic acid (EDTA)-coated cups via tail vein bleeding after a 4-hour fast every 2 to 4 weeks. Plasma TC and TG were determined using enzymatic kits according to the manufacturer's protocols (cat. no. 1458216 and cat. no. 1488872, respectively; Roche/Hitachi) and average plasma TC and TG levels were calculated. Lipoprotein profiles for TC were measured after lipoprotein separation by fast protein liquid chromatography (FPLC) after 4, 12, and 18 weeks of treatment. MAb316P levels were measured by a human Fc enzyme-linked immunosorbent assay.

iv) Hepatic LDLR Protein Levels

Liver tissues were homogenized in lysis buffer (50 mM Tris-HCL [pH=7.4], 150 mM NaCl, 0.25% deoxycholic acid, 1% NP-40 [Igepal], 1 mM EDTA, protease inhibitor cocktail [complete, Roche], 1 mM PMSF, 1 mM Na3VO4) and then centrifuged at 6500 rpm at 4° C. for 30 minutes. Protein concentration in cell lysates was determined by bicinchonic acid protein assay (Thermo Scientific) according to manufacturer's instructions. 50 µg of protein lysates was separated by SDS-PAGE and then transferred to polyvinylidene fluoride membranes (Millipore). Blots were subjected to goat anti-mouse LDLR from R&D Systems and rabbit anti-goat horseradish peroxidase (HRP) from AbD Serotec or mouse anti-α-Tubulin from Sigma and horse anti-mouse HRP from Cell Signaling Technologies (according to the manufacturer's instructions); blots were developed with West Femto Super Signal ECL (Thermo Scientific) and subjected to the Chemi-Doc-it imaging system. Intensities of protein bands were quantified using Image J software.

v) Histological Assessment of Atherosclerosis

Hearts were isolated, fixed in formalin, and embedded in paraffin. Cross-sections (5 µm each) of the entire aortic root area were stained with hematoxylin-phloxin-saffron. For each mouse, four sections at intervals of 50 µm were used for quantitative and qualitative assessment of the atherosclerotic lesions. To determine atherosclerotic lesion size and severity, the lesions were classified into five categories according to the American Heart Association classification: I) early fatty streak, II) regular fatty streak, III) mild plaque, IV) moderate plaque, and V) severe plaque. Total lesion area and number of lesions per cross-section, as well as the percentage undiseased segments, were calculated. To assess lesion severity as a percentage of all lesions, type I-Ill lesions were classified as mild lesions, and type IV-V lesions were classified as severe lesions. To determine the total plaque load in the thoracic aorta, perfusion-fixed aortas (from the aortic origin to the diaphragm) were cleaned of extravascular fat, opened longitudinally, pinned en face, and stained for lipids with oil-red O as described previously by Verschuren et al. (Arterioscler Thromb Vasc Biol. 2005; 25:161-167). Data were normalized for analyzed surface area and expressed as percentage of the stained area. Photos/images were taken with the Olympus BX51 microscope and lesion areas were measured using Cell D imaging software (Olympus Soft Imaging Solutions).

In the aortic root, lesion composition was determined for the severe lesions (type IV-V) as a percentage of lesion area after immunostaining with mouse anti-human alpha actin (1:800; Monosan, Uden, The Netherlands) for smooth muscle cells (SMC), and rat anti-mouse Mac-3 (1:25; BD Pharmingen, the Netherlands) for macrophages followed by sirius red staining for collagen. Necrotic area and cholesterol clefts, monocyte adhesion to the endothelium, T-cells abundance in the aortic root area and the calculation of plaque stability index (defined as the ratio of collagen and SMC area as stabilization factors to macrophage and necrotic area as destabilization factors) were determined as previously described by Kuhnast et al. (J Hypertens. 2012; 30:107-116), Stary et al. (Arterioscler Thromb Vasc Biol. 1995; 15:1512-1531), and Kuhnast et al. (PLoS One. 2013; 8: e66467). Rat anti-mouse CD54 antibody, GTX76543 (GeneTex, Inc., San Antonio, Tex., USA) was used for immunostaining of intercellular adhesion molecule 1 (ICAM-1). Photos/images of the lesions were taken with the Olympus BX40 microscope with Nuance 2 multispectral imaging system, and stained areas were quantified using Image J software.

vi) Hepatic Lipid Analysis and Fecal Excretion of Bile Acids and Neutral Sterols Liver tissue samples were homogenized in phosphate-buffered saline, and the protein content was measured. Lipids were extracted, separated by high-performance thin-layer chromatography on silica gel plates, and analyzed with TINA2.09 software (Raytest Isotopen Messgerate Straubenhardt, Germany), as previously described by Post et al. (Hepatology. 1999; 30:491-500).

Mice were housed at five mice per cage, and feces were collected during two consecutive periods of 72 hours and 48 hours, respectively. Aliquots of lyophilized feces were used for determination of neutral and acidic sterol content by gas-liquid-chromatography, as previously described by Post et al. (Arterioscler Thromb Vasc Biol. 2003; 23:892-897).

vii) Flow Cytometric Analysis

After 8 weeks of treatment, peripheral blood mononuclear cells (PBMCs) were isolated from fresh blood samples and were sorted into GR-1+ (neutrophils/granulocytes), GR-1− (lymphocytes/monocytes), CD3+ (T-cells), CD19+ (B-cells) and CD11b+/Ly6C$^{low}$ and CD11b+/Ly6C$^{hi}$ (monocytes) cells using flow cytometric (FACS) analysis. The following conjugated monoclonal antibodies were used from Becton Dickinson: GR-1 FITC, CD3 PerCpCy5-5, CD19 V450, CD11b APC and Ly6C PE-Cy7.

viii) Statistical Analysis

Significance of differences between the groups was calculated non-parametrically using a Kruskal-Wallis test for independent samples, followed by a Mann-Whitney U-test for independent samples. Linear regression analyses were used to assess correlations between variables. Since the atherosclerotic lesion area showed a quadratic dependence on plasma cholesterol exposure, it was transformed using square root transformation. IBM SPSS Statistics 20 for Windows (SPSS, Chicago, USA) was used for statistical analyses. All groups were compared to the control group and to the atorvastatin group, and 3 mg/kg mAb316P was compared to 10 mg/kg mAb316P either with or without atorvastatin. Values are presented as means±SD. P-values <0.05 were considered statistically significant for single comparison. Bonferroni's method was used to determine the level of significance in the case of multiple comparisons. In the figures, significant effects after correction for multiple comparisons are indicated by *** to compare to the control group, ††† to compare to the atorvastatin group, and ‡‡‡ to compare 3 mg/kg mAb316P to 10 mg/kg mAb316P.

Figure 1B:
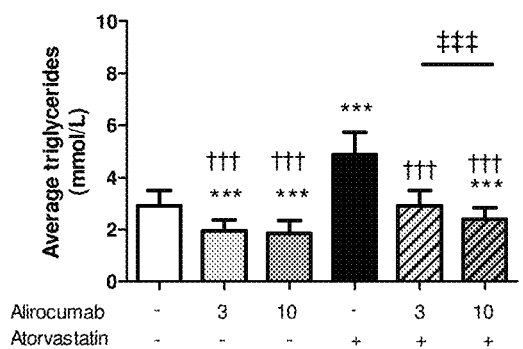
Figure 1C:
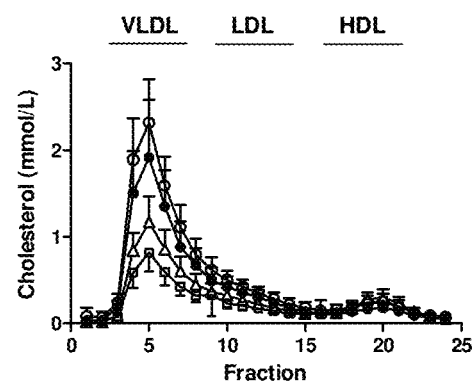
Figure 1D:
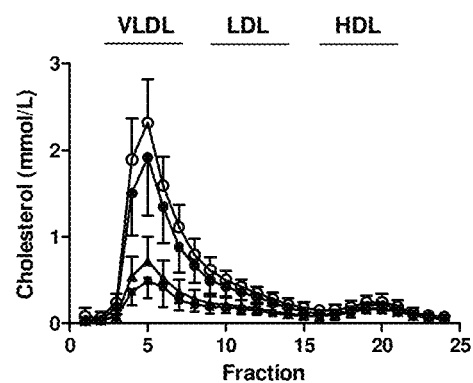
Figure 2A:
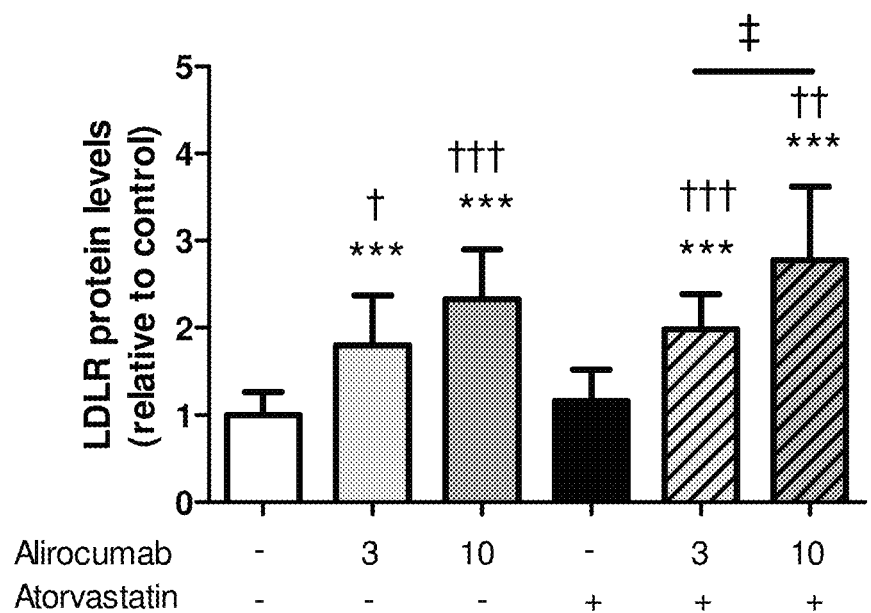
FIG. 2A shows a graph of the effect of mAb316P, atorvastatin, and their combination on hepatic low density lipoprotein receptor protein levels. *$P<0.0045$ as compared to control; †$P<0.05$; ††$P<0.01$; †††$P<0.0045$ as compared to atorvastatin; ‡$P<0.05$ compared 3 mg/kg mAb316P to 10 mg/kg mAb316P (n=8 per group).

Results i) MAb316P and Atorvastatin Monotreatment and their Combination Decrease Plasma Total Cholesterol and Triglycerides in APOE*3Leiden.CETP Mice Circulating mAb316P levels were detected in all groups administered mAb316P and ranged between 5 to 12 µg/mL (3 mg/kg dose) and 12 to 30 µg/mL (10 mg/kg dose) during the 18-week study. The APOE*3Leiden.CETP mice on a cholesterol-containing WTD (control group) reached average plasma TC and TG levels of 16.2±1.8 mmol/L and 2.9±0.6 mmol/L, respectively (FIGS. 1A and 1B). Compared to the control, mAb316P decreased average plasma TC (−37%, P<0.001; −46%, P<0.001) and TG (−33%, P<0.001; −39%, P<0.001), and further decreased TC in combination with atorvastatin (−48%, P<0.001; −58%, P<0.001). Compared to atorvastatin, both combination treatments decreased TC (−36%, P<0.001; −48%, P<0.001) and TG (−40%, P<0.001; −51%, P<0.001) to a greater extent than atorvastatin alone. The reductions in TC after mAb316P alone (−14%, P<0.01; 3 mg mAb316P versus 10 mg mAb316P) and in combination with atorvastatin (−19%, P<0.001; 3 mg mAb316P+atorvastatin versus 10 mg mAb316P+atorvastatin) were dose-dependent and sustained during the study. TC reductions after mAb316P (FIG. 1C), atorvastatin, and their combination (FIG. 1D) were confined to apoB-containing lipoproteins. No effects on BW (gain) and food intake were noted in any treatment groups compared with the control.

ii) MAb316P, without and with Atorvastatin, Decreases Plasma Lipids by Reducing Low-Density Lipoprotein Receptor Degradation, and Reduces Non-HDL-Cholesterol Hepatic LDLR protein levels were measured to verify whether PCSK9 inhibition by mAb316P decreases plasma lipids by rescuing LDLR degradation (FIG. 2A). Hepatic LDLR protein levels were increased after mAb316P treatment alone (+80%, P<0.01; +133%, P<0.01) and together with atorvastatin (+98%, P<0.001; +178%, P<0.05). Compared to atorvastatin alone, both the combination treatments increased LDLR protein levels to a greater extent (+71%, P<0.0045; +140%, P<0.01). An inverse correlation between LDLR protein levels and plasma TC confirms the involvement of the LDLR in lowering of TC by mAb316P ($R^2=0.50$, P<0.001).

Figure 2B:
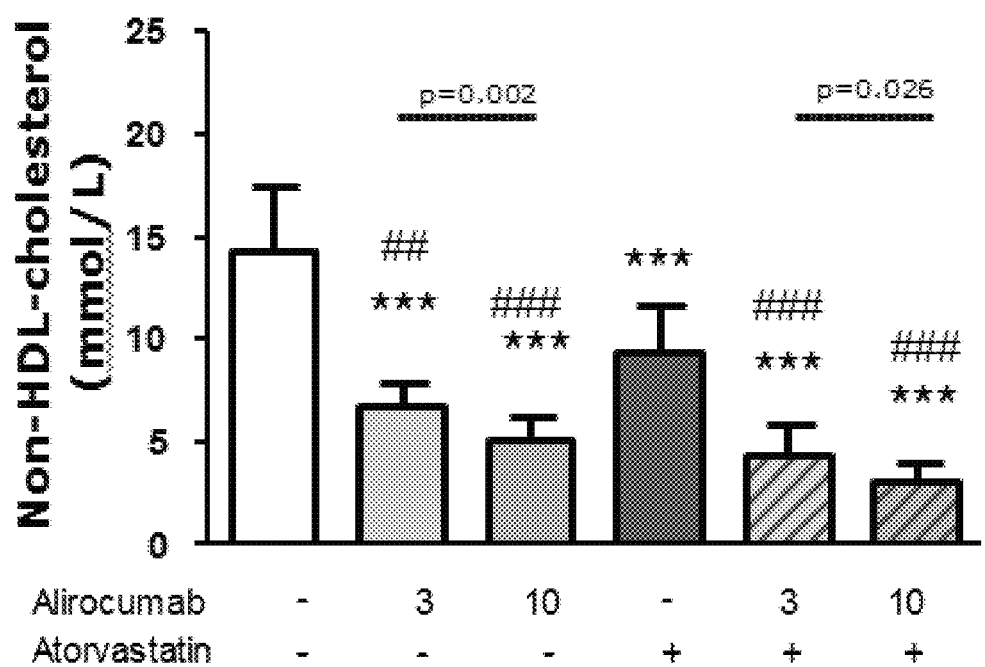
FIG. 2B shows a graph of the effect of mAb316P, atorvastatin, and their combination on non-HDL-cholesterol levels. *$P<0.001$ as compared to control; #$P<0.05$; ##$P<0.01$; ###$P<0.001$ as compared to atorvastatin.
Figure 3A:
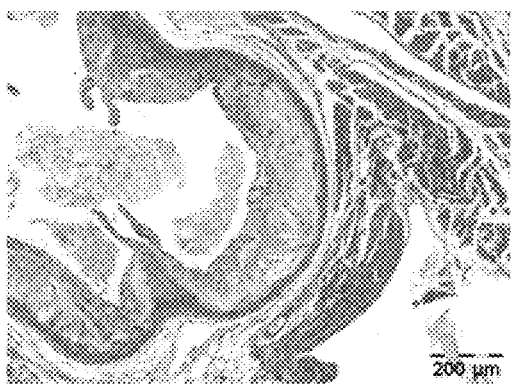
FIGS. 3A-F is a series of photos depicting the effect of mAb316P, atorvastatin, and their combination on plaque morphology. Representative images of hematoxylin-phloxine-saffron-stained atherosclerotic lesions in a cross section of the aortic root area for the control (FIG. 3A), 3 mg/kg mAb316P (FIG. 3B), 10 mg/kg mAb316P (FIG. 3C), atorvastatin (FIG. 3D), 3 mg/kg mAb316P+atorvastatin (FIG. 3E) and 10 mg/kg mAb316P+atorvastatin (FIG. 3F) groups, respectively, after 18 weeks of treatment.
Figure 3B:
Figure 3C:
Figure 3D:
Figure 3E:
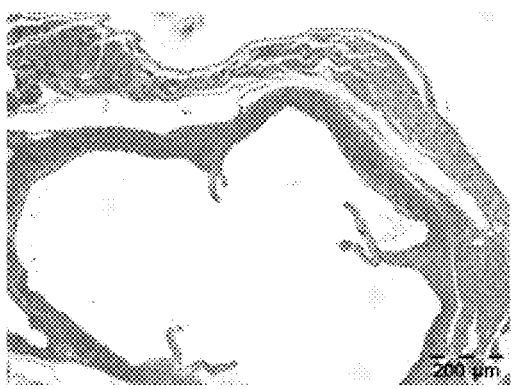
Figure 3F:

Non-HDL-Cholesterol levels were also measured to verify whether PCSK9 inhibition by mAb316P decreases such levels by up-regulation of the LDLR (FIG. 2B).

iii) MAb316P does not Affect Liver Lipids and Fecal Bile Acid and Neutral Sterol Excretion To evaluate the consequences of mAb316P-induced alterations in lipoprotein metabolism on hepatic lipid metabolism and excretion into feces, liver lipids and excretion of bile acids and neutral sterols in stool were determined. MAb316P did not affect liver weight nor the hepatic content of cholesterol and TG, whereas atorvastatin and the combination treatments led to significant reductions in liver weight (−15%, P=0.067; −17%, P<0.05, N.S. after correction for multiple comparisons; −20%, P<0.0045, respectively) and hepatic cholesteryl esters (−48%, P<0.0045; −41%, P<0.0045 and −44%, P<0.05, N.S. after correction for multiple comparisons, respectively) as compared to the control group, without a change in hepatic triglycerides (Table 3). Fecal output of bile acids and neutral sterols was not changed by the treatments (Table 4). These data indicate that despite the greater influx of cholesterol from the plasma compartment, hepatic cholesterol homeostasis is maintained during mAb316P and statin treatment.

TABLE 3

Effect of mAb316P, atorvastatin and their combination on liver lipids.

| | Liver lipids (µg/mg protein) | | |
|---|---|---|---|
| | FC | CE | TG |
| Control | 11.6 ± 1.6 | 50.6 ± 14.0 | 119.2 ± 33.3 |
| 3 mg mAb316P | 11.2 ± 1.4† | 48.2 ± 8.2††† | 117.7 ± 21.6 |
| 10 mg mAb316P | 11.4 ± 2.0† | 53.9 ± 10.4††† | 142.1 ± 43.0† |
| Atorvastatin | 9.5 ± 0.9* | 26.2 ± 4.8*** | 90.6 ± 28.5 |
| 3 mg mAb316P + atorvastatin | 10.4 ± 1.8 | 29.6 ± 5.8*** | 103.5 ± 36.8 |
| 10 mg mAb316P + atorvastatin | 10.7 ± 1.2 | 28.3 ± 9.0* | 109.8 ± 28.8 |

FC: free cholesterol;
CE: cholesterol esters;
TG: triglycerides.
*P < 0.05, ***P < 0.0045 as compared to control;
†P < 0.05, †††P < 0.0045 as compared to atorvastatin.

TABLE 4

Effect of mAb316P, atorvastatin and their combination on neutral sterol and bile acid excretion.

| | Neutral sterol excretion (µmol/100 g mouse/day) | Bile acid excretion (µmol/100 g mouse/day) |
|---|---|---|
| Control | 25.8 ± 5.5 | 13.5 ± 3.3 |
| 3 mg mAb316P | 20.4 ± 6.2† | 14.3 ± 2.7† |
| 10 mg mAb316P | 21.6 ± 5.6† | 12.4 ± 3.2 |
| Atorvastatin | 30.3 ± 6.5 | 10.7 ± 2.4 |
| 3 mg mAb316P + atorvastatin | 28.6 ± 6.0 | 11.4 ± 2.2 |
| 10 mg mAb316P + atorvastatin | 27.5 ± 4.4 | 12.7 ± 1.6 |

Figure 4A:
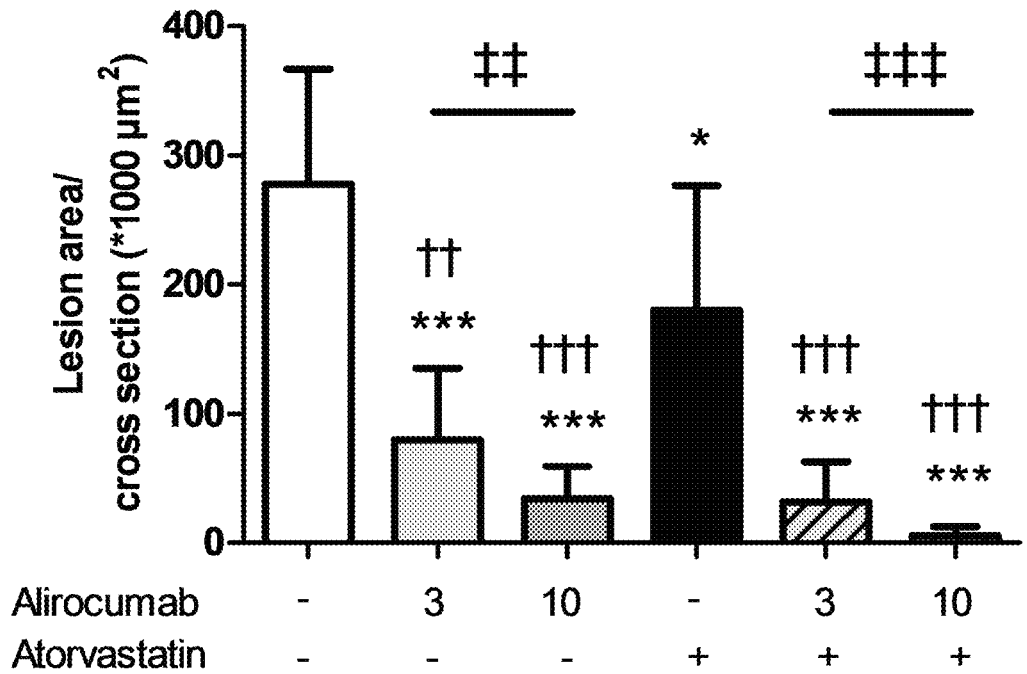
FIGS. 4A-D shows a series of graphs depicting the effect of mAb316P, atorvastatin, and their combination on atherosclerosis development in aortic root and arch. After 18 weeks of treatment, the total lesion area (FIG. 4A) and number of lesions (FIG. 4B) per cross section were assessed. Lesion severity was assessed and categorized as no lesions, mild (type I-III) and severe (type IV-V) lesions (FIG. 4C). The total plaque load in the aortic arch (FIG. 4D) was analyzed after oil-red O-staining. Data are expressed as percentage of the stained area. *$P<0.05$; ***$P<0.0045$ as compared to control; †$P<0.05$; ††$P<0.01$; †††$P<0.0045$ as compared to atorvastatin; ‡$P<0.05$; ‡$P<0.01$; ‡‡‡$P<0.0045$ compared 3 mg/kg mAb316P to 10 mg/kg mAb316P (n=15 per group in the root area and n=6-7 in the arch).
Figure 4B:
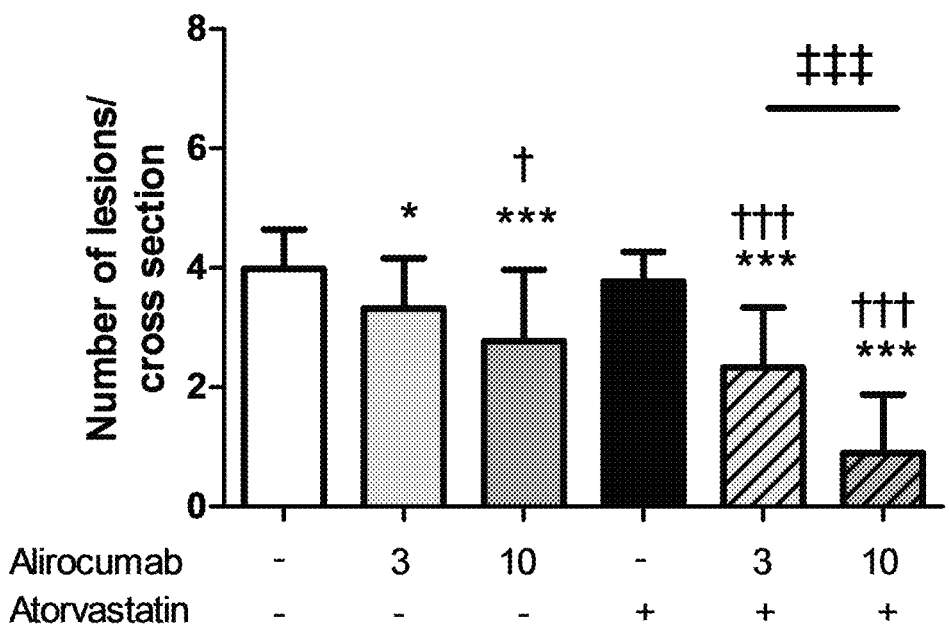
Figure 4C:
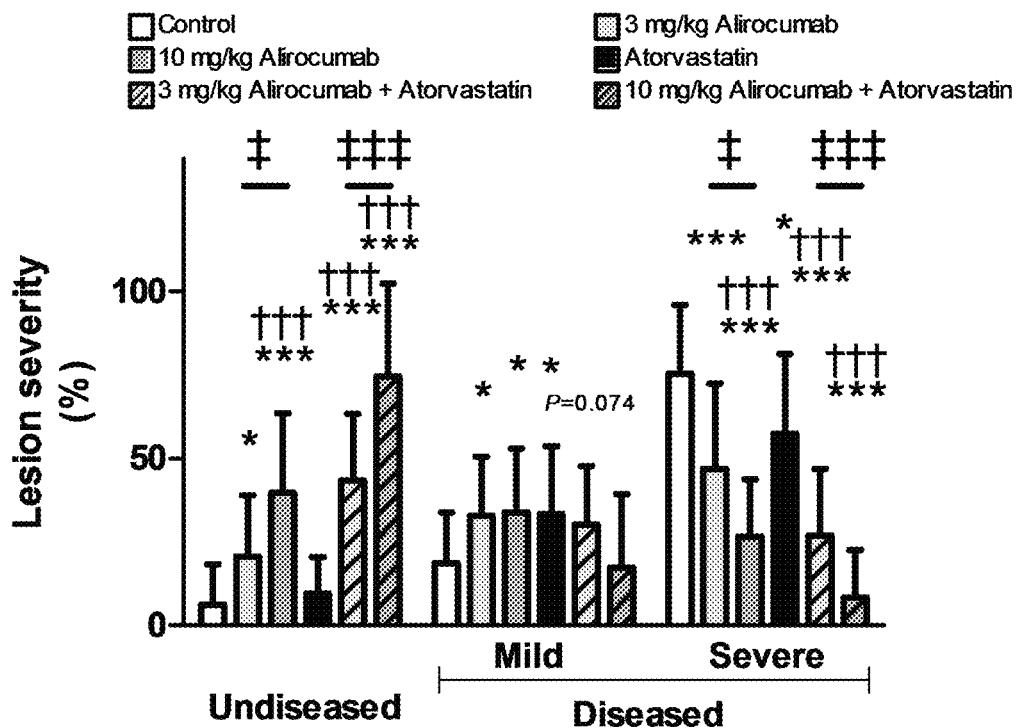

†P < 0.05 as compared to atorvastatin.

iv) MAb316P Dose-Dependently Reduces Atherosclerosis Development and Enhances the Atheroprotective Effects of Atorvastatin Effects of mAb316P on atherosclerosis development, in the absence and presence of atorvastatin, were assessed in the aortic root and arch after 18 weeks of treatment. Representative images of atherosclerotic lesions, as illustrated in FIG. 3, show that mAb316P, atorvastatin, and their combination reduced lesion progression. To confirm a reduction in atherosclerosis development, the lesion area and the number of lesions per cross-section were evaluated (FIG. 4A and FIG. 4B), along with lesion severity (FIG. 4C). For the control group, total lesion area was 278±89×103 µm2 per cross-section, which consisted of 4.0±0.7 lesions per cross section. MAb316P dose-dependently decreased atherosclerotic lesion size (−71%, P<0.001; −88%, P<0.001) and dose-dependently enhanced the effects of atorvastatin (−89%, P<0.001; −98%, P<0.001) as compared to the control. In addition, mAb316P, with and without atorvastatin, also decreased the number of lesions (−17%, P<0.05, N.S. after correction for multiple comparisons; −30%, P<0.0045 and −41%, P<0.001; −77%, P<0.001, respectively). Mice treated with mAb316P, alone and in combination with atorvastatin, had more lesion-free sections and fewer severe (type IV-V) lesions compared with the control. Atorvastatin alone decreased lesion size (−35%, P<0.05, N.S. after correction for multiple comparisons) and reduced severity to a lesser extent with no effect on the number of lesions or undiseased segments. When compared to atorvastatin monotreatment, the combinations further decreased lesion size (−82%, P<0.001; −97%, P<0.001) and number of lesions (−38%, P<0.001; −76%, P<0.001) and increased the amount of undiseased segments.

Figure 4D:
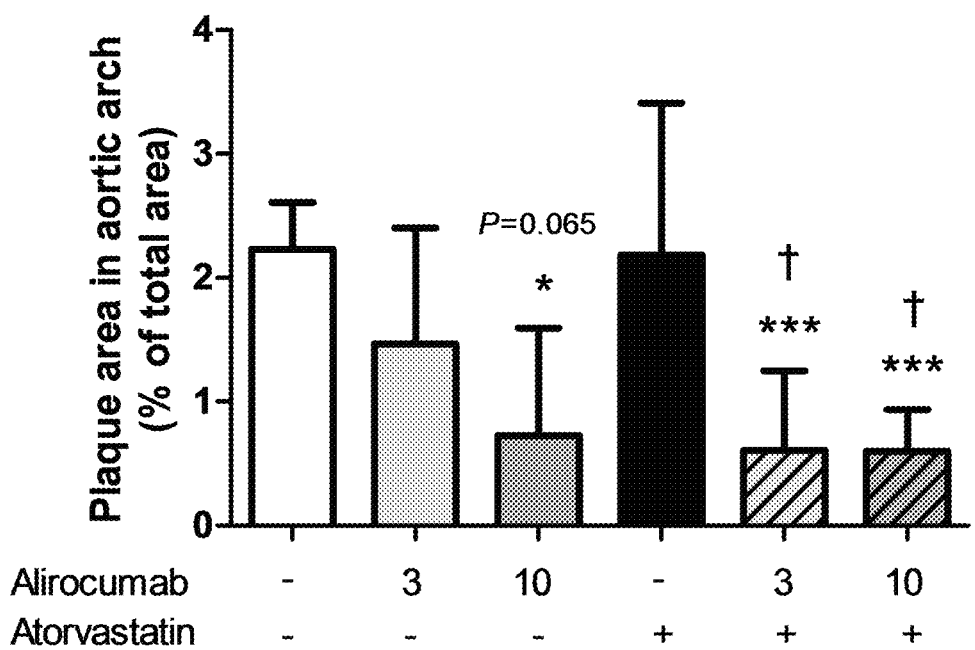

To evaluate the effect of mAb316P treatment on lesion development at another spot along the aorta prone to development of atherosclerosis, plaque surface in the aortic arch was measured (FIG. 4D). At this site, lesion development is delayed as compared with the aortic root. In line with the effects on atherogenesis in the aortic origin, 10 mg/kg mAb316P alone (−67%, P<0.05, N.S. after correction for multiple comparisons) and both doses together with atorvastatin (−73%, P<0.0045; −73%, P<0.0045) reduced the total plaque area.

Figure 5:
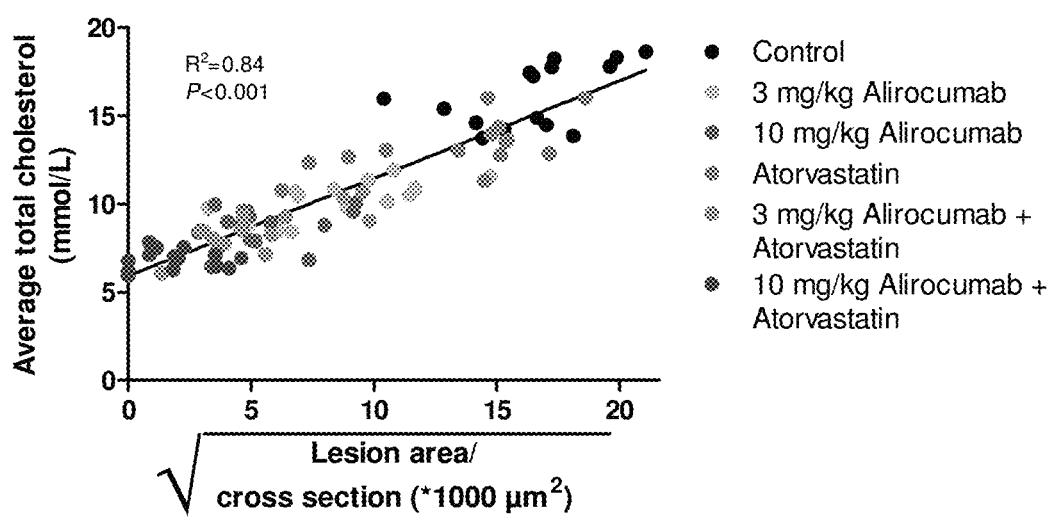
FIG. 5 is a graph depicting the correlation between average plasma total cholesterol and atherosclerotic lesion area. The square root of the lesion area was plotted against average total cholesterol. Linear regression analysis was performed.
Figure 7A:
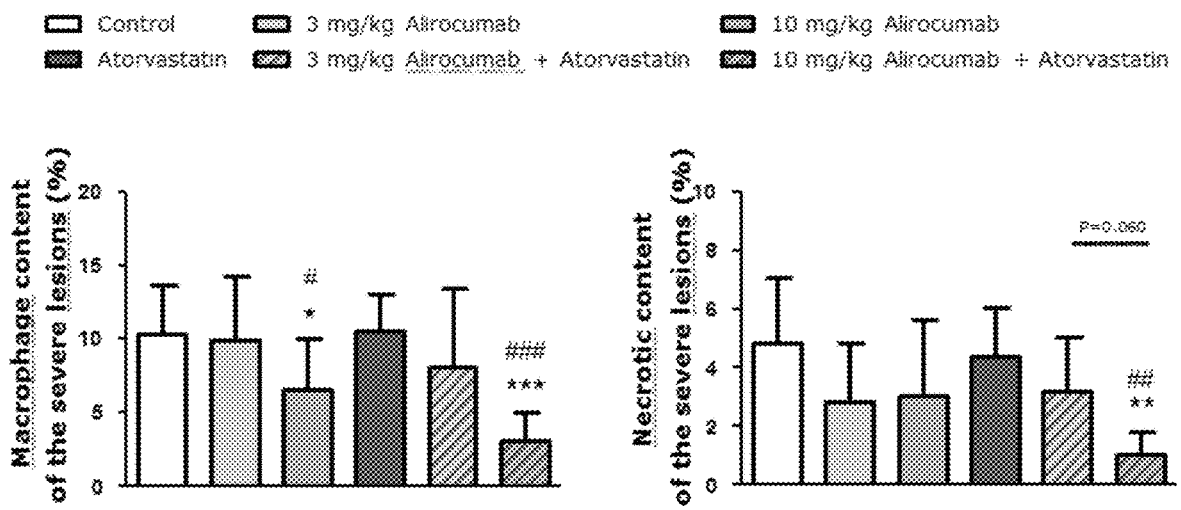
FIGS. 7A-C is a series of graphs depicting the effect of mAb316P, atorvastatin, and their combination on lesion composition. Macrophage content (FIG. 7A left) and necrotic content (FIG. 7A right), including cholesterol clefts, as destabilization factors, and SMC content (FIG. 7B left) and collagen content (FIG. 7B right) as stabilization factors were determined in the severe (type IV-V) lesions after correcting for lesion size. *$P<0.05$, $P<0.01$, *$P<0.001$ as compared to control; #$P<0.05$, ##$P<0.01$, ###$P<0.001$ as compared to atorvastatin. The plaque stability index was calculated as the ratio of the stabilization factors to the destabilization factors (FIG. 7C). *$P<0.05$, ***$P<0.0045$ as compared to control; †$P<0.05$, †††$P<0.0045$ as compared to atorvastatin; ‡$P<0.05$ for 3 mg/kg mAb316P compared to 10 mg/kg mAb316P (n=15 per group).
Figure 8A:
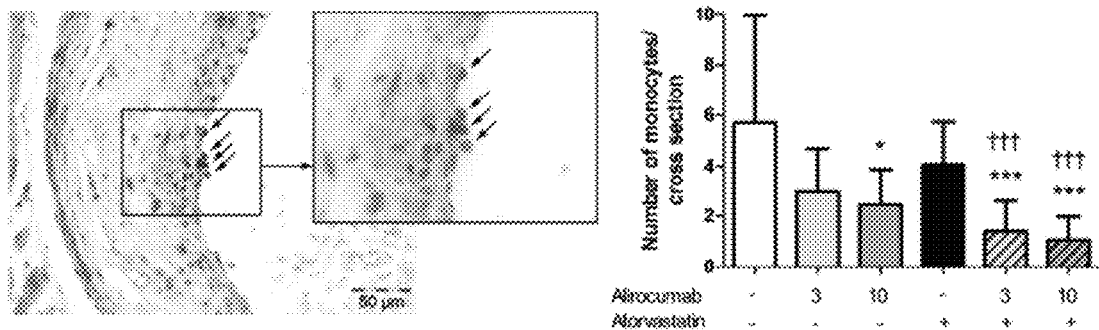
FIGS. 8A-C is a series of graphs depicting the effect of mAb316P, atorvastatin, and their combination on markers of vascular inflammation. The number of monocytes adhering to the endothelium (FIG. 8A) and the number of T-cells in the aortic root area (FIG. 8B) were determined per cross section. In addition, intercellular adhesion molecule 1 (ICAM-1) was determined as percentage of the stained area (FIG. 8C). Representative images are included. *$P<0.05$, $P<0.01$, *$P<0.0045$ as compared to control; †$P<0.05$, †††$P<0.0045$ as compared to atorvastatin (n=15 per group).
Figure 8B:
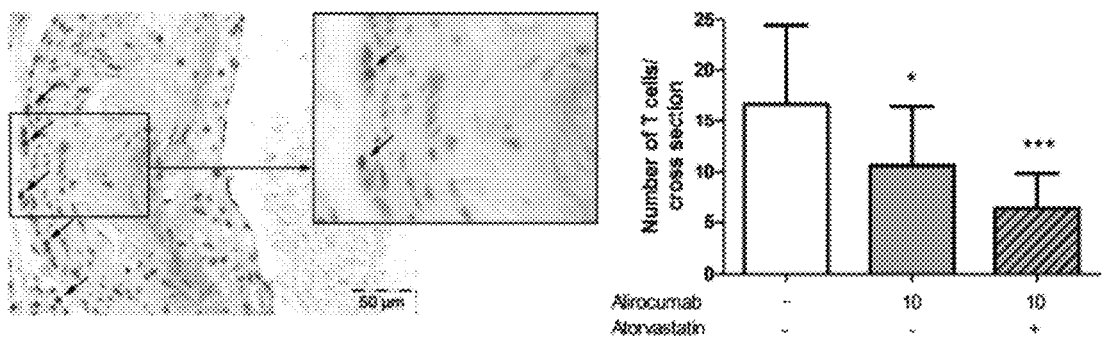
Figure 8C:
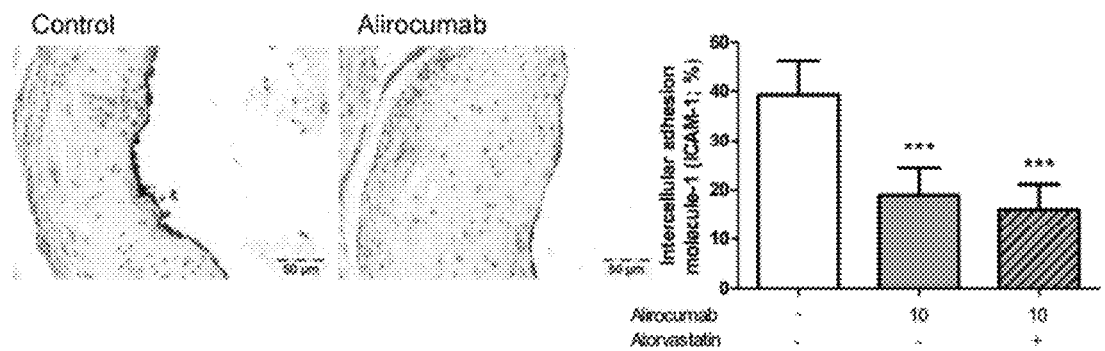

The anti-atherogenic effect of mAb316P and atorvastatin were evaluated (FIG. 5) and a strong correlation between plasma TC levels and atherosclerotic lesion area in the aortic root was observed ($R^2=0.84$, P<0.001; FIG. 5), indicating an important role of cholesterol in the development of atherosclerosis.

v) MAb316P Reduces Monocyte and T-Cell Recruitment and Improves Lesion Stability Index As a functional marker of vessel wall inflammation, the number of monocytes adhering to the activated endothelium (FIG. 8A) and the number of T-cells in the aortic root area (FIG. 8B) was counted and calculated per cross section (FIG. 7A). In the control group, 5.7±4.2 adhering monocytes and 16.7±7.7 T-cells were present. When administered alone and together with atorvastatin, the higher dose of mAb316P (10 mg/kg) decreased the adhering monocytes (−57%, P<0.01, N.S. after correction for multiple comparisons, and −75%, P<0.001) and the abundance of T-cells (−37%, P<0.05, N.S. after correction for multiple comparisons, and −62%, P<0.001). To further underline the mechanism by which mAb316P reduced monocyte adherence, endothelial ICAM-1 expression by immunohistochemistry (FIG. 8C) was assessed. For the control, 39% of the endothelium was positive for ICAM-1 compared to 19% (P<0.001) after 10 mg/kg mAb316P monotreatment and 16% (P<0.001) when given in combination with atorvastatin. The reduction in monocyte adherence was, therefore, corroborated by a reduction in adhesion molecule expression in endothelial cells after mAb316P treatment alone and in combination with atorvastatin.

Figure 6:
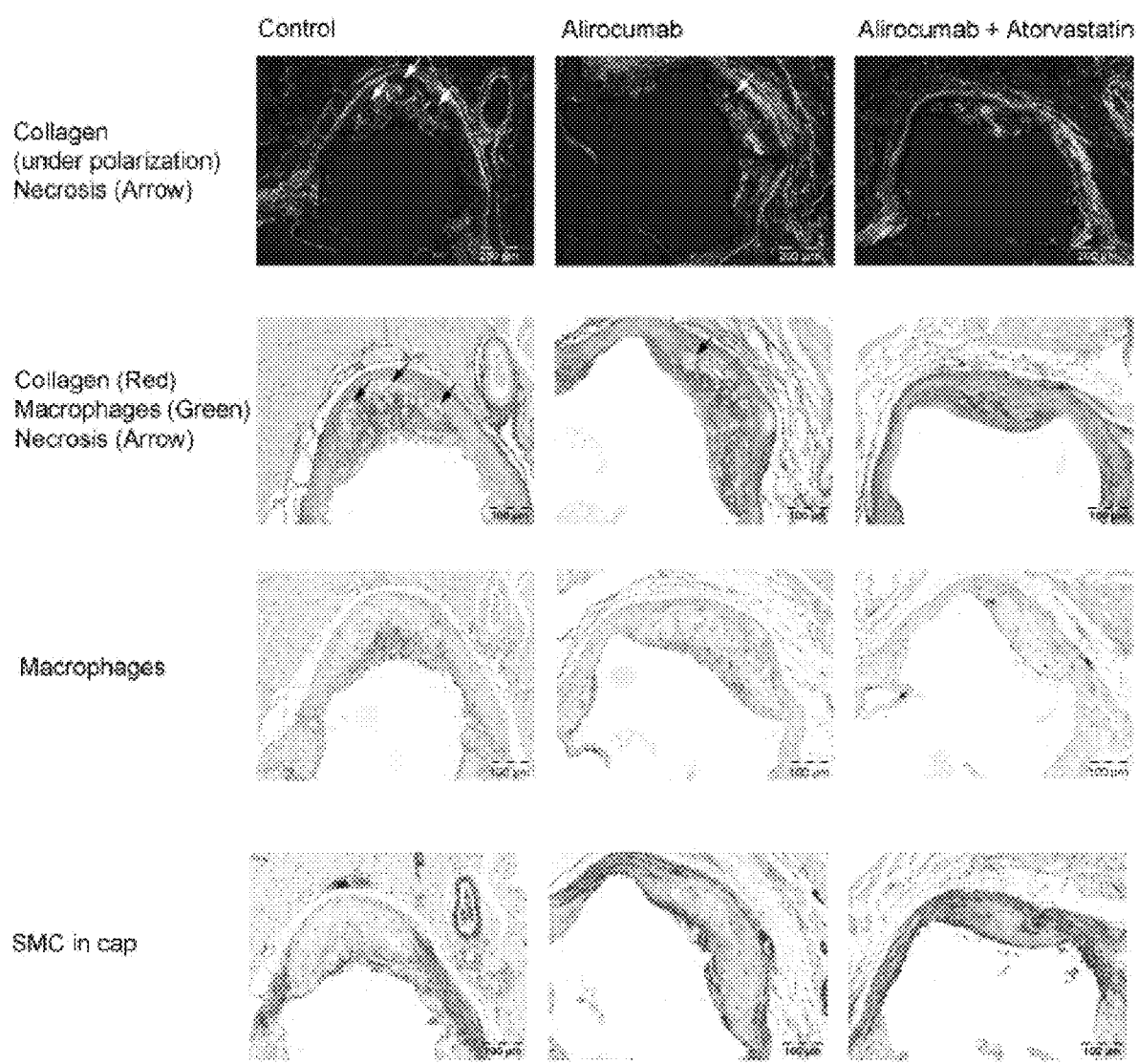
FIG. 6 is a series of photos depicting the effect of mAb316P, atorvastatin, and their combination on lesion composition. Representative images of immunostaining with Mac-3 for macrophages followed by sirius red staining for collagen and alpha actin for smooth muscle cells (SMC) for the control and after 18 weeks of treatment with mAb316P alone and in combination with atorvastatin.
Figure 7B:
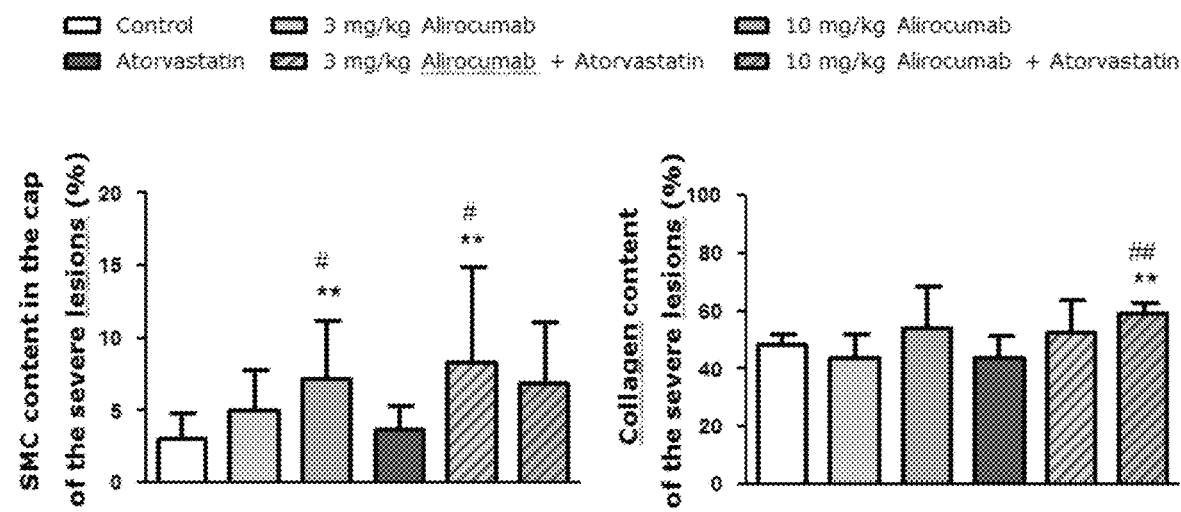
Figure 7C:
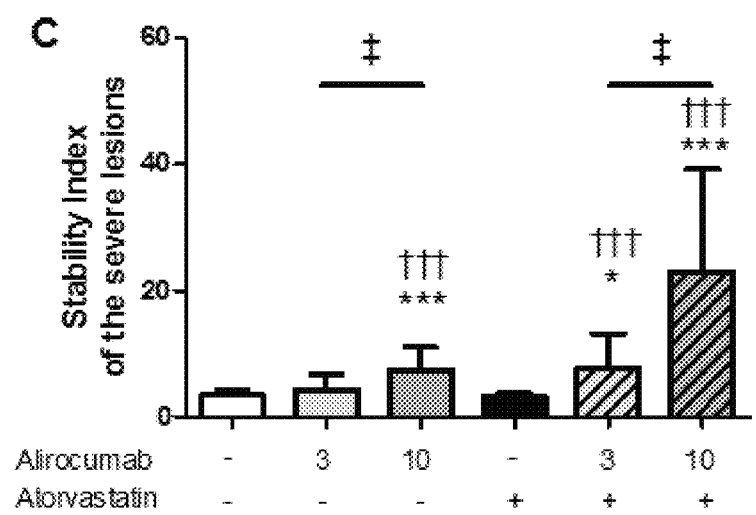

After investigating lesion morphology, treatment effects on plaque composition were analyzed in the severe lesions (type IV-V), which are considered to be the most vulnerable lesions as shown by representative images in FIG. 6. To illustrate that plaque stability is not always dependent on the size of the lesions, included are representative images of similar size lesions for the control group and the mAb316P group. Lesion macrophage area (FIG. 7A left) plus lesion necrotic core area (including cholesterol clefts) (FIG. 7A right), were quantified as destabilization factors whereas SMC in the fibrotic cap (FIG. 7B left) and collagen area (FIG. 7B right) were quantified as stabilization factors. All were expressed as a percentage of total lesion area. Lesions in the control group consisted of 10.3% macrophages, 4.8% necrotic core and cholesterol clefts, 3.1% SMC in the cap and 48.4% collagen. Lesion stability index (FIG. 7C) for the control group was 3.5±0.8. When administered in combination with atorvastatin, the lower dose of mAb316P (3 mg/kg) decreased the destabilization factors (−26%, P<0.05, N.S. after correction for multiple comparisons) and increased the stabilization factors (+19%, P<0.05, N.S. after correction for multiple comparisons), whereas the higher dose (10 mg/kg) alone and in combination with atorvastatin decreased the destabilization factors (−37%, P<0.001; +73%, P<0.001) and increased the stabilization factors (+19%, P<0.05, N.S. after correction for multiple comparisons; +29%, P<0.001). MAb316P, therefore, improved lesion stability as shown by an increase in lesion stability index alone (+24%, N.S.; +113%, P<0.0045) and together with atorvastatin (+116%, P<0.05, N.S. after correction for multiple comparisons; 556%, P<0.001).

vi) MAb316P Tends to Reduce the Circulating Monocytes

The effects of mAb316P alone and in combination with atorvastatin on white blood cell count was assessed by flow cytometry. Interestingly, mAb316P alone and together with atorvastatin reduced granulocytes/neutrophils (−20%, P<0.05, N.S. after correction for multiple comparisons; −34%, P<0.001) and monocytes (−28%, P<0.05, N.S. after correction for multiple comparisons; −39%, P<0.001) when expressed as a percentage of the PBMC population. More specifically, mAb316P alone and in combination with atorvastatin tended to decrease pro-inflammatory $Ly6C^{hi}$ (−8%, P=0.061; −19%, P<0.001) and increase anti-inflammatory $Ly6C^{low}$ (+12%, P=0.089; +35%, P<0.001) monocytes. Therefore, the effect of mAb316P on vascular recruitment and adhesion of monocytes may be augmented by a reduction in circulating monocytes.

TABLE 5

Effect of mAb316P, atorvastatin, and their combination on white blood cell count as assessed by flow cytometric analysis after 8 weeks of treatment.

| | Control | 10 mg/kg MAb316P | Atorvastatin | 10 mg/kg MAb316P + Atorvastatin |
|---|---|---|---|---|
| Neutrophils/Granulocytes (% of PBMC population) | 8.9 ± 2.4 | 7.1 ± 2.0*†† | 5.1 ± 1.6*** | 5.9 ± 2.0*** |
| Lymphocytes/Monocytes (% of PBMC population) | 91.1 ± 2.4 | 92.9 ± 2.0*†† | 94.9 ± 1.6*** | 94.1 ± 2.0*** |
| T-cells (% of PBMC population) | 22.9 ± 4.6 | 21.4 ± 5.0† | 17.0 ± 4.8*** | 18.5 ± 4.5* |
| B-cells (% of PBMC population) | 63.9 ± 8.5 | 66.3 ± 15.0 | 69.5 ± 17.4*** | 66.9 ± 2.0*** |
| Monocytes (% of PBMC population) | 12.3 ± 5.0 | 8.9 ± 2.5*††† | 5.3 ± 2.4*** | 7.5 ± 2.8***† |
| CD11b+ $Ly6C^{hi}$ (% of monocytes) | 62.2 ± 8.5 | 57.5 ± 8.4 P = 0.061† | 51.2 ± 6.4*** | 50.2 ± 4.1*** |
| CD11b+ $Ly6C^{low}$ (% of monocytes) | 35.6 ± 7.7 | 40.0 ± 8.0 P = 0.089† | 47.8 ± 6.3*** | 48.0 ± 3.5*** |

*P < 0.05, ***P < 0.0125 as compared to control;
†P < 0.05, ††P < 0.01, †††P < 0.0125 as compared to atorvastatin (n = 15 per group)

SUMMARY

The present study was designed to investigate the effects of mAb316P per se on atherosclerosis development and in combination with atorvastatin. Taken together, these data demonstrate that mAb316P dose-dependently decreases plasma cholesterol, progression of atherosclerosis and plaque vulnerability, and enhances the beneficial effects of atorvastatin in APOE*3Leiden.CETP mice. This is the first study to show that a monoclonal antibody to PCSK9 reduces atherosclerosis development.

We claim:

1. A method of inhibiting progression of atherosclerosis comprising:
    administering to a subject in need thereof a therapeutically effective amount of a proprotein convertase subtilisin/kexin type 9 (PCSK9) antibody or antigen-binding fragment thereof, wherein the PCSK9 antibody or antigen-binding fragment thereof comprises heavy and light chain complementarity determining regions (CDR) amino acid sequences having SEQ ID NOs: 2, 3, 4, 7, 8, and 10; and
    wherein the subject has suffered a stroke or myocardial infarction.

2. The method of claim 1, wherein the subject is nonhyperlipidemic.

3. The method of claim 1, wherein the subject is nonhypercholesterolemic.

4. The method of claim 1, wherein the subject is nonhypertriglyceridemic.

5. The method of claim 1, wherein the subject has a disease or disorder selected from the group consisting of type I diabetes mellitus, type II diabetes mellitus, Kawasaki disease, chronic inflammatory disease, and hypertension.

6. The method of claim 1, wherein the subject has elevated levels of an inflammatory marker.

7. The method of claim 6, wherein the inflammatory marker is C-reactive protein.

8. The method of claim 6, wherein the inflammatory marker is an inflammatory cytokine.

9. The method of claim 1, wherein the subject has heterozygous Familial Hypercholesterolemia (heFH).

10. The method of claim 1, wherein the subject has a form of hypercholesterolemia that is not Familial Hypercholesterolemia (nonFH).

11. The method of claim 1, wherein the subject is on another lipid-modifying agent before or during administration of the antibody or antigen-binding protein.

12. The method of claim 11, wherein the therapeutic lipid-modifying agent is a statin, ezetimibe, a fibrate, niacin, an omega-3 fatty acid, or a bile acid resin.

13. The method of claim 12, wherein the statin is cerivastatin, atorvastatin, simvastatin, pitavastatin, rosuvastatin, fluvastatin, lovastatin, or pravastatin.

14. The method of claim 1, wherein the subject is not on another lipid-modifying agent before or during administration of the antibody or antigen-binding protein.

15. The method of claim 1, wherein the subject has an LDL-C level greater than or equal to 70 mg/dL.

16. The method of claim 1, wherein the antibody or antigen-binding protein comprises a heavy chain variable region (HCVR) having the amino acid sequence of SEQ ID NO:1 and a light chain variable region (LCVR) having the amino acid sequence of SEQ ID NO:6.

17. The method of claim 1, wherein the antibody or antigen-binding protein reduces atherosclerotic plaque formation in the subject by at least 10%.

18. The method of claim 1, wherein the antibody or antigen binding protein is administered subcutaneously.

19. The method of claim 1, wherein the administering step comprises administering to the subject one or more doses of 150 mg of the antibody or antigen-binding fragment thereof about every two weeks.

* * * * *

SEQUENCE LISTING

<160> NUMBER OF SEQ ID NOS: 198

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser
        115

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Thr Phe Asn Asn Tyr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Ser Gly Ser Gly Gly Thr Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Lys Asp Ser Asn Trp Gly Asn Phe Asp Leu
1               5                   10

<210> SEQ ID NO 5
<211> LENGTH: 447
<212> TYPE: PRT
<213> ORGANISM: Artificial Sequence
<220> FEATURE:
<223> OTHER INFORMATION: Description of Artificial Sequence: Synthetic REGN727 heavy chain polypeptide

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

```
Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ser Val Leu Tyr Arg Ser Asn Asn Arg Asn Phe
1               5                   10

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Ala Ser
1
```

<210> SEQ ID NO 9
<211> LENGTH: 220
<212> TYPE: PRT
<213> ORGANISM: Artificial Sequence
<220> FEATURE:
<223> OTHER INFORMATION: Description of Artificial Sequence: Synthetic
      REGN727 light chain polypeptide

<400> SEQUENCE: 9

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Gln Gln Tyr Tyr Thr Thr Pro Tyr Thr
1               5
```

<210> SEQ ID NO 11
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Glu Met Gln Leu Val Glu Ser Gly Gly Gly Leu Val Gln Pro Gly Gly
1               5                   10                  15
```

-continued

Ser Leu Arg Leu Ser Cys Ala Ala Ser Gly Phe Thr Phe Ser Ser His
            20                  25                  30

Trp Met Lys Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr Asp Met Asp Tyr Tyr Tyr Tyr
            100                 105                 110

Gly Met Asp Val Trp Gly Gln Gly Thr Thr Val Thr Val Ser Ser
        115                 120                 125

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Thr Phe Ser Ser His Trp
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Asn Gln Asp Gly Ser Glu Lys
1               5

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Arg Asp Ile Val Leu Met Val Tyr Asp Met Asp Tyr Tyr Tyr Tyr
1               5                   10                  15

Gly Met Asp Val
            20

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Val Met Thr Gln Ser Pro Leu Ser Leu Pro Val Thr Pro Gly

```
                1               5                   10                  15
            Glu Pro Ala Ser Ile Ser Cys Arg Ser Ser Gln Ser Leu Leu His Ser
                            20                  25                  30

Asn Gly Asn Asn Tyr Leu Asp Trp Tyr Leu Gln Lys Pro Gly Gln Ser
                        35                  40                  45

Pro Gln Leu Leu Ile Tyr Leu Gly Ser Asn Arg Ala Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Met Gln Thr
                                85                  90                  95

Leu Gln Thr Pro Leu Thr Phe Gly Gly Gly Thr Lys Val Glu Ile Lys
                        100                 105                 110
```

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Gln Ser Leu Leu His Ser Asn Gly Asn Asn Tyr
1               5                   10
```

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Leu Gly Ser
1
```

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Met Gln Thr Leu Gln Thr Pro Leu Thr
1               5
```

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Gly Phe Thr Phe Ser Ser His Trp
1               5
```

<210> SEQ ID NO 20
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Asn Gln Asp Gly Ser Glu Lys
1               5

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Arg Asp Ile Val Leu Met Val Tyr Asp Met Asp Tyr Tyr Tyr Tyr
1               5                   10                  15

Gly Met Asp Val
            20

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Leu His His Ser Asn Gly Asn Asn Tyr
1               5                   10

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Gly Ser
1

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Gln Thr Leu Gln Thr Pro Leu Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 25

Gly Phe Thr Phe Ser Ser His Trp
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Asn Gln Asp Gly Ser Glu Lys
1               5

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Arg Asp Ile Val Leu Met Val Tyr His Met Asp Tyr Tyr Tyr Tyr
1               5                   10                  15

Gly Met Asp Val
            20

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Leu Leu His Ser Asn Gly Asn Asn Tyr
1               5                   10

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Gly Ser
1

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Gln Thr Leu Gln Thr Pro Leu Thr
1               5
```

```
<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Phe Thr Phe Ser Ser His Trp
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Asn Gln Asp Gly Ser Glu Lys
1               5

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg Asp Ile Val Leu Met Val Tyr His Met Asp Tyr Tyr Tyr Tyr
1               5                   10                  15

Gly Met Asp Val
            20

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Leu His His Ser Asn Gly Asn Asn Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Gly Ser
1

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 36

Met Gln Thr Leu Gln Thr Pro Leu Thr
1               5

<210> SEQ ID NO 37
<211> LENGTH: 131
<212> TYPE: PRT
<213> ORGANISM: Artificial Sequence
<220> FEATURE:
<223> OTHER INFORMATION: Description of Artificial Sequence: Synthetic
      VH; m2CX1D05 polypeptide

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser His
                20                  25                  30

Ala Ile Ser Trp Val Arg Gln Ala Pro Gly Gln Gly Leu Glu Trp Met
            35                  40                  45

Gly Gly Ile Asn Pro Ile Leu Gly Ile Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Glu Ile Gln Ile Gly Arg Tyr Gly Met Asn Val Tyr
            100                 105                 110

Tyr Leu Met Tyr Arg Phe Ala Ser Trp Gly Gln Gly Thr Leu Val Thr
        115                 120                 125

Val Ser Ser
        130

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR1; m2CX1D05 peptide

<400> SEQUENCE: 38

Gly Gly Thr Phe Asn Ser His Ala Ile Ser
1               5                   10

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      VH CDR2; m2CX1D05 peptide

<400> SEQUENCE: 39

Trp Met Gly Gly Ile Asn Pro Ile Leu Gly Ile Ala Asn Tyr Ala Gln
1               5                   10                  15

Lys Phe Gln Gly
            20

<210> SEQ ID NO 40
<211> LENGTH: 22

```
<212> TYPE: PRT
<213> ORGANISM: Artificial Sequence
<220> FEATURE:
<223> OTHER INFORMATION: Description of Artificial Sequence: Synthetic
      VH CDR3; m2CX1D05 peptide

<400> SEQUENCE: 40

His Tyr Glu Ile Gln Ile Gly Arg Tyr Gly Met Asn Val Tyr Tyr Leu
1               5                   10                  15

Met Tyr Arg Phe Ala Ser
            20

<210> SEQ ID NO 41
<211> LENGTH: 213
<212> TYPE: PRT
<213> ORGANISM: Artificial Sequence
<220> FEATURE:
<223> OTHER INFORMATION: Description of Artificial Sequence: Synthetic
      LC; m2CX1D05 polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Asn Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Ala
    210

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR 1; m2CX1D05 peptide

<400> SEQUENCE: 42

Arg Ala Ser Gln Gly Ile Arg Ser Ala Leu Asn
```

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR2; m2CX1D05 peptide

<400> SEQUENCE: 43

Leu Leu Ile Tyr Asn Gly Ser Thr Leu Gln Ser
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR3; m2CX1D05 peptide

<400> SEQUENCE: 44

Gln Gln Phe Asp Gly Asp Pro
1               5

<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic
      VH; 1B20 polypeptide

<400> SEQUENCE: 45

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110

Thr Leu Val Thr Val Ser Ser
        115

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR1; 1B20 peptide

<400> SEQUENCE: 46

Gly Tyr Ser Phe Thr Asn Tyr Trp Ile Ser
1               5                   10

```
<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic
      VH CDR2; 1B20 peptide

<400> SEQUENCE: 47

Trp Met Gly Ile Ile Tyr Pro Gly Asp Ser Tyr Thr Asn Tyr Ser Pro
1               5                   10                  15

Ser Phe Gln Gly
            20

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR3; 1B20 peptide

<400> SEQUENCE: 48

Asp Tyr Trp Tyr Lys Pro Leu Phe Asp Ile
1               5                   10

<210> SEQ ID NO 49
<211> LENGTH: 220
<212> TYPE: PRT
<213> ORGANISM: Artificial Sequence
<220> FEATURE:
<223> OTHER INFORMATION: Description of Artificial Sequence: Synthetic
      LC; 1B20 polypeptide

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Phe Pro Ile Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
```

```
                  195                 200                 205
Ser Pro Val Thr Lys Ser Phe Asn Arg Gly Glu Ala
    210                 215                 220

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      VL CDR1; 1B20 peptide

<400> SEQUENCE: 50

Arg Ser Ser Gln Ser Val Leu Tyr Ser Ser Asn Asn Lys Asn Tyr Leu
1               5                   10                  15

Ala

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR2; 1B20 peptide

<400> SEQUENCE: 51

Leu Leu Ile Tyr Trp Ala Ser Thr Arg Glu Ser
1               5                   10

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      VL CDR3; 1B20 peptide

<400> SEQUENCE: 52

Gln Gln Tyr Ser Ser Phe Pro Ile
1               5

<210> SEQ ID NO 53
<211> LENGTH: 120
<212> TYPE: PRT
<213> ORGANISM: Artificial Sequence
<220> FEATURE:
<223> OTHER INFORMATION: Description of Artificial Sequence: Synthetic
      variable heavy antibody region polypeptide

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
```

Leu Val Thr Val Ser Ser Ala Ser
        115                 120

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      AX132 heavy chain CDR1 antibody region peptide

<400> SEQUENCE: 54

Lys Ala Ser Gly Tyr Thr Phe Ser Ser Tyr Gly Met Tyr Trp Val Arg
1               5                   10                  15

<210> SEQ ID NO 55
<211> LENGTH: 23
<212> TYPE: PRT
<213> ORGANISM: Artificial Sequence
<220> FEATURE:
<223> OTHER INFORMATION: Description of Artificial Sequence: Synthetic
      AX132 heavy chain CDR2 antibody region peptide

<400> SEQUENCE: 55

Trp Ile Gly Trp Ile Asp Pro Gly Ser Gly Gly Thr Lys Tyr Asn Glu
1               5                   10                  15

Lys Phe Lys Gly Lys Ala Thr
            20

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      AX132 heavy chain CDR3 antibody region peptide

<400> SEQUENCE: 56

Cys Ala Arg Glu Arg Tyr Gly Tyr Tyr Phe Asp Tyr Trp Gly Gln
1               5                   10                  15

<210> SEQ ID NO 57
<211> LENGTH: 108
<212> TYPE: PRT
<213> ORGANISM: Artificial Sequence
<220> FEATURE:
<223> OTHER INFORMATION: Description of Artificial Sequence: Synthetic
      variable light antibody region polypeptide

<400> SEQUENCE: 57

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR1 antibody region peptide

<400> SEQUENCE: 58

Ile Thr Cys Arg Ala Ser Gln Tyr Val Gly Ser Tyr Leu Asn Trp Tyr
1               5                   10                  15

Gln

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR2 antibody region peptide

<400> SEQUENCE: 59

Leu Ile Tyr Asp Ala Ser Asn Arg Ala Thr Gly Ile Pro
1               5                   10

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      AX132 & AX213 light chain CDR3 antibody region peptide

<400> SEQUENCE: 60

Tyr Tyr Cys Gln Val Trp Asp Ser Ser Pro Pro Val Val Phe Gly Gly
1               5                   10                  15

<210> SEQ ID NO 61
<211> LENGTH: 120
<212> TYPE: PRT
<213> ORGANISM: Artificial Sequence
<220> FEATURE:
<223> OTHER INFORMATION: Description of Artificial Sequence: Synthetic
      variable heavy antibody region polypeptide

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Gly Ile Asn Trp Val Arg Gln Ala Pro Gly Lys Gly Leu Glu Trp Ile
        35                  40                  45

Gly Arg Ile Asp Pro Gly Asn Gly Gly Thr Arg Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asn Asp Gly Tyr Ser Phe Asp Tyr Trp Gly Gln Gly Thr
            100                 105                 110

Leu Val Thr Val Ser Ser Ala Ser
        115                 120

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      AX213 heavy chain CDR1 antibody region peptide

<400> SEQUENCE: 62

Lys Ala Ser Gly Tyr Thr Phe Ser Arg Tyr Gly Ile Asn Trp Val Arg
1               5                   10                  15

<210> SEQ ID NO 63
<211> LENGTH: 23
<212> TYPE: PRT
<213> ORGANISM: Artificial Sequence
<220> FEATURE:
<223> OTHER INFORMATION: Description of Artificial Sequence: Synthetic
      AX213 heavy chain CDR2 antibody region peptide

<400> SEQUENCE: 63

Trp Ile Gly Arg Ile Asp Pro Gly Asn Gly Gly Thr Arg Tyr Asn Glu
1               5                   10                  15

Lys Phe Lys Gly Lys Ala Thr
            20

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      AX213 heavy chain CDR3 antibody region peptide

<400> SEQUENCE: 64

Cys Ala Arg Ala Asn Asp Gly Tyr Ser Phe Asp Tyr Trp Gly Gln
1               5                   10                  15

<210> SEQ ID NO 65
<211> LENGTH: 108
<212> TYPE: PRT
<213> ORGANISM: Artificial Sequence
<220> FEATURE:
<223> OTHER INFORMATION: Description of Artificial Sequence: Synthetic
      variable light antibody region polypeptide

<400> SEQUENCE: 65

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR1 antibody region peptide

<400> SEQUENCE: 66

Ile Thr Cys Arg Ala Ser Gln Tyr Val Gly Ser Tyr Leu Asn Trp Tyr
1               5                   10                  15

Gln

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR2 antibody region peptide

<400> SEQUENCE: 67

Leu Ile Tyr Asp Ala Ser Asn Arg Ala Thr Gly Ile Pro
1               5                   10

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      AX132 & AX213 light chain CDR3 antibody region peptide

<400> SEQUENCE: 68

Tyr Tyr Cys Gln Val Trp Asp Ser Ser Pro Val Val Phe Gly Gly
1               5                   10                  15

<210> SEQ ID NO 69
<211> LENGTH: 119
<212> TYPE: PRT
<213> ORGANISM: Artificial Sequence
<220> FEATURE:
<223> OTHER INFORMATION: Description of Artificial Sequence: Synthetic
      AX1 VH antibody sequence polypeptide

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Thr Ser Tyr
                20                  25                  30

Tyr Met His Trp Val Arg Gln Ala Pro Gly Lys Gly Leu Glu Trp Ile
            35                  40                  45

Gly Arg Ile Asn Pro Asp Ser Gly Ser Thr Lys Tyr Asn Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Ser Trp Asp Phe Asp Val Trp Gly Gln Gly
            100                 105                 110

Thr Leu Val Thr Val Ser Ser
            115

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
    AX1 VH CDR1 antibody sequence peptide

<400> SEQUENCE: 70

Lys Ala Ser Gly Phe Thr Phe Thr Ser Tyr Tyr Met His Trp Val Arg
1               5                   10                  15

<210> SEQ ID NO 71
<211> LENGTH: 23
<212> TYPE: PRT
<213> ORGANISM: Artificial Sequence
<220> FEATURE:
<223> OTHER INFORMATION: Description of Artificial Sequence: Synthetic
    AX1 VH CDR2 antibody sequence peptide

<400> SEQUENCE: 71

Trp Ile Gly Arg Ile Asn Pro Asp Ser Gly Ser Thr Lys Tyr Asn Glu
1               5                   10                  15

Lys Phe Lys Gly Arg Ala Thr
            20

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
    AX1 VH CDR3 antibody sequence peptide

<400> SEQUENCE: 72

Cys Ala Arg Gly Gly Arg Leu Ser Trp Asp Phe Asp Val Trp Gly Gln
1               5                   10                  15

<210> SEQ ID NO 73
<211> LENGTH: 109
<212> TYPE: PRT
<213> ORGANISM: Artificial Sequence
<220> FEATURE:
<223> OTHER INFORMATION: Description of Artificial Sequence: Synthetic
    AX1 VL antibody sequence polypeptide

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Ala Tyr Asp Tyr Ser Leu Gly
                85                  90                  95

Gly Tyr Val Phe Gly Asp Gly Thr Lys Val Glu Ile Lys
            100                 105

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      AX1 VL CDR1 antibody sequence peptide

<400> SEQUENCE: 74

Arg Ala Ser Gln Asp Ile Ser Arg Tyr Leu Ala
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      AX1 AX9 AX189 VL CDR2 antibody sequence peptide

<400> SEQUENCE: 75

Ala Ala Ser Ser Leu Gln Ser
1               5

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      AX1 VL CDR3 antibody sequence peptide

<400> SEQUENCE: 76

Ala Ala Tyr Asp Tyr Ser Leu Gly Gly Tyr Val
1               5                   10

<210> SEQ ID NO 77
<211> LENGTH: 121
<212> TYPE: PRT
<213> ORGANISM: Artificial Sequence
<220> FEATURE:
<223> OTHER INFORMATION: Description of Artificial Sequence: Synthetic
      AX9 AX189 VH antibody sequence polypeptide

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
                20                  25                  30

Trp Met His Trp Val Arg Gln Ala Pro Gly Lys Gly Leu Glu Trp Ile
            35                  40                  45

Gly Arg Ile Asp Pro Tyr Asn Gly Gly Thr Lys Tyr Asn Glu Lys Phe
        50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Tyr Leu Gly Ser Tyr Ala Met Asp Tyr Trp Gly
            100                 105                 110

Gln Gly Thr Leu Val Thr Val Ser Ser
        115                 120

<210> SEQ ID NO 78
<211> LENGTH: 16

```
<212> TYPE: PRT
<213> ORGANISM: Artificial Sequence
<220> FEATURE:
<223> OTHER INFORMATION: Description of Artificial Sequence: Synthetic
      AX9 AX189 VH CDR1 antibody sequence peptide

<400> SEQUENCE: 78

Lys Ala Ser Gly Tyr Thr Phe Ser Ser Tyr Trp Met His Trp Val Arg
1               5                   10                  15

<210> SEQ ID NO 79
<211> LENGTH: 23
<212> TYPE: PRT
<213> ORGANISM: Artificial Sequence
<220> FEATURE:
<223> OTHER INFORMATION: Description of Artificial Sequence: Synthetic
      AX9 AX189 VH CDR2 antibody sequence peptide

<400> SEQUENCE: 79

Trp Ile Gly Arg Ile Asp Pro Tyr Asn Gly Gly Thr Lys Tyr Asn Glu
1               5                   10                  15

Lys Phe Lys Gly Lys Ala Thr
            20

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      AX9 AX189 VH CDR3 antibody sequence peptide

<400> SEQUENCE: 80

Cys Ala Arg Tyr Gly Tyr Tyr Leu Gly Ser Tyr Ala Met Asp Tyr Trp
1               5                   10                  15

Gly Gln

<210> SEQ ID NO 81
<211> LENGTH: 109
<212> TYPE: PRT
<213> ORGANISM: Artificial Sequence
<220> FEATURE:
<223> OTHER INFORMATION: Description of Artificial Sequence: Synthetic
      AX189 VL antibody sequence polypeptide

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Arg Tyr
            20                  25                  30

Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Leu Ser
                85                  90                  95

Gly Tyr Val Phe Gly Gly Gly Thr Lys Val Glu Ile Lys
            100                 105

<210> SEQ ID NO 82
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      AX189 VL CDR1 antibody sequence peptide

<400> SEQUENCE: 82

Arg Ala Ser Gln Asp Val Ser Arg Tyr Leu Thr
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      AX1 AX9 AX189 VL CDR2 antibody sequence peptide

<400> SEQUENCE: 83

Ala Ala Ser Ser Leu Gln Ser
1               5

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      AX189 VL CDR3 antibody sequence peptide

<400> SEQUENCE: 84

Gln Ala Tyr Asp Tyr Ser Leu Ser Gly Tyr Val
1               5                   10

<210> SEQ ID NO 85
<211> LENGTH: 115
<212> TYPE: PRT
<213> ORGANISM: Homo sapiens

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 86
<211> LENGTH: 5
<212> TYPE: PRT
<213> ORGANISM: Homo sapiens

<400> SEQUENCE: 86
```

```
Ser Tyr Gly Ile Ser
1               5

<210> SEQ ID NO 87
<211> LENGTH: 17
<212> TYPE: PRT
<213> ORGANISM: Homo sapiens

<400> SEQUENCE: 87

Trp Val Ser Phe Tyr Asn Gly Asn Thr Asn Tyr Ala Gln Lys Leu Gln
1               5                   10                  15

Gly

<210> SEQ ID NO 88
<211> LENGTH: 6
<212> TYPE: PRT
<213> ORGANISM: Homo sapiens

<400> SEQUENCE: 88

Gly Tyr Gly Met Asp Val
1               5

<210> SEQ ID NO 89
<211> LENGTH: 109
<212> TYPE: PRT
<213> ORGANISM: Homo sapiens

<400> SEQUENCE: 89

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

<210> SEQ ID NO 90
<211> LENGTH: 14
<212> TYPE: PRT
<213> ORGANISM: Homo sapiens

<400> SEQUENCE: 90

Thr Gly Thr Ser Ser Asp Val Gly Gly Tyr Asn Ser Val Ser
1               5                   10

<210> SEQ ID NO 91
<211> LENGTH: 7
<212> TYPE: PRT
<213> ORGANISM: Homo sapiens

<400> SEQUENCE: 91

Glu Val Ser Asn Arg Pro Ser
1               5
```

```
<210> SEQ ID NO 92
<211> LENGTH: 9
<212> TYPE: PRT
<213> ORGANISM: Homo sapiens

<400> SEQUENCE: 92

Asn Ser Tyr Thr Ser Thr Ser Met Val
1               5

<210> SEQ ID NO 93
<211> LENGTH: 123
<212> TYPE: PRT
<213> ORGANISM: Homo sapiens

<400> SEQUENCE: 93

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Tyr Asp Phe Trp Ser Ala Tyr Tyr Asp Ala Phe Asp Val
            100                 105                 110

Trp Gly Gln Gly Thr Met Val Thr Val Ser Ser
        115                 120

<210> SEQ ID NO 94
<211> LENGTH: 10
<212> TYPE: PRT
<213> ORGANISM: Homo sapiens

<400> SEQUENCE: 94

Gly Phe Thr Phe Ser Ser Tyr Ser Met Asn
1               5                   10

<210> SEQ ID NO 95
<211> LENGTH: 17
<212> TYPE: PRT
<213> ORGANISM: Homo sapiens

<400> SEQUENCE: 95

Ser Ile Ser Ser Ser Ser Tyr Ile Ser Tyr Ala Asp Ser Val Lys
1               5                   10                  15

Gly

<210> SEQ ID NO 96
<211> LENGTH: 14
<212> TYPE: PRT
<213> ORGANISM: Homo sapiens

<400> SEQUENCE: 96

Asp Tyr Asp Phe Trp Ser Ala Tyr Tyr Asp Ala Phe Asp Val
1               5                   10

<210> SEQ ID NO 97
```

```
<211> LENGTH: 111
<212> TYPE: PRT
<213> ORGANISM: Homo sapiens

<400> SEQUENCE: 97

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Ser Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110

<210> SEQ ID NO 98
<211> LENGTH: 14
<212> TYPE: PRT
<213> ORGANISM: Homo sapiens

<400> SEQUENCE: 98

Thr Gly Ser Ser Ser Asn Ile Gly Ala Gly Tyr Asp Val His
1               5                   10

<210> SEQ ID NO 99
<211> LENGTH: 7
<212> TYPE: PRT
<213> ORGANISM: Homo sapiens

<400> SEQUENCE: 99

Gly Asn Ser Asn Arg Pro Ser
1               5

<210> SEQ ID NO 100
<211> LENGTH: 11
<212> TYPE: PRT
<213> ORGANISM: Homo sapiens

<400> SEQUENCE: 100

Gln Ser Tyr Asp Ser Ser Leu Ser Gly Ser Val
1               5                   10

<210> SEQ ID NO 101
<211> LENGTH: 114
<212> TYPE: PRT
<213> ORGANISM: Homo sapiens

<400> SEQUENCE: 101

Gln Val Gln Leu Val Glu Ser Gly Gly Gly Val Ala Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Tyr Tyr Asp Gly Ile Asn Lys His Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Leu Asp Trp Gly Gln Gly Thr Leu Val Thr Val
            100                 105                 110

Ser Ser

<210> SEQ ID NO 102
<211> LENGTH: 10
<212> TYPE: PRT
<213> ORGANISM: Homo sapiens

<400> SEQUENCE: 102

Gly Phe Thr Phe Ser Ser Tyr Gly Met His
1               5                   10

<210> SEQ ID NO 103
<211> LENGTH: 17
<212> TYPE: PRT
<213> ORGANISM: Homo sapiens

<400> SEQUENCE: 103

Val Ile Tyr Tyr Asp Gly Ile Asn Lys His Tyr Ala Asp Ser Val Lys
1               5                   10                  15

Gly

<210> SEQ ID NO 104
<211> LENGTH: 5
<212> TYPE: PRT
<213> ORGANISM: Homo sapiens

<400> SEQUENCE: 104

Asp Arg Gly Leu Asp
1               5

<210> SEQ ID NO 105
<211> LENGTH: 113
<212> TYPE: PRT
<213> ORGANISM: Homo sapiens

<400> SEQUENCE: 105

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys

```
<210> SEQ ID NO 106
<211> LENGTH: 17
<212> TYPE: PRT
<213> ORGANISM: Homo sapiens

<400> SEQUENCE: 106

Lys Ser Ser Gln Ser Val Leu Tyr Ser Ser Asn Ser Lys Asn Tyr Leu
1               5                   10                  15
Val

<210> SEQ ID NO 107
<211> LENGTH: 7
<212> TYPE: PRT
<213> ORGANISM: Homo sapiens

<400> SEQUENCE: 107

Trp Ala Ser Thr Arg Glu Ser
1               5

<210> SEQ ID NO 108
<211> LENGTH: 9
<212> TYPE: PRT
<213> ORGANISM: Homo sapiens

<400> SEQUENCE: 108

Gln Gln Tyr Tyr Ser Thr Pro Trp Thr
1               5

<210> SEQ ID NO 109
<211> LENGTH: 118
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG04 (clones LGT-209 and LGT-210)
      Vh heavy chain variable region (FR1-FR4) polypeptide

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Met
            20                  25                  30

Tyr Met Ser Trp Val Arg Gln Ala Pro Gly Gln Gly Leu Glu Trp Met
        35                  40                  45

Gly Arg Ile Asp Pro Ala Asn Glu His Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Ser Tyr Tyr Tyr Asn Met Asp Tyr Trp Gly Gln Gly Thr
            100                 105                 110

Leu Val Thr Val Ser Ser
        115

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209, LGT-210 and LGT-211
      heavy chain CDR1 peptide
```

```
<400> SEQUENCE: 110

Thr Met Tyr Met Ser
1               5

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209, LGT-210 and LGT-211
      heavy chain CDR2 peptide

<400> SEQUENCE: 111

Arg Ile Asp Pro Ala Asn Glu His Thr Asn Tyr Ala Gln Lys Phe Gln
1               5                   10                  15

Gly

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG04(clones LGT-209 and LGT-210)
      Vh heavy chain complementarity determining region 3 (CDR3) peptide

<400> SEQUENCE: 112

Ser Tyr Tyr Tyr Tyr Asn Met Asp Tyr
1               5

<210> SEQ ID NO 113
<211> LENGTH: 106
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG10(clones LGT-209 and LGT-211)
      Vk light chain variable region (FR1-FR4) polypeptide

<400> SEQUENCE: 113

Gln Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Gly Val Phe Arg Arg Ala Thr Gly Ile Pro Asp Arg Phe Ser Gly Ser
    50                  55                  60

Gly Ser Gly Thr Asp Phe Thr Leu Thr Ile Gly Arg Leu Glu Pro Glu
65                  70                  75                  80

Asp Phe Ala Val Tyr Tyr Cys Leu Gln Trp Ser Ser Asp Pro Pro Thr
                85                  90                  95

Phe Gly Gln Gly Thr Lys Leu Glu Ile Lys
            100                 105

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209, LGT-210 and LGT-211
``` light chain CDR1 peptide

<400> SEQUENCE: 114

Arg Ala Ser Gln Ser Val Ser Tyr Met His
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209, LGT-210 and LGT-211
      light chain CDR1 peptide

<400> SEQUENCE: 115

Gly Val Phe Arg Arg Ala Thr
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      mouse anti-PCSK9 monoclonal antibody LFU720 and anti-PCSK9
      monoclonal antibody clones LGT-209, LGT-210 and LGT-211 light
      chain CDR3 peptide

<400> SEQUENCE: 116

Leu Gln Trp Ser Ser Asp Pro Pro Thr
1               5

<210> SEQ ID NO 117
<211> LENGTH: 118
<212> TYPE: PRT
<213> ORGANISM: Homo sapiens

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Phe Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 118

Gly Tyr Thr Phe Thr Ser Tyr
1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Pro Phe Gly Gly Arg
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      variable heavy chain CDR peptide

<400> SEQUENCE: 120

Glu Arg Pro Leu Tyr Ala Ser Asp Leu
1               5

<210> SEQ ID NO 121
<211> LENGTH: 107
<212> TYPE: PRT
<213> ORGANISM: Homo sapiens

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 122

Arg Ala Ser Gln Gly Ile Ser Ser Ala Leu Ala
1               5                   10

<210> SEQ ID NO 123
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 123

Ser Ala Ser Tyr Arg Tyr Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 124

Gln Gln Arg Tyr Ser Leu Trp Arg Thr
1               5

<210> SEQ ID NO 125
<211> LENGTH: 118
<212> TYPE: PRT
<213> ORGANISM: Homo sapiens

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Glu Ile His Pro Ser Gly Gly Arg Thr Asn Tyr Asn Glu Lys Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Met Asp Tyr Trp Gly Gln Gly Thr
            100                 105                 110

Thr Val Thr Val Ser Ser
        115

<210> SEQ ID NO 126
<211> LENGTH: 10
<212> TYPE: PRT
<213> ORGANISM: Homo sapiens

<400> SEQUENCE: 126

Gly Tyr Thr Phe Thr Ser Tyr Tyr Met His
1               5                   10

<210> SEQ ID NO 127
<211> LENGTH: 17
<212> TYPE: PRT
<213> ORGANISM: Homo sapiens

<400> SEQUENCE: 127

Glu Ile His Pro Ser Gly Gly Arg Thr Asn Tyr Asn Glu Lys Phe Lys
1               5                   10                  15
```

Ser

<210> SEQ ID NO 128
<211> LENGTH: 9
<212> TYPE: PRT
<213> ORGANISM: Homo sapiens

<400> SEQUENCE: 128

Glu Arg Pro Leu Tyr Ala Met Asp Tyr
1               5

<210> SEQ ID NO 129
<211> LENGTH: 107
<212> TYPE: PRT
<213> ORGANISM: Homo sapiens

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr His Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 130
<211> LENGTH: 11
<212> TYPE: PRT
<213> ORGANISM: Homo sapiens

<400> SEQUENCE: 130

Lys Ala Ser Gln Asp Val His Thr Ala Val Ala
1               5                   10

<210> SEQ ID NO 131
<211> LENGTH: 7
<212> TYPE: PRT
<213> ORGANISM: Homo sapiens

<400> SEQUENCE: 131

His Ala Ser Tyr Arg Tyr Thr
1               5

<210> SEQ ID NO 132
<211> LENGTH: 9
<212> TYPE: PRT
<213> ORGANISM: Homo sapiens

<400> SEQUENCE: 132

Gln Gln Arg Tyr Ser Leu Trp Arg Thr
1               5

<210> SEQ ID NO 133
<211> LENGTH: 118
<212> TYPE: PRT

<213> ORGANISM: Homo sapiens

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile His Pro Ser Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
            115

<210> SEQ ID NO 134
<211> LENGTH: 10
<212> TYPE: PRT
<213> ORGANISM: Homo sapiens

<400> SEQUENCE: 134

Gly Tyr Thr Phe Thr Ser Tyr Tyr Met His
1               5                   10

<210> SEQ ID NO 135
<211> LENGTH: 17
<212> TYPE: PRT
<213> ORGANISM: Homo sapiens

<400> SEQUENCE: 135

Glu Ile His Pro Ser Gly Gly Arg Thr Asn Tyr Asn Glu Lys Phe Lys
1               5                   10                  15

Ser

<210> SEQ ID NO 136
<211> LENGTH: 9
<212> TYPE: PRT
<213> ORGANISM: Homo sapiens

<400> SEQUENCE: 136

Glu Arg Pro Leu Tyr Ala Ser Asp Leu
1               5

<210> SEQ ID NO 137
<211> LENGTH: 107
<212> TYPE: PRT
<213> ORGANISM: Homo sapiens

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

```
Tyr His Ala Ser Tyr Arg Tyr Thr Gly Val Pro Ser Arg Phe Ser Gly
     50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Arg Tyr Ser Leu Trp Arg
                85                  90                  95
Thr Phe Gly Gln Gly Thr Lys Leu Glu Ile Lys
            100                 105
```

<210> SEQ ID NO 138
<211> LENGTH: 11
<212> TYPE: PRT
<213> ORGANISM: Homo sapiens

<400> SEQUENCE: 138

```
Lys Ala Ser Gln Asp Val His Thr Ala Val Ala
1               5                   10
```

<210> SEQ ID NO 139
<211> LENGTH: 7
<212> TYPE: PRT
<213> ORGANISM: Homo sapiens

<400> SEQUENCE: 139

```
His Ala Ser Tyr Arg Tyr Thr
1               5
```

<210> SEQ ID NO 140
<211> LENGTH: 9
<212> TYPE: PRT
<213> ORGANISM: Homo sapiens

<400> SEQUENCE: 140

```
Gln Gln Arg Tyr Ser Leu Trp Arg Thr
1               5
```

<210> SEQ ID NO 141
<211> LENGTH: 118
<212> TYPE: PRT
<213> ORGANISM: Mus musculus

<400> SEQUENCE: 141

```
Gln Val Gln Leu Gln Gln Pro Gly Ala Glu Leu Val Lys Pro Gly Ala
1               5                   10                  15
Ser Val Lys Leu Ser Cys Lys Ala Ser Gly Tyr Thr Phe Thr Ser Tyr
                20                  25                  30
Trp Met His Trp Val Lys Gln Arg Pro Gly Gln Gly Leu Glu Trp Ile
            35                  40                  45
Gly Glu Ile Asn Pro Ser Asn Gly Arg Thr Asn Tyr Asn Glu Lys Phe
        50                  55                  60
Lys Ser Lys Ala Thr Leu Thr Val Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Glu Arg Pro Leu Tyr Ala Met Asp Tyr Trp Gly Gln Gly Thr
                100                 105                 110
Ser Val Thr Val Ser Ser
            115
```

```
<210> SEQ ID NO 142
<211> LENGTH: 7
<212> TYPE: PRT
<213> ORGANISM: Mus musculus

<400> SEQUENCE: 142

Gly Tyr Thr Phe Thr Ser Tyr
1               5

<210> SEQ ID NO 143
<211> LENGTH: 6
<212> TYPE: PRT
<213> ORGANISM: Mus musculus

<400> SEQUENCE: 143

Asn Pro Ser Asn Gly Arg
1               5

<210> SEQ ID NO 144
<211> LENGTH: 9
<212> TYPE: PRT
<213> ORGANISM: Mus musculus

<400> SEQUENCE: 144

Glu Arg Pro Leu Tyr Ala Met Asp Tyr
1               5

<210> SEQ ID NO 145
<211> LENGTH: 108
<212> TYPE: PRT
<213> ORGANISM: Mus musculus

<400> SEQUENCE: 145

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Arg Tyr Ser Thr Pro Arg
                85                  90                  95

Thr Phe Gly Gly Gly Thr Lys Leu Glu Ile Lys Arg
            100                 105

<210> SEQ ID NO 146
<211> LENGTH: 11
<212> TYPE: PRT
<213> ORGANISM: Mus musculus

<400> SEQUENCE: 146

Lys Ala Ser Gln Asp Val Ser Thr Ala Val Ala
1               5                   10

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
``` variable light chain CDR peptide

<400> SEQUENCE: 147

Ser Ala Ser Tyr Arg Tyr Thr
1               5

<210> SEQ ID NO 148
<211> LENGTH: 9
<212> TYPE: PRT
<213> ORGANISM: Mus musculus

<400> SEQUENCE: 148

Gln Gln Arg Tyr Ser Thr Pro Arg Thr
1               5

<210> SEQ ID NO 149
<211> LENGTH: 115
<212> TYPE: PRT
<213> ORGANISM: Mus musculus

<400> SEQUENCE: 149

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Thr Thr Tyr Asn Gln Lys Phe
        50                  55                  60

Lys Gly Lys Ala Thr Leu Thr Val Asp Lys Ser Tyr Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Leu Leu Phe Ala Tyr Trp Gly Gln Gly Thr Leu Val Thr
                100                 105                 110

Val Ser Ala
        115

<210> SEQ ID NO 150
<211> LENGTH: 7
<212> TYPE: PRT
<213> ORGANISM: Mus musculus

<400> SEQUENCE: 150

Gly Tyr Thr Phe Thr Asp Tyr
1               5

<210> SEQ ID NO 151
<211> LENGTH: 6
<212> TYPE: PRT
<213> ORGANISM: Mus musculus

<400> SEQUENCE: 151

Asn Pro Asn Asn Gly Gly
1               5

<210> SEQ ID NO 152
<211> LENGTH: 6
<212> TYPE: PRT
<213> ORGANISM: Mus musculus

<400> SEQUENCE: 152

```
Trp Leu Leu Phe Ala Tyr
1               5

<210> SEQ ID NO 153
<211> LENGTH: 108
<212> TYPE: PRT
<213> ORGANISM: Mus musculus

<400> SEQUENCE: 153

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Leu Ser
65                  70                  75                  80

Glu Asp Leu Ala Glu Tyr Phe Cys Gln Gln Phe Tyr Ser Tyr Pro Tyr
                85                  90                  95

Thr Phe Gly Gly Gly Thr Lys Leu Glu Ile Lys Arg
            100                 105

<210> SEQ ID NO 154
<211> LENGTH: 11
<212> TYPE: PRT
<213> ORGANISM: Mus musculus

<400> SEQUENCE: 154

Lys Ala Ser Gln Asn Val Gly Thr Asn Val Ala
1               5                   10

<210> SEQ ID NO 155
<211> LENGTH: 7
<212> TYPE: PRT
<213> ORGANISM: Mus musculus

<400> SEQUENCE: 155

Ser Ala Ser Tyr Arg Tyr Ser
1               5

<210> SEQ ID NO 156
<211> LENGTH: 9
<212> TYPE: PRT
<213> ORGANISM: Mus musculus

<400> SEQUENCE: 156

Gln Gln Phe Tyr Ser Tyr Pro Tyr Thr
1               5

<210> SEQ ID NO 157
<211> LENGTH: 123
<212> TYPE: PRT
<213> ORGANISM: Mus musculus

<400> SEQUENCE: 157

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30
```

-continued

```
Tyr Met Asn Trp Val Lys Gln Ser His Gly Lys Ser Leu Glu Trp Ile
         35                  40                  45
Gly Asp Ile Asn Pro Asn Asn Gly Gly Thr Ser Tyr Asn Gln Lys Phe
     50                  55                  60
Lys Gly Lys Ala Thr Leu Thr Val Asp Lys Ser Ser Thr Ala Tyr
 65                  70                  75                  80
Met Glu Leu Arg Ser Leu Thr Ser Glu Asp Ser Ala Val Tyr Tyr Cys
                 85                  90                  95
Ala Gly Gly Gly Ile Tyr Tyr Arg Tyr Asp Arg Asn Tyr Phe Asp Tyr
                100                 105                 110
Trp Gly Gln Gly Thr Thr Leu Thr Val Ser Ser
            115                 120
```

<210> SEQ ID NO 158
<211> LENGTH: 7
<212> TYPE: PRT
<213> ORGANISM: Mus musculus

<400> SEQUENCE: 158

```
Gly Tyr Thr Phe Thr Asp Tyr
 1               5
```

<210> SEQ ID NO 159
<211> LENGTH: 6
<212> TYPE: PRT
<213> ORGANISM: Mus musculus

<400> SEQUENCE: 159

```
Asn Pro Asn Asn Gly Gly
 1               5
```

<210> SEQ ID NO 160
<211> LENGTH: 14
<212> TYPE: PRT
<213> ORGANISM: Mus musculus

<400> SEQUENCE: 160

```
Gly Gly Ile Tyr Tyr Arg Tyr Asp Arg Asn Tyr Phe Asp Tyr
 1               5                  10
```

<210> SEQ ID NO 161
<211> LENGTH: 107
<212> TYPE: PRT
<213> ORGANISM: Mus musculus

<400> SEQUENCE: 161

```
Asp Ile Gln Met Thr Gln Thr Thr Ser Ser Leu Ser Ala Ser Leu Gly
 1               5                  10                  15
Asp Arg Val Thr Ile Ser Cys Ser Ala Ser Gln Gly Ile Ser Asn Tyr
                 20                  25                  30
Leu Asn Trp Tyr Gln Gln Lys Pro Asp Gly Thr Val Lys Leu Leu Ile
             35                  40                  45
Tyr Tyr Thr Ser Ser Leu His Ser Gly Val Pro Ser Arg Phe Ser Gly
         50                  55                  60
Ser Gly Ser Gly Thr Asp Tyr Ser Leu Thr Ile Ser Asn Leu Glu Pro
 65                  70                  75                  80
Glu Asp Ile Ala Thr Tyr Tyr Cys Gln Gln Tyr Ser Lys Leu Pro Phe
                 85                  90                  95
Thr Phe Gly Ser Gly Thr Lys Leu Glu Ile Lys
```

```
<210> SEQ ID NO 162
<211> LENGTH: 11
<212> TYPE: PRT
<213> ORGANISM: Mus musculus

<400> SEQUENCE: 162

Ser Ala Ser Gln Gly Ile Ser Asn Tyr Leu Asn
1               5                   10

<210> SEQ ID NO 163
<211> LENGTH: 7
<212> TYPE: PRT
<213> ORGANISM: Mus musculus

<400> SEQUENCE: 163

Tyr Thr Ser Ser Leu His Ser
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gln Gln Tyr Ser Lys Leu Pro Phe Thr
1               5

<210> SEQ ID NO 165
<211> LENGTH: 117
<212> TYPE: PRT
<213> ORGANISM: Mus musculus

<400> SEQUENCE: 165

Glu Val Lys Leu Val Glu Ser Gly Gly Leu Val Gln Pro Gly Ser
1               5                   10                  15

Ser Met Lys Leu Ser Cys Thr Ala Ser Gly Phe Thr Phe Ser Asp Tyr
                20                  25                  30

Tyr Met Ala Trp Val Arg Gln Val Pro Glu Lys Gly Leu Glu Trp Val
            35                  40                  45

Ala Asn Ile Asn Tyr Asp Gly Ser Asn Thr Tyr Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Glu Lys Phe Ala Ala Met Asp Tyr Trp Gly Gln Gly Thr Ser
            100                 105                 110

Val Thr Val Ser Ser
        115

<210> SEQ ID NO 166
<211> LENGTH: 7
<212> TYPE: PRT
<213> ORGANISM: Mus musculus

<400> SEQUENCE: 166

Gly Phe Thr Phe Ser Asp Tyr
```

```
1               5

<210> SEQ ID NO 167
<211> LENGTH: 6
<212> TYPE: PRT
<213> ORGANISM: Mus musculus

<400> SEQUENCE: 167

Asn Tyr Asp Gly Ser Asn
1               5

<210> SEQ ID NO 168
<211> LENGTH: 8
<212> TYPE: PRT
<213> ORGANISM: Mus musculus

<400> SEQUENCE: 168

Glu Lys Phe Ala Ala Met Asp Tyr
1               5

<210> SEQ ID NO 169
<211> LENGTH: 108
<212> TYPE: PRT
<213> ORGANISM: Mus musculus

<400> SEQUENCE: 169

Asp Ile Val Met Thr Gln Ser His Lys Phe Met Ser Thr Ser Phe Gly
1               5                   10                  15

Asp Arg Val Ser Ile Thr Cys Lys Ala Ser Gln Asp Val Ser Asn Ala
            20                  25                  30

Leu Ala Trp Tyr Gln Gln Lys Pro Gly His Ser Pro Lys Leu Leu Ile
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys Arg
                100                 105

<210> SEQ ID NO 170
<211> LENGTH: 11
<212> TYPE: PRT
<213> ORGANISM: Mus musculus

<400> SEQUENCE: 170

Lys Ala Ser Gln Asp Val Ser Asn Ala Leu Ala
1               5                   10

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 171

Ser Ala Ser Tyr Arg Tyr Thr
1               5
```

```
<210> SEQ ID NO 172
<211> LENGTH: 9
<212> TYPE: PRT
<213> ORGANISM: Mus musculus

<400> SEQUENCE: 172

Gln Gln His Tyr Ser Thr Pro Trp Thr
1               5

<210> SEQ ID NO 173
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Arg His
            20                  25                  30

Thr Ile His Trp Val Arg Gln Ala Pro Gly Lys Gly Leu Glu Trp Val
        35                  40                  45

Ala Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Phe Thr Phe Thr Arg His Thr Ile His
1               5                   10

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Arg Ile Ser Pro Ala Asn Gly Asn Thr Asn Tyr Ala Asp Ser Val Lys
1               5                   10                  15

Gly

<210> SEQ ID NO 176
<211> LENGTH: 12
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 176

Trp Ile Gly Ser Arg Glu Leu Tyr Ile Met Asp Tyr
1               5                   10

<210> SEQ ID NO 177
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Ile Gln Pro
                85                  90                  95

Thr Phe Gly Gln Gly Thr Lys Val Glu Ile Lys Arg
            100                 105

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Arg Ala Ser Gln Asp Val Ser Thr Ala Val Ala
1               5                   10

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Ala Ser Phe Leu Tyr Ser
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 180

Gln Gln Ser Tyr Arg Ile Gln Pro Thr
1               5

<210> SEQ ID NO 181
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Thr
            20                  25                  30

Ala Ile His Trp Val Arg Gln Ala Pro Gly Lys Gly Leu Glu Trp Val
        35                  40                  45

Ala Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Phe Thr Phe Ser Ser Thr Ala Ile His
1               5                   10

<210> SEQ ID NO 183
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Ile Ser Pro Ala Asn Gly Asn Thr Asn Tyr Ala Asp Ser Val Lys
1               5                   10                  15

Gly

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 184

Trp Ile Gly Ser Arg Glu Leu Tyr Ile Met Asp Tyr
1               5                   10

<210> SEQ ID NO 185
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Ala Leu His
                85                  90                  95

Thr Phe Gly Gln Gly Thr Lys Val Glu Ile Lys Arg
            100                 105

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Ala Ser Gln Asp Val Ser Thr Ala Val Ala
1               5                   10

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Ala Ser Phe Leu Tyr Ser
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Gln Ser Tyr Pro Ala Leu His Thr
1               5
```

```
<210> SEQ ID NO 189
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Lys Leu
            20                  25                  30

Gly Met Val Trp Val Arg Gln Ala Pro Gly Lys Gly Leu Glu Trp Val
        35                  40                  45

Ser Thr Ile Ser Ser Gly Gly Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Ser Phe Gln Gly Gly Thr Tyr Thr Tyr Val Met
            100                 105                 110

Asp Tyr Trp Gly Gln Gly Thr Leu Val Thr Val Ser Ser
        115                 120                 125

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Phe Pro Phe Ser Lys Leu Gly Met Val
1               5                   10

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Thr Ile Ser Ser Gly Gly Gly Tyr Thr Tyr Tyr Pro Asp Ser Val Lys
1               5                   10                  15

Gly

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Glu Gly Ile Ser Phe Gln Gly Gly Thr Tyr Thr Tyr Val Met Asp Tyr
1               5                   10                  15
```

<210> SEQ ID NO 193
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Arg
            20                  25                  30

Asn Gly Ile Thr Tyr Ser Tyr Trp Tyr Leu Gln Lys Pro Gly Gln Ser
        35                  40                  45

Pro Gln Leu Leu Ile Tyr Gln Leu Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Tyr Gln Asn
                85                  90                  95

Leu Glu Leu Pro Leu Thr Phe Gly Gln Gly Thr Lys Val Glu Ile Lys
            100                 105                 110

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Ser Ser Lys Ser Leu Leu His Arg Asn Gly Ile Thr Tyr Ser Tyr
1               5                   10                  15

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Leu Ser Asn Leu Ala Ser
1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Tyr Gln Asn Leu Glu Leu Pro Leu Thr
1               5

<210> SEQ ID NO 197
<211> LENGTH: 2076
<212> TYPE: DNA
<213> ORGANISM: Homo sapiens

<400> SEQUENCE: 197

| | | | | | |
|---|---|---|---|---|---|
| atgggcaccg | tcagctccag | gcggtcctgg | tggccgctgc | cactgctgct | gctgctgctg | 60 |
| ctgctcctgg | gtcccgcggg | cgcccgtgcg | caggaggacg | aggacggcga | ctacgaggag | 120 |
| ctggtgctag | ccttgcgttc | cgaggaggac | ggcctggccg | aagcacccga | gcacggaacc | 180 |
| acagccacct | tccaccgctg | cgccaaggat | ccgtggaggt | tgcctggcac | ctacgtggtg | 240 |
| gtgctgaagg | aggagaccca | cctctcgcag | tcagagcgca | ctgcccgccg | cctgcaggcc | 300 |
| caggctgccc | gccggggata | cctcaccaag | atcctgcatg | tcttccatgg | ccttcttcct | 360 |
| ggcttcctgg | tgaagatgag | tggcgacctg | ctggagctgg | ccttgaagtt | gccccatgtc | 420 |
| gactacatcg | aggaggactc | ctctgtcttt | gcccagagca | tcccgtggaa | cctggagcgg | 480 |
| attacccctc | cacggtaccg | ggcggatgaa | taccagcccc | ccgacggagg | cagcctggtg | 540 |
| gaggtgtatc | tcctagacac | cagcatacag | agtgaccacc | gggaaatcga | gggcagggtc | 600 |
| atggtcaccg | acttcgagaa | tgtgcccgag | gaggacggga | cccgcttcca | cagacaggcc | 660 |
| agcaagtgtg | acagtcatgg | cacccacctg | gcagggtgg | tcagcggccg | ggatgccggc | 720 |
| gtggccaagg | gtgccagcat | gcgcagcctg | cgcgtgctca | actgccaagg | gaagggcacg | 780 |
| gttagcggca | ccctcatagg | cctggagttt | attcggaaaa | gccagctggt | ccagcctgtg | 840 |
| gggccactgg | tggtgctgct | gcccctggcg | ggtgggtaca | gccgcgtcct | caacgccgcc | 900 |
| tgccagcgcc | tggcgagggc | tggggtcgtg | ctggtcaccg | ctgccggcaa | cttccgggac | 960 |
| gatgcctgcc | tctactcccc | agcctcagct | cccgaggtca | tcacagttgg | ggccaccaat | 1020 |
| gcccaagacc | agccggtgac | cctggggact | ttggggacca | actttggccg | ctgtgtggac | 1080 |
| ctctttgccc | caggggagga | catcattggt | gcctccagcg | actgcagcac | ctgctttgtg | 1140 |
| tcacagagtg | ggacatcaca | ggctgctgcc | cacgtggctg | gcattgcagc | catgatgctg | 1200 |
| tctgccgagc | cggagctcac | cctggccgag | ttgaggcaga | gactgatcca | cttctctgcc | 1260 |
| aaagatgtca | tcaatgaggc | ctggttccct | gaggaccagc | gggtactgac | ccccaacctg | 1320 |
| gtggccgccc | tgcccccag | cacccatggg | gcaggttggc | agctgttttg | caggactgta | 1380 |
| tggtcagcac | actcggggcc | tacacggatg | ccacagccg | tcgcccgctg | cgccccagat | 1440 |
| gaggagctgc | tgagctgctc | cagtttctcc | aggagtggga | agcggcgggg | cgagcgcatg | 1500 |
| gaggcccaag | ggggcaagct | ggtctgccgg | gcccacaacg | cttttggggg | tgagggtgtc | 1560 |
| tacgccattg | ccaggtgctg | cctgctaccc | caggccaact | gcagcgtcca | cacagctcca | 1620 |
| ccagctgagg | ccagcatggg | gacccgtgtc | cactgccacc | aacagggcca | cgtcctcaca | 1680 |
| ggctgcagct | cccactggga | ggtggaggac | cttggcaccc | acaagccgcc | tgtgctgagg | 1740 |
| ccacgaggtc | agcccaacca | gtgcgtgggc | cacagggagg | ccagcatcca | cgcttcctgc | 1800 |
| tgccatgccc | caggtctgga | atgcaaagtc | aaggagcatg | gaatcccggc | ccctcaggag | 1860 |
| caggtgaccg | tggcctgcga | ggagggctgg | accctgactg | gctgcagtgc | cctccctggg | 1920 |
| acctcccacg | tcctggggc | ctacgccgta | gacaacacgt | gtgtagtcag | gagccgggac | 1980 |
| gtcagcacta | caggcagcac | cagcgaaggg | gccgtgacag | ccgttgccat | ctgctgccgg | 2040 |
| agccggcacc | tggcgcaggc | ctcccaggag | ctccag | | | 2076 |

<210> SEQ ID NO 198
<211> LENGTH: 692
<212> TYPE: PRT
<213> ORGANISM: Homo sapiens

<400> SEQUENCE: 198

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

-continued

```
His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
            675                 680                 685

Gln Glu Leu Gln
    690
```